(12) United States Patent
Brummond et al.

(10) Patent No.: US 9,102,703 B2
(45) Date of Patent: *Aug. 11, 2015

(54) SYNTHESIS, STRUCTURE AND USE OF FUNCTIONALIZED NAPHTHALENES

(71) Applicant: Kay M. Brummond, Pittsburgh, PA (US)

(72) Inventors: Kay M. Brummond, Pittsburgh, PA (US); Laura S. Kocsis, Pittsburgh, PA (US); Erica Benedetti, Villejuif (FR)

(73) Assignee: Kay M. Brummond, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/833,381

(22) Filed: Mar. 15, 2013

(65) Prior Publication Data

US 2013/0310558 A1 Nov. 21, 2013

Related U.S. Application Data

(60) Provisional application No. 61/648,064, filed on May 16, 2013.

(51) Int. Cl.

| | |
|---|---|
| *C07D 295/02* | (2006.01) |
| *C07D 211/00* | (2006.01) |
| *C07D 207/02* | (2006.01) |
| *C07C 211/27* | (2006.01) |
| *C07K 2/00* | (2006.01) |
| *C07D 295/112* | (2006.01) |
| *C07C 225/22* | (2006.01) |
| *C07D 207/06* | (2006.01) |
| *C07D 211/14* | (2006.01) |
| *C07C 221/00* | (2006.01) |
| *C07C 47/55* | (2006.01) |
| *C07C 49/792* | (2006.01) |
| *C07C 69/78* | (2006.01) |
| *C07C 305/00* | (2006.01) |
| *C07C 317/14* | (2006.01) |
| *C07D 209/62* | (2006.01) |
| *C07D 249/06* | (2006.01) |
| *C07D 307/87* | (2006.01) |
| *C07F 9/40* | (2006.01) |
| *C07C 69/757* | (2006.01) |
| *C07C 69/76* | (2006.01) |
| *C07C 49/813* | (2006.01) |
| *C07F 9/50* | (2006.01) |
| *C07F 15/00* | (2006.01) |
| *C07D 307/73* | (2006.01) |
| *C07C 317/44* | (2006.01) |
| *C07K 1/13* | (2006.01) |

(52) U.S. Cl.
CPC . *C07K 2/00* (2013.01); *C07C 47/55* (2013.01); *C07C 49/792* (2013.01); *C07C 49/813* (2013.01); *C07C 69/757* (2013.01); *C07C 69/76* (2013.01); *C07C 69/78* (2013.01); *C07C 221/00* (2013.01); *C07C 225/22* (2013.01); *C07C 305/00* (2013.01); *C07C 317/14* (2013.01); *C07C 317/44* (2013.01); *C07D 207/06* (2013.01); *C07D 209/62* (2013.01); *C07D 211/14* (2013.01); *C07D 249/06* (2013.01); *C07D 295/112* (2013.01); *C07D 307/73* (2013.01); *C07D 307/87* (2013.01); *C07F 9/4015* (2013.01); *C07F 9/4018* (2013.01); *C07F 9/4056* (2013.01); *C07F 9/4075* (2013.01); *C07F 9/5022* (2013.01); *C07F 15/006* (2013.01); *C07C 2103/14* (2013.01); *C07K 1/13* (2013.01)

(58) Field of Classification Search
CPC .. C07D 295/02; C07D 211/00; C07D 207/02; C07C 211/27
See application file for complete search history.

(56) References Cited

U.S. PATENT DOCUMENTS

| | | | |
|---|---|---|---|
| 7,291,366 B2 | 11/2007 | Lietzau et al. | |
| 7,575,785 B2 | 8/2009 | Lietzau et al. | |
| 7,612,243 B2 | 11/2009 | Lietzau et al. | |

OTHER PUBLICATIONS

Database Registry Chemical Abstracts Service, Columbus, Ohio, Accession No. RN 1273666-24-2, Entered STN: Apr. 3, 2011.*
Kocsis L. S., et al. A Thermal Dehydrogenative Diels-Alder Reaction of Styrenes for the Concise Synthesis of Functionalized Naphthalenes. Org. Lett. 2012, 14, 4430-4433.
Benedetti, E., et al. Synthesis and Photophysical Properties of a Series of Cyclopenta[b] naphthalene Solvatochromic Fluorophores. J. Am. Chem. Soc. 2012, 134, 12418-12421.
Benedetti, E., et al. Attachable Solvatochromic Fluorophores and Bioconjugation Studies. Org. Lett. 2013, 15, 2578-2581.
Trapping Thermally Generated Biradicals from the [2+2] Cycloaddition Reaction of Allene-ynes at ACS National Meeting, Aug. 28-Sep. 1, 2011, Poster 17457.
Thermal Intramolecular Diels-Alder Reactions of Styrenes to Access Functionalized Aromatic Substrates at ACS National Meeting, Aug. 23, 2012—Poster 14338.
Kashima et al., Chem. Pharm. Bull. 1991, 39, 192-194.
Klemm, L.H. et al., Intramolecular Diels-Alder Reactions. VI. Synthesis of 3-Hydroxymethyl-2-naphthoic Acid Lactones. J. Org. Chem. 1971, 36, 2169-2172.

(Continued)

*Primary Examiner* — Samantha Shterengarts
(74) *Attorney, Agent, or Firm* — Joseph L. Kent

(57) ABSTRACT

Methods for the synthesis and use of functionalized, substituted naphthalenes are described. The functionalized, substituted naphthalenes display useful properties including liquid crystals and fluorescence properties, such as solvatochromatic fluorescence, with high quantum yields, Stoke's shift, and show emission maxima that are significantly red-shifted.

15 Claims, 14 Drawing Sheets

(56) References Cited

OTHER PUBLICATIONS

Klemm L.H., et al., Intramolecular Diels-Alder Reactions. J. Org. Chem. 1976, 41, 2571-2579.

Klemm L.H. Intramolecular Diels-Alder Reactions. XII. Competitive [4+2] and [2+2] Cycloadditions of N-(Phenylpropargyl)-cis-cinnamamide. J. Org. Chem. 1976, 41, 3813-3819.

Chackalamannil et al., A Facile Diels-Alder Route to Dihydronaphthofuranones. Tetrahedron Lett. 2000, 41, 4043-4047.

Chackalamannil et al., Mechanism Leading to the Observed Product of Intramolecular Aryl Diels-Alder Reaction. Tetrahedron Lett. 2002, 43, 5101-5103.

Clasby et al., Himbacine Derived Thrombin Receptor Antagonists: Discovery of a New Tricyclic Core. Bioorg. Med. Chem. Lett. 2007, 17, 3647-3651.

Ruijter et al., Synthesis of Polycyclic Alkaloid-Type Compounds by an N-Acyliminium Pictet-Spengler/Diels-Alder Sequence. Synlett 2010, 16, 2485-2489.

Toyota et al., A novel synthesis of the basic carbon framework of Fredericamycin A. Tetrahedron Lett. 1989, 30, 829-832.

Ozawa et al., Dehydrogenative Diels-Alder Reaction. Org. Lett. 2011, 13, 5390-5393.

Ciganek, E. The Intramolecular Diels-Alder Reaction. In Organic Reactions; Dauben, W. J. Ed.; John Wiley and Sons, Inc.: 1984; vol. 32, pp. 1-374.

Klemm et al., Electroreduction of α,β-Unsaturated Esters. J. Org. Chem. 1971, 36, 3740-3743.

Klemm et al., Intramolecular Diels-Alder Reactions. V. Synthesis of Dehydro-β-peltatin Methyl Ether. J. Org. Chem. 1968, 33, 1268-1269.

Klemm et al., An Intramolecular Diels-Alder Reaction. A Simple Synthesis of γ-Apopicropodophyllin. Tetrahedron Lett. 1963, 4, 1243-1245.

Klemm et al., Intramolecular Diels-Alder Reactions. III. Cyclizations of trans-cinnamyl and Phenylpropargyl Phenylpropiolates. J. Org. Chem. 1966, 31, 2376-2380.

Klemm et al., Intramolecular Diels-Alder Reactions. VIII. Syntheses of Phenolic Cyclolignan Lactones. J. Heterocycl. Chem. 1972, 9, 423-426.

Klemm et al., The Intramolecular Diels-Alder Reaction as a Route to Synthetic Lignan Lactones. Tetrahedron 1966, 22, 1797-1808.

Klemm et al., Intramolecular Diels-Alder Reactions. IX. Syntheses of N-Benzylcyclolignan Lactams. J. Heterocycl. Chem. 1972, 9, 1215-1218.

Tanoguchi et al., Studies on the Constituents of the Seeds of *Hernandia ovigera* L. VII. Syntheses of (±)-Hernolactone and (±)-Hernandin. Chem. Pharm. Bull. 1989, 37, 68-72.

Joshi et al., Attenuol—Structure, Stereochemistry and Synthesis. Tetrahedron 1979, 35, 1665-1671.

Laszlo et al., Design and Synthesis of a Potential Dopamine D-1 Antagonist. Helv. Chim. Acta 1988, 71, 1697-1703.

Stevenson et al., Lignan Lactones. Synthesis of (±)-Collinusin and Justicidin B. J. Org. Chem. 1971, 36, 3453-3455.

Klemm et al., Intramolecular Diels-Alder Cyclization into the Thiophene Ring. J. Heterocycl. Chem. 1965, 2, 225-227.

Hajbi et al., Synthesis and Biological Activities of New Furo[3,4-b]carbazoles: Potential Topoisomerase II Inhibitors. Eur. J. Med. Chem. 2010, 45, 5428-5437.

Chilloux et al., Synthesis of New 4-(3,4,5-Trimethoxyphenyl)-3H-Furo [3,4-b]Carbazole-3-ones Derivatives. Lett. Org. Chem. 2007, 4, 198-202.

Wessig et al., The Dehydro-Diels-Alder Reaction. Chem. Rev. 2008, 108, 2051-2063.

Parker et al., Vinylquinone Ketals as Diels-Alder Dienes. Construction of Functionalized Naphthalenes and Nonlinear Polycyclic Aromatics. J. Am. Chem. Soc. 1989, 111, 5948.

Everett et al., Does PRODAN Possess an O-TICT Excited State? Synthesis and Properties of Two Constrained Derivatives. J. Phys. Chem. A 2010, 114, 4946-4950.

Lakowicz, J. R. Principles of Fluorescence Spectroscopy, 3rd ed.; Springer: New York, 2006, pp. 217-226.

Weber et al., Synthesis and Spectral Properties of a Hydrophobic Fluorescent Probe: 6-Propionyl-2-(dimethylamino)naphthalene. Biochemistry 1979, 18, 3075-3078.

Loving et al., Monitoring Protein Interactions and Dynamics with Solvatochromic Fluorophores. Trends Biotechnol. 2009, 28, 73-83.

Chang et al., ANCA: A Family of Fluorescent Probes that Bind and Stain Amyloid Plaques in Human Tissue. ACS Chem. Neuro. 2011, 2, 249-255.

Abelt et al., 2,5-PRODAN: Synthesis and Properties. Photo. Photobio. Sci. 2011, 10, 618-622.

\* cited by examiner

FIG. 3
FIG. 3A
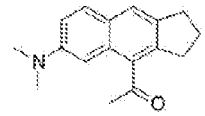
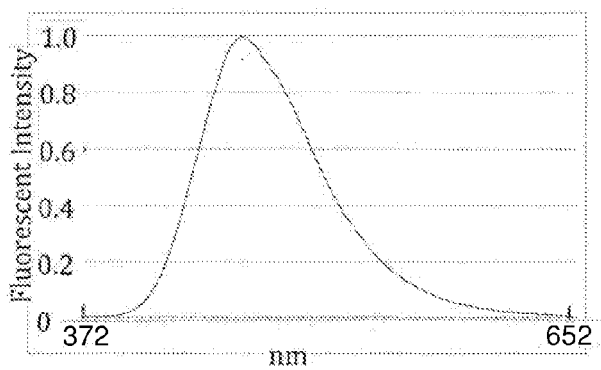
$10^{-5}$M solution in cyclohexane
- Absorbance max: 373 nm
- Emission max: 466 nm
- QY:[1] 45%
FIG. 3B
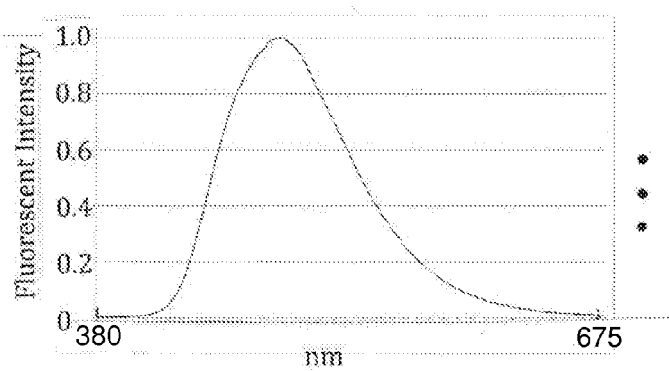
$10^{-5}$M solution in toluene
- Absorbance max: 376 nm
- Emission max: 490 nm
- QY:[1] 62%
FIG. 3C
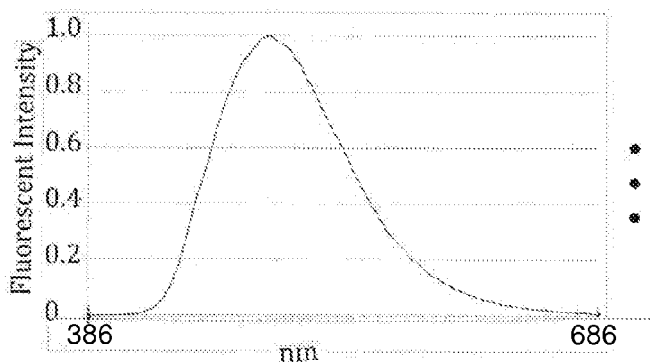
$10^{-5}$M solution in 1,4-dioxane
- Absorbance max: 376 nm
- Emission max: 495 nm
- QY:[1] 46%
FIG. 3D
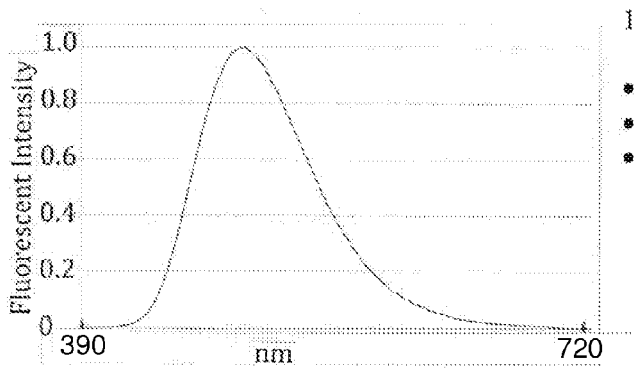
$10^{-5}$M solution in THF
- Absorbance max: 377 nm
- Emission max: 497 nm
- QY:[1] 75%

$10^{-5}$M solution in $CH_2Cl_2$
- Absorbance max: 377 nm
- Emission max: 510 nm
- QY:[1] 99%

$10^{-5}$M solution in $CHCl_3$
- Absorbance max: 377 nm
- Emission max: 516 nm
- QY:[1] 77%

$10^{-5}$M solution in acetonitrile
- Absorbance max: 375 nm
- Emission max: 529 nm
- QY:[1] 99%

$10^{-5}$M solution in DMSO

Absorbance max: 377 nm
- Emission max: 536 nm
- QY:[1] 85%

FIG. 3I
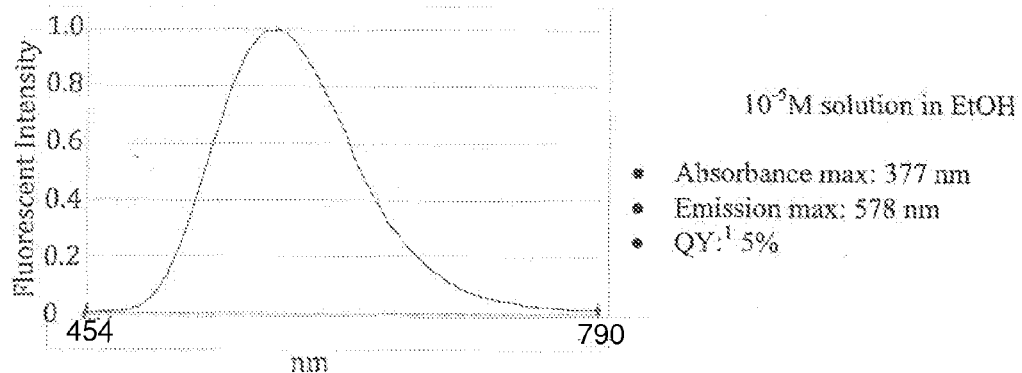
10⁻⁵M solution in EtOH
- Absorbance max: 377 nm
- Emission max: 578 nm
- QY:[1] 5%
FIG. 4
FIG. 4A
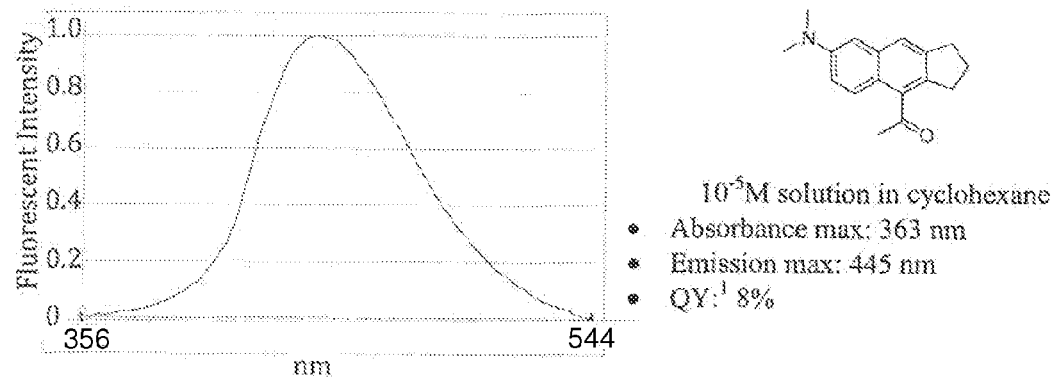
10⁻⁵M solution in cyclohexane
- Absorbance max: 363 nm
- Emission max: 445 nm
- QY:[1] 8%
FIG. 4B
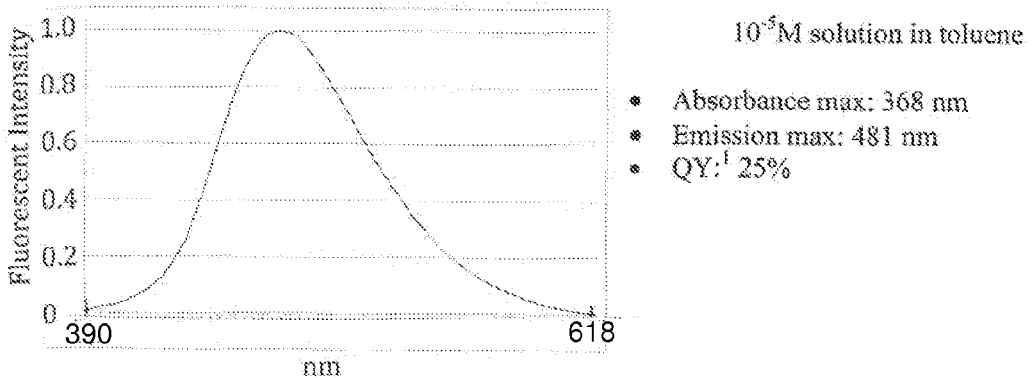
10⁻⁵M solution in toluene
- Absorbance max: 368 nm
- Emission max: 481 nm
- QY:[1] 25%

10⁻⁵M solution in 1,4-dioxane
- Absorbance max: 370 nm
- Emission max: 495 nm
- QY:[1] 38%

10⁻⁵M solution in THF
- Absorbance max: 370 nm
- Emission max: 505 nm
- QY:[1] 34%

10⁻⁵M solution in $CH_2Cl_2$
- Absorbance max: 372 nm
- Emission max: 509 nm
- QY:[1] 82%

10⁻⁵M solution in $CHCl_3$
- Absorbance max: 373 nm
- Emission max: 511 nm
- QY:[1] 41%

FIG. 5
FIG. 5A
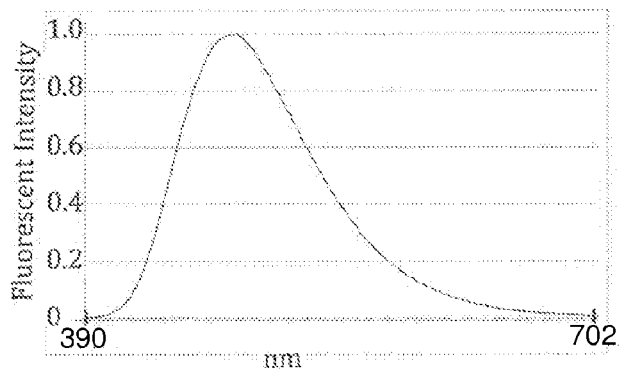
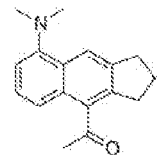
$10^{-5}$M solution in cyclohexane
- Absorbance max: 314 nm
- Emission max: 480 nm
- QY:[1] 28%
FIG. 5B
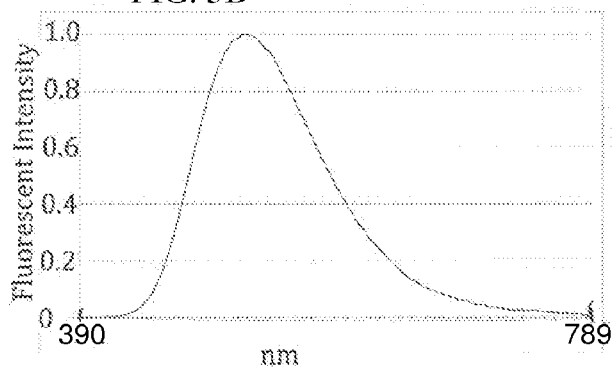
$10^{-5}$M solution in toluene
- Absorbance max: 322 nm
- Emission max: 520 nm
- QY:[1] 47%
FIG. 5C
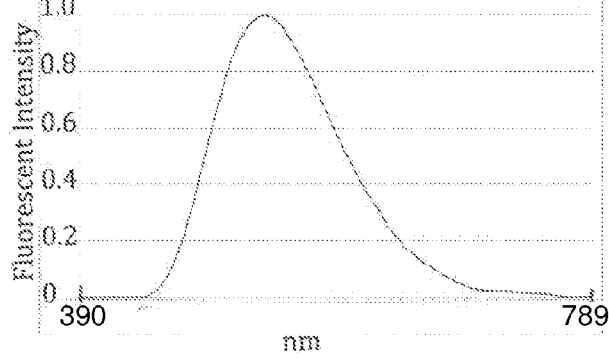
$10^{-5}$M solution in 1,4-dioxane
- Absorbance max: 319 nm
- Emission max: 534 nm
- QY:[1] 44%
FIG. 5D
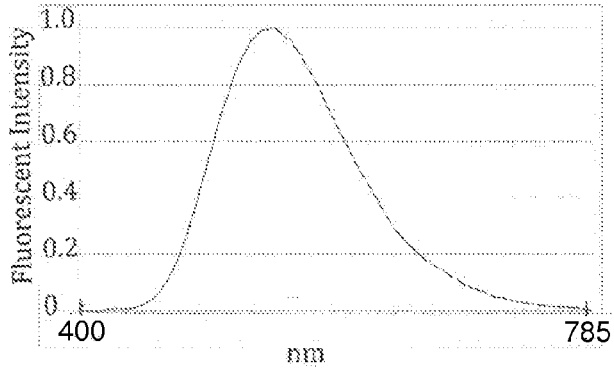
$10^{-5}$M solution in THF
- Absorbance max: 330 nm
- Emission max: 543 nm
- QY:[1] 39%

$10^{-5}$ M solution in $CH_2Cl_2$

- Absorbance max: 334 nm
- Emission max: 562 nm
- QY:[1] 60%

$10^{-5}$ M solution in $CHCl_3$

- Absorbance max: 334 nm
- Emission max: 562 nm
- QY:[1] 40%

$10^{-5}$ M solution in acetonitrile

- Absorbance max: 316 nm
- Emission max: 590 nm
- QY:[1] 23%

$10^{-5}$ M solution in DMSO

- Absorbance max: 334 nm
- Emission max: 598 nm
- QY:[1] 48%

FIG. 5I
10⁻⁵M solution in EtOH
- Absorbance max: 334 nm
- Emission max: 634 nm
- QY:[1] 1.3%
FIG. 6
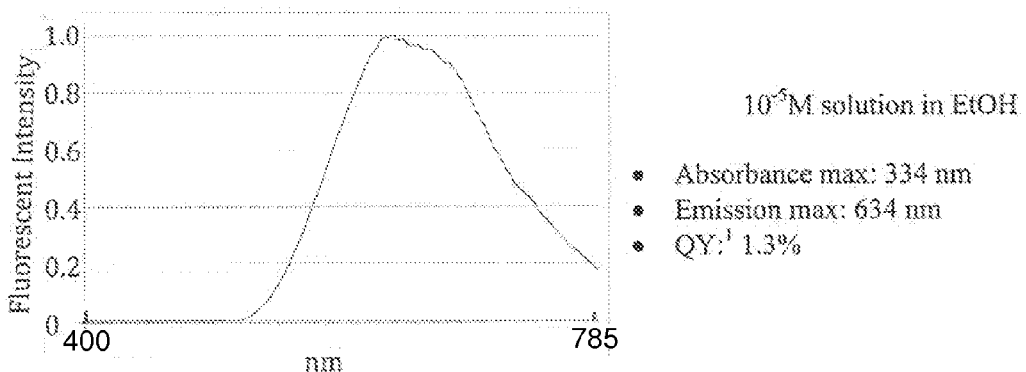
10⁻⁵M solution in $CH_2Cl_2$
- Absorbance max: 390 nm
- Emission max: 513 nm
- QY:[1] 96%
FIG. 7
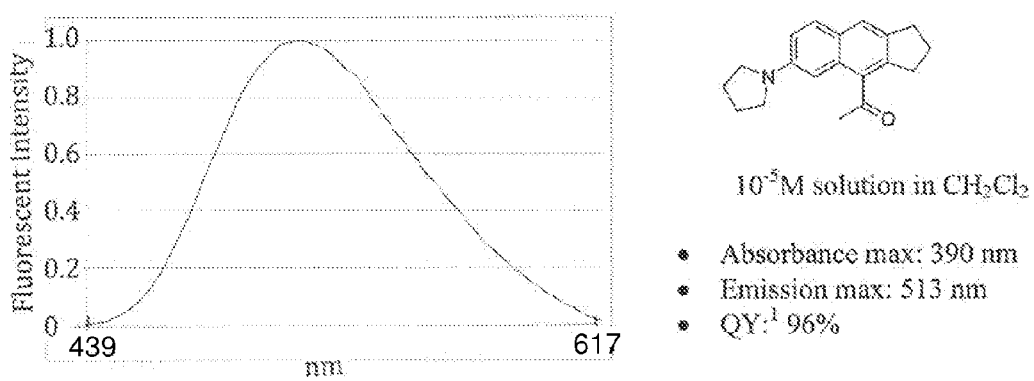
10⁻⁵M solution in $CH_2Cl_2$
- Absorbance max: 362 nm
- Emission max: 515 nm
- QY:[1] 99%

$10^{-5}$M solution in $CH_2Cl_2$

- Absorbance max: 355 nm
- Emission max: 508 nm
- QY:[1] 99%

$10^{-5}$M solution in $CH_2Cl_2$

- Absorbance max: 368 nm
- Emission max: 482 nm
- QY:[1] 97%

$10^{-5}$M solution in $CH_2Cl_2$

- Absorbance max: 367 nm
- Emission max: 493 nm
- QY:[1] 95%

$10^{-5}$M solution in $CH_2Cl_2$

- Absorbance max: 372 nm
- Emission max: 495 nm
- QY:[1] 89%

SYNTHESIS, STRUCTURE AND USE OF FUNCTIONALIZED NAPHTHALENES

CROSS REFERENCE TO RELATED APPLICATIONS

This application claims priority to U.S. Provisional Application Ser. No. 61/648,064, filed May 16, 2013, the disclosure of which is incorporated in its entirety by this reference.

STATEMENT REGARDING FEDERALLY SPONSORED RESEARCH

Portions of the research described herein were supported by U.S. National Science Foundation, Grant CHE0910597. The U.S. Government may have certain rights in this technology.

TECHNICAL FIELD

The present disclosure are related to functionalized, substituted, naphthalene compounds and methods of synthesis of functionalized, substituted, naphthalene compounds. The functionalized, substituted naphthalene compounds display novel fluorescent properties and may also serve as novel liquid crystal compounds.

BACKGROUND

Designing and building small molecules for the purpose of function enables advancement in fields ranging from pharmaceuticals to pesticides. The Diels-Alder (DA) reaction is one of the most powerful and robust transformations for assembling cyclic molecular frameworks, employing a plethora of diene (4π) and dienophile (2π) components capable of delivering a rich diversity of cyclic compounds poised for function. One structural variant is the dehydro-Diels-Alder (DDA) reaction, where one, two, or all three of the double bonds of the classic diene and dienophile are replaced with triple bonds, providing access to substituted aromatic compounds not accessible using other chemistries. The energy price to incorporate the high degree of precursor unsaturation required for the formation of aromatic products can be mitigated by the propensity of cyclohexadiene derivatives to aromatize. Aromatic derivatives, in turn, can be prepared from more saturated precursors, a process defined as a dehydrogenative DA reaction.

A particularly problematic, but potentially useful dehydrogenative DA reaction involves the use of styrene as the diene component and an alkyne dienophile, affording a cycloadduct that can aromatize under oxidative conditions to give naphthalene derivatives (Scheme 1). Problems that can arise when using styrene as the diene range from polymerizations to [2+2] cycloaddition reactions. One solution is to use very reactive dienophiles such as maleic anhydride or benzoquinone. However, the desired cycloadducts are typically obtained in low yields because the reactivity of these dienophiles leads to a second DA reaction with the newly formed diene of the first cycloadduct. Lack of regioselectivity for the styrenyl DA reaction is also a drawback, which can be overcome by carrying out the reaction intramolecularly. The intramolecular styrenyl DA reaction also suffers from low yields and long reaction times, producing mixtures of inseparable dihydronaphthalene and naphthalene products.

Scheme 1. The Styrenyl Dehydrogenative Dehydro DA Reaction

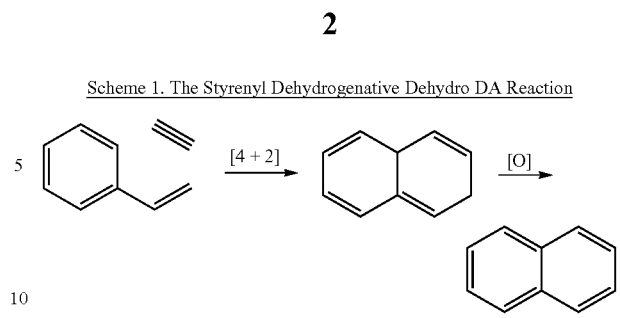

Continued interest in the development of an efficient styrenyl DA reaction is driven by the need for functionalized naphthalene compounds that can serve as valuable building blocks for the synthesis of small molecules in many important areas, such as pharmaceuticals, chiral reagents, liquid crystals, and organic dyes. Moreover, the intramolecular styrenyl DA reaction affords a unique functionalization pattern on the resulting naphthalene derivatives that complements other synthetic approaches.

Fluorescent-based tools are widely used to monitor environments of biological events. Small organic fluorophores are particularly powerful due to rapid response times for monitoring real-time events with excellent spatial resolution. Moreover, their relatively small size minimizes disruption of the environment being studied. Thus, new small molecule-based chemical sensors are continually being developed. Many of these developments involve modifying an existing fluorophore to accommodate a need. For example, Prodan is a compound whose fluorescent emission and quantum yield is unusually dependent upon solvent polarity; in cyclohexane the fluorescent emission is 410 nm and in water it is 534 nm, a bathochromic shift of 124 nm. Prodan is considered to be state of the art for application in biological systems and structural variants of this probe have been prepared, such as the lipophilic Laurdan; the thiol reactive Acrylodan and Badan; and the amino acid-containing Aladan. In addition, a spectrally red-shifted compound, Anthradan, has been prepared that incorporates an anthracene ring between the electron donating and electron withdrawing groups; the emission spectra in hexanes is 483 nm, and in methanol 604 nm. The design and synthesis of new naphthalene-containing fluorophores could be significantly enhanced by novel methods for the construction of aromatic rings.

SUMMARY

The present disclosure is directed to the design and synthesis of new functionalized, substituted, naphthalene compounds which possess unique structures and display useful properties, including fluorescent properties and liquid crystal properties.

According to one embodiment, the present disclosure provides for a substituted, functionalized naphthalene having a structure

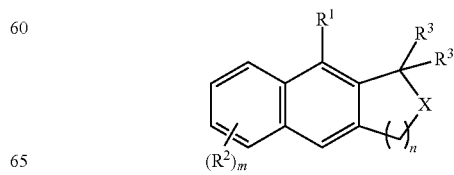

where $R^1$ is a substituent selected from the group consisting of H, $C_1$-$C_{20}$ alkyl, $C_1$-$C_{20}$ alkoxy, phenyl, aryl, heteroaryl, —S(O)$R^4$, —S(O)$_2R^4$, P(O)(O$R^4$)$_2$, and —C(Y)$R^4$ where Y is O, N$R^5$, or S; each $R^2$ is an electron donating group selected from —N($R^6$)$_2$, —O$R^6$, and —S$R^6$; each $R^3$ is H, $C_1$-$C_{20}$ alkyl, or combined as =O; each $R^4$, $R^5$ and $R^6$ is independently selected from H, $C_1$-$C_{20}$ alkyl, $C_1$-$C_{20}$ alkoxy, phenyl, aryl, heteroaryl or may come together to form a cyclic structure; X is CH$_2$, C($R^6$)$_2$, C(CO$_2$Alkyl)$_2$, O, NTs, NH, NCOR$^5$ or N$R^5$; n is an integer from 0 to 2; m is an integer from 1 to 4, provided that either $R^1$ is one of —S(O)$R^4$, —S(O)$_2R^4$, P(O)(O$R^4$)$_2$, and —C(Y)$R^4$ or $R^3$ is =O.

According to another embodiment, this disclosure provides for functionalized substituted naphthalenes as described herein wherein the naphthalene is a fluorophore.

According to another embodiment, the present disclosure provides for functionalized substituted naphthalenes as described herein wherein the naphthalene is a solvatochromatic fluorophore.

According to another embodiment, this disclosure provides for functionalized substituted naphthalenes as described herein wherein the naphthalene is a liquid crystal.

Still further embodiments of the present disclosure provide for a method of synthesizing a substituted, functionalized naphthalene as described herein, the method comprising reacting a 2'-alkynyl substituted halostyrene by a dehydrogenative intramolecular dehydro Diels Alder reaction in the presence of microwave irradiation to form a halo substituted naphthalene; and reacting the halo substituted naphthalene to a cross coupling reaction to form a functionalized naphthalene having a structure

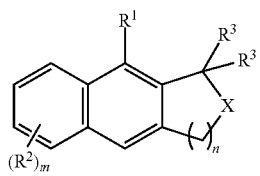

where $R^1$ is a substituent selected from the group consisting of H, $C_1$-$C_{20}$ alkyl, $C_1$-$C_{20}$ alkoxy, phenyl, aryl, heteroaryl, —S(O)$R^4$, —S(O)$_2R^4$, P(O)(O$R^4$)$_2$, and —C(Y)$R^4$ where Y is O, N$R^5$, or S; each $R^2$ is an electron donating group selected from —N($R^6$)$_2$, —O$R^6$, and —S$R^6$; each $R^3$ is H, $C_1$-$C_{20}$ alkyl, or combined as =O; each $R^4$, $R^5$ and $R^6$ is independently selected from H, $C_1$-$C_{20}$ alkyl, $C_1$-$C_{20}$ alkoxy, phenyl, aryl, heteroaryl or may come together to form a cyclic structure; X is CH$_2$, C($R^6$)$_2$, C(CO$_2$Alkyl)$_2$, O, NTs, NH, NCOR$^5$ or N$R^5$; n is an integer from 0 to 2; m is an integer from 1 to 4, provided that either $R^1$ is one of —S(O)$R^4$, —S(O)$_2R^4$, P(O)(O$R^4$)$_2$, and —C(Y)$R^4$ or $R^3$ is =O.

Other embodiments of the present disclosure provide a method for fluorescing a fluorescent functionalized naphthalene having a structure

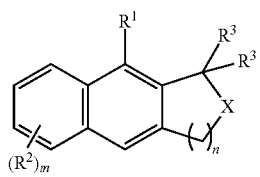

where $R^1$ is a substituent selected from the group consisting of H, $C_1$-$C_{20}$ alkyl, $C_1$-$C_{20}$ alkoxy, phenyl, aryl, heteroaryl, —S(O)$R^4$, —S(O)$_2R^4$, P(O)(O$R^4$)$_2$, and —C(Y)$R^4$ where Y is O, N$R^5$, or S; each $R^2$ is an electron donating group selected from —N($R^6$)$_2$, —O$R^6$, and —S$R^6$; each $R^3$ is H, $C_1$-$C_{20}$ alkyl, or combined as =O; each $R^4$, $R^5$ and $R^6$ is independently selected from H, $C_1$-$C_{20}$ alkyl, $C_1$-$C_{20}$ alkoxy, phenyl, aryl, heteroaryl or may come together to form a cyclic structure; X is CH$_2$, C($R^6$)$_2$, C(CO$_2$Alkyl)$_2$, O, NTs, NH, NCOR$^5$ or N$R^5$; n is an integer from 0 to 2; m is an integer from 1 to 4, provided that either $R^1$ is one of —S(O)$R^4$, —S(O)$_2R^4$, P(O)(O$R^4$)$_2$, and —C(Y)$R^4$ or $R^3$ is =O. The method comprises irradiating the functionalized naphthalene with electromagnetic radiation and measuring the amount of fluorescent light emitted by the irradiated functionalized naphthalene.

Still other embodiments of this disclosure provides for a fluorescent sensor comprising a functionalized, substituted naphthalene having a structure as described herein.

Still other embodiments of the present disclosure provides for a liquid crystal display, photo voltaic device, or conjugated polymer comprising a functionalized, substituted naphthalene having a structure as described herein.

Still other embodiments of the present disclosure proves for a solvatochromatic fluorophore comprising a functionalized, substituted naphthalene having a structure as described herein.

Other embodiments of the compositions and methods of the present disclosure will be apparent to one of skill in the art based upon knowledge acquired by reading this disclosure.

BRIEF DESCRIPTION OF THE DRAWINGS

The various embodiments of the present disclosure will be better understood when read in conjunction with the following Drawings wherein:

FIGS. 3A-3I show the emission spectra for 1-(6-(dimethylamino)-2,3-dihydro-1H-cyclopenta[b]naphthalen-4-yl) ethanone in different solvents, QY is fluorescence quantum yield vs PRODAN in DMSO (91%); excitation wavelength was 334 nm.

FIGS. 4A-4I show the emission spectra for 1-(7-(dimethylamino)-2,3-dihydro-1H-cyclopenta[b]naphthalen-4-yl) ethanone in different solvents, QY is fluorescence quantum yield vs PRODAN in DMSO (91%); excitation wavelength was 334 nm.

Figures 5A-5I show the emission spectra for 1-(8-(dimethylamino)-2,3-dihydro-1H-cyclopenta[b]naphthalen-4-yl)ethanone in different solvents, QY is fluorescence quantum yield vs PRODAN in DMSO (91%); excitation wavelength was 334 nm.

FIG. 6 shows the emission spectra for 1-(6-(pyrrolidin-1-yl)-2,3-dihydro-1H-cyclopenta[b]naphthalen-4-yl)ethanone, QY is fluorescence quantum yield vs PRODAN in DMSO (91%); excitation wavelength was 334 nm.

FIG. 7 shows the emission spectra for 1-(6-(piperidin-1-yl)-2,3-dihydro-1H-cyclopenta[b]naphthalen-4-yl)ethanone, QY is fluorescence quantum yield vs PRODAN in DMSO (91%); excitation wavelength was 334 nm.

DETAILED DESCRIPTION

Figure 1:
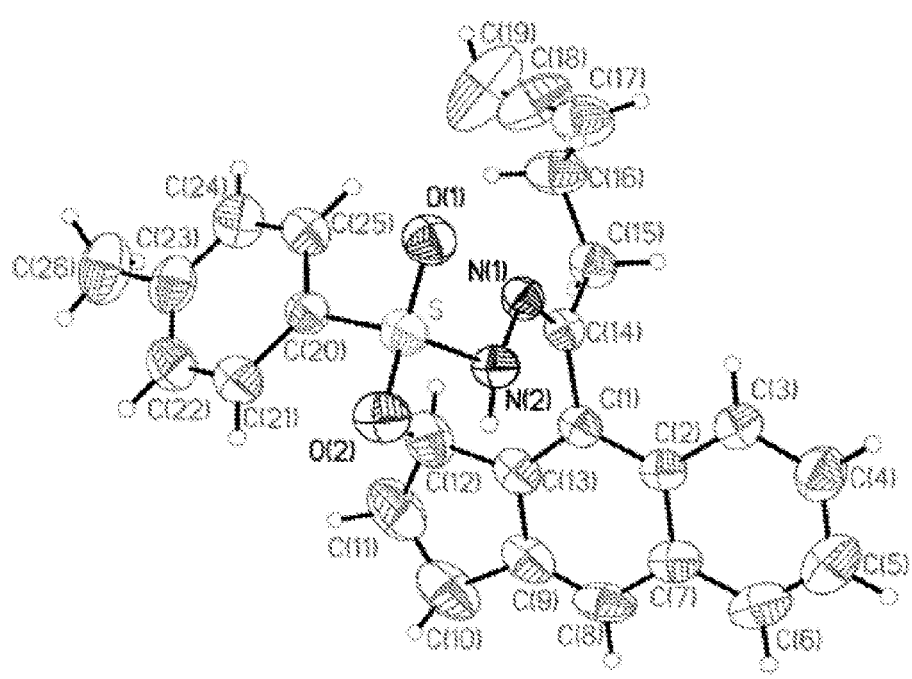
FIG. 1 is an X-ray crystal structure of N'-(1-(2,3-dihydro-1H-cyclopenta[b] naphthalen-4-yl)hexa-4,5-dien-1-ylidene)-4-methylbenzene-sulfonohydrazide (3).

The present disclosure describes novel and non-obvious substituted, functionalized naphthalenes which display useful properties and uses as fluorophores, solvatochromatic fluorophores, components of photovoltaic devices, structural components in conjugated polymers, pharmaceuticals, light harvesting components, and liquid crystals. The present disclosure utilizes an intramolecular didehydro-Diels-Alder (DDA) reaction between a styene and an alkyne linked by a tether for the synthesis of new substituted naphthalene compounds that can be used as fluorescent tags. It was envisioned that a number of modifications can be made, either linearly or combinatorially, to the DDA precursors and/or to the DDA products, leading to novel substituted naphthalene compounds that will be tested for their general chemical and fluorescent properties such as: molecular absorbance, quantum yield, excitation wavelength, emission wavelength, Stokes shift, fluorescent lifetime, photostability, and solubility, that are essential for sensing applications. Examples of modifications to the precursor include but are not limited to, substitution at the terminus of the alkyne ($R^1$), the aromatic ring ($R^2$), the double bond ($R^3$) and/or the tether (XYZ). Examples of modifications that can be made to the product include but are not limited to any or all of the following: conversion of $R^1$ to $R^4$, $R^2$ to $R^5$, $R^3$ to $R^6$, and/or XYZ to ABC.

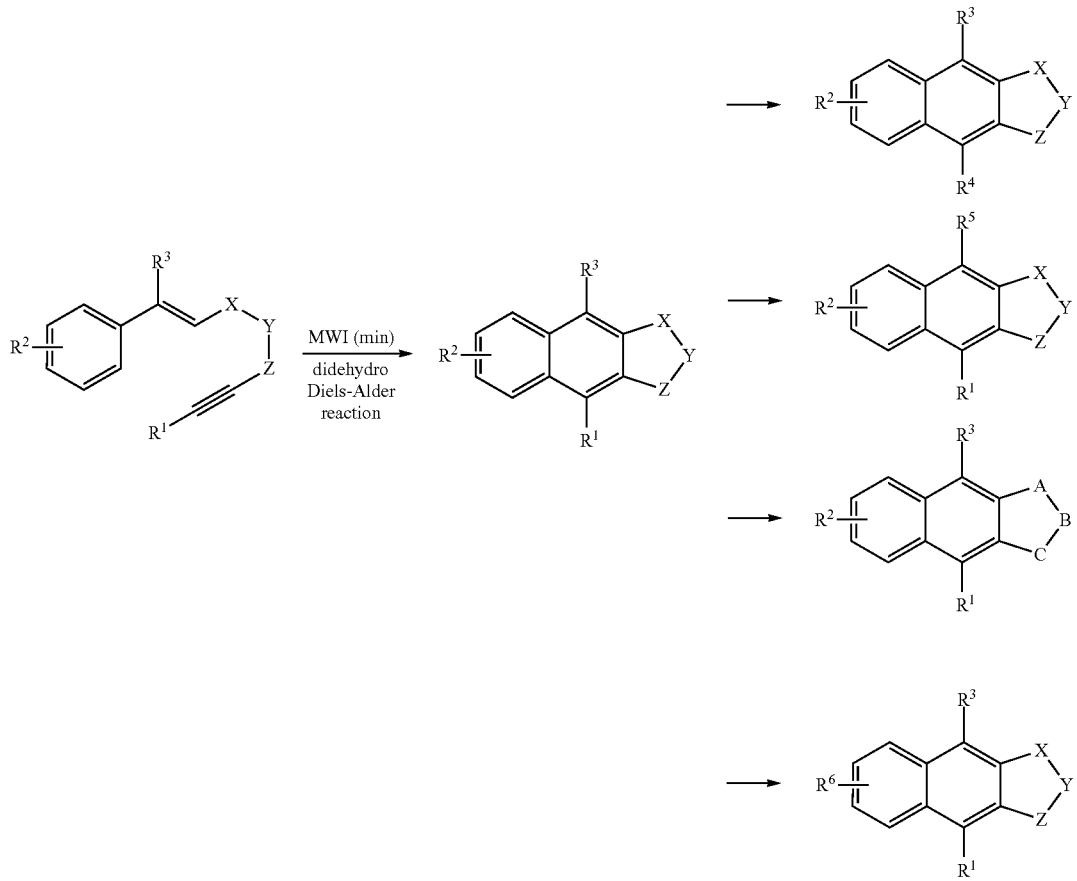

As generally used herein, the terms "include" and "have" mean "comprising". As generally used herein, the term "about" refers to an acceptable degree of error for the quantity measured, given the nature or precision of the measurements. Typical exemplary degrees of error may be within 20%, 10%, or 5% of a given value or range of values. Alternatively, and particularly in biological systems, the term "about" may mean values that are within an order of magnitude, potentially within 5-fold or 2-fold of a given value.

Recently, in our studies directed towards expanding the scope of the thermal [2+2] cycloaddition reaction of allene-ynes, naphthalene 2 was obtained and none of the anticipated [2+2] cycloaddition product between the allene and the alkyne of 1 upon microwave irradiation in ortho-dichlorobenzene at 225° C. for 5 min. While the $^1$H NMR and $^{13}$C NMR spectra of 2 contained well-defined resonances in the aromatic region diagnostic of a cyclopentanaphthalene, verification of the product structure having a linear or angular arrangement was elusive. The cyclopentanaphthalene derivative possessing a linear arrangement of the three rings could originate from the uncommon IMDA discussed above. The angular cyclopentanaphthalene could arise from a thermal [2+2] cycloaddition reaction between the double bond of the styrenyl group and the alkynone, followed by a 4π-electrocyclic ring opening of the corresponding cyclobutene to yield a new diene. Isomerization of the appended double bond from the Z- to the E-isomer, followed by a 6π-electrocyclic ring closing and aromatization would yield the angular product.[13] The linear structure of compound 2 was confirmed by an X-ray crystal structure of o-nitrophenyl sulfonyl hydrazone 3. The outstanding selectivity of this IMDA reaction for the naphthalene product over the dihydronaphthalene product (1:0), the high yield, and an overall interest in naphthalene derivatives compelled us to study this reaction further.

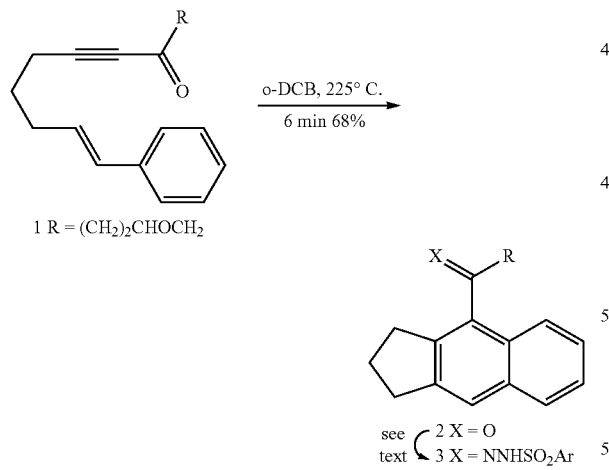

Scheme 2. Dehydrogenative IMDA Reaction

Or investigations differ from existing methods for the synthesis of naphthalene derivatives via the IMDA reaction of styrenes, all of them sharing a few common features such as 1) the enyne precursors contain either a heteroatom and/or a carbonyl group(s) within the tether (mainly amides and esters); 2) limited functionality on the terminus of the alkyne, usually trimethylsilyl (TMS) or phenyl groups, or a hydrogen atom; 3) reaction conditions requiring high temperatures and long reaction times; and 4) most naphthalene products are contaminated with varying quantities of dihydronaphthalene byproducts. Moreover, our initial result directly opposes the work reported by Matsubara, who suggests that a TMS group on the terminus of the alkyne is necessary for the exclusive formation of the naphthalene over the dihydronaphthalene product.

A concise synthesis of a dehydrogenative IMDA styrenyl precursor 5 was accomplished in 3 steps, and in a manner entirely analogous to that used for the preparation of 1. Aldehyde 4 is prepared by a PCC oxidation of commercially available 5-hexyn-1-ol in 81% yield. Next, reaction of the lithium or sodium salt of diethyl benzylphosphonate with aldehyde 4 affords the styrene moiety of 5 in 68% yield. Deprotonation of the alkyne terminus with n-BuLi followed by acetylation of the acetylide produces 5 in 69% yield. For the ensuing IMDA reaction, solvents with lower boiling points were considered because of difficulties in removing high boiling o-dichlorobenzene.

Microwave irradiation of styrene 5 in either 1,2-dichloroethane (DCE) at 180° C. for 30 min or 1,1,1-trifluorotoluene at 180° C. for 180 minutes afforded the cyclopenta-naphthalene derivative 6 in nearly quantitative yield with no additional purification required of the final product (entries 1 and 2, Table 1). With conditions for an efficient and high yielding IMDA reaction utilizing a lower boiling solvent in hand, scope and limitations investigations were initiated. First, substitution on the aryl group was examined; exchanging a hydrogen atom for a chlorine atom was deemed valuable, enabling access to a wide-range of naphthalene derivatives via palladium-catalyzed cross coupling reactions. Moreover, a chlorine atom is more stable and accessible than other halides or groups used for coupling, such as triflates. Styrenyl derivatives 5b, 5c, and 5d were prepared and subjected to microwave irradiation. The para-chlorostyrene 5b gave 7-chloronaphthalene 6b in quantitative yield after 200 min (entry 3). The ortho-chlorostyrene 5c also produced only one product, the 5-chloronaphthalene 6c in 86% yield, even though two products are possible (entry 4). The meta-chlorostyrene 5d gave an inseparable 1.4:1 mixture of the 6-chloro- and 8-chloronaphthalenes, 6d and 6d' in 79% yield (entry 5).

Scheme 3. IMDA Precursor Synthesis

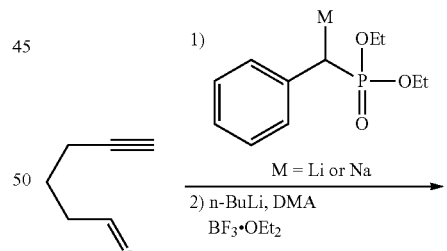

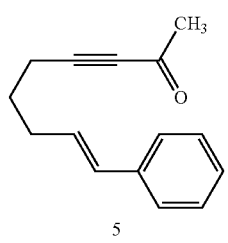

5

Next, a number of functional groups on the terminus of the alkyne were investigated in the IMDA reaction. Substitution of the alkyne with a phenyl methanone gave the cycloadduct 6e in quantitative yield after 90 min (entry 6). Reaction scale did not affect the yield of this reaction, but it did have an affect on the reaction time; for example, 50 mg of 5e afforded 6e in 90 min, while 200 mg of 5e required a reaction time of 130 min. Placement of the methylsulfonyl and phenylsulfonyl groups on the terminus of the alkyne to produce 5f and 5g resulted in a facile IMDA reaction to give 6f and 6g in 78% and 89% yield, respectively (entries 7 and 8). Sulfoxide 5h gave a slightly lower yield, but still afforded the naphthalene product 6h selectively (entry 9). Similarly, the diethyl phosphonate substituted alkyne 5i produced 6i in greater than 95% yield in 150 min (entry 10). Alkynal 5j affords the naphthalene 6j in 83% yield in 45 min (entry 11). A substrate with a methyl ester on the alkyne terminus 5k, slowed the reaction considerably, requiring 600 min to obtain complete conversion to 6k in 76% yield (entry 12). The reaction time could be shortened from 600 to 90 min by heating to 225° C. in o-dichlorobenzene; this also resulted in an improved yield of 97% (entry 13). The rate of these IMDA reactions (entries 1-13) corresponds well with Frontier Molecular Orbital Theory and HOMO-LUMO gaps.

Finally, structural changes in the tether were examined. Extending the tether by one methylene unit gave precursor 5l that required heating at 300° C. for 50 min in o-dichlorobenzene but provided the product 6l in quantitative yield (heating at 225° C. for 240 minutes resulted in recovery of starting material). To the best of our knowledge, this is the first successful styrenyl IMDA reaction using a four-atom tether to provide naphthalene containing an additional six-membered ring. Reaction of the precursor 5m with an all carbon tether possessing a diester moiety afforded only 6m in greater than 95% yield in 30 min (entry 15). Next, an ether tether was used to connect the styrene and the alkyne. The cycloaddition of 5n was complete in 30 min and gave a 2:1 ratio of the naphthalene 6n to the dihydronaphthalene 7m (entry 16). The toluenesulfonamide substrate 5o also afforded a mixture of products, but in a 2:1 ratio of the dihydronaphthalene 7o to naphthalene 6o in 10 min in a combined yield of 86% (entry 17). The case of the toluenesulfonamide tether with a chloro

TABLE 1

Microwave-Assisted Dehydrogenative Diels-Alder Reaction

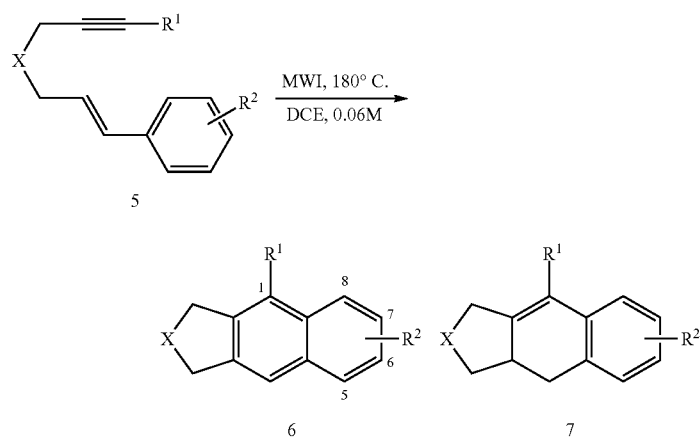

| entry | 5 | $R^1$ | $R^2$ | X | time | 6 yield (%) | 7 yield (%) |
|---|---|---|---|---|---|---|---|
| 1 | 5a | $C(O)CH_3$ | H | —$CH_2$— | 30 | >95 (6a) | 0 (7a) |
| $2^a$ | 5a | $C(O)CH_3$ | H | —$CH_2$— | 180 | >95 (6a) | 0 (7a) |
| 3 | 5b | $C(O)CH_3$ | p-Cl | —$CH_2$— | 200 | >95 (6b, 7-chloro) | 0 (7b) |
| $4^b$ | 5c | $C(O)CH_3$ | o-Cl | —$CH_2$— | 180 | 86 (6c, 5-chloro) | 0 (7c) |
| $5^b$ | 5d | $C(O)CH_3$ | m-Cl | —$CH_2$— | 180 | 79 (6d, 6d' 6-, 8- | 0 (7d) |
| 6 | 5e | C(O)Ph | H | —$CH_2$— | 90 | >95 (6e) | 0 (7e) |
| $7^c$ | 5f | $SO_2CH_3$ | H | —$CH_2$— | 20 | 76 (6f) | 0 (7f) |
| 8 | 5g | $SO_2Ph$ | p-Cl | —$CH_2$— | 15 | 89 (6g, 7-chloro) | 0 (7g) |
| 9 | 5h | SOPh | p-Cl | —$CH_2$— | 60 | 75 (6h, 7-chloro) | 0 (7h) |
| $10^c$ | 5i | $P(O)OEt_2$ | p-Cl | —$CH_2$— | 150 | >95 (6i, 7-chloro) | 0 (7i) |
| 11 | 5j | CHO | p-Cl | —$CH_2$— | 45 | 83 (6j, 7-chloro) | 0 (7j) |
| 12 | 5k | $CO_2CH_3$ | H | —$CH_2$— | 600 | 76 (6k) | 0 (7k) |
| $13^d$ | 5k | $CO_2CH_3$ | H | —$CH_2$— | 90 | >95 (6k) | 0 (7k) |
| $14^{a,b}$ | 5l | $C(O)CH_3$ | H | —$(CH_2)_2$— | 50 | >95 (6l) | 0 (7l) |
| $15^c$ | 5m | $C(O)CH_3$ | o-Cl | —$C(CO_2Et)_2$— | 30 | >95 (6m, 5-chloro) | 0 (7m) |
| 16 | 5n | $C(O)CH_3$ | H | —O— | 30 | 28 (6n) | 15 (7n) |
| 17 | 5o | $C(O)CH_3$ | H | —NTs— | 10 | 30 (6o) | 56 (7o) |
| $18^b$ | 5p | $C(O)CH_3$ | o-Cl | —NTs— | 10 | 24 (6p, 5-chloro) | 48 (7p) |
| $19^b$ | 5p | $C(O)CH_3$ | o-Cl | —NTs— | 10 | 59 (6p, 5-chloro) | 6 (7p) |

$^a$Reaction performed using 1,1,1-trifluorotoluene as solvent;
$^b$Reaction performed using o-dichlorobenzene (DCB) as solvent;
$^c$Reaction performed in DCB at 225° C.;
$^d$Reaction performed at 300° C. in DCB.

group on the aromatic ring also provided a 2:1 ratio of the dihydronaphthalene 7p to naphthalene 6p in 10 min in a combined yield of 72% (entry 18). If 5p was heated to 225° C. for 10 min, nearly a 10:1 ratio of naphthalene 7p to dihydronaphthalene 6p was obtained in 65% yield (entry 19). For each of the heteroatom-containing tethers a mixture of products was observed; furthermore, when the reaction time was extended to 120 min for entry 5p, the ratio of naphthalene 6p to internal standard did not change, but the dihydronaphthalene 7p was no longer evident by $^1$H NMR, suggesting that dihydronaphthalene 7p is not converted to 6p. Separation of dihydronaphthalene 7p and naphthalene 6p could not be accomplished by column chromatography, so attempts were made to oxidize the mixture to 6p using cerric ammonium nitrate (CAN), dichlorodicyanobenzoquinone (DDQ), Pd/C, or $O_2$. All reactions gave either complete decomposition of the naphthalene and dihydronaphthalene products, or selective decomposition of the dihydronaphthalene.

These naphthalene derivatives may be used as potential candidates for application to the ever-increasing field of small molecule fluorescent probes. Consequently, reaction of 6b to a palladium-catalyzed amination reaction using RuPhos precatalyst, LHMDS and N,N-dimethylamine afforded cyclopentanaphthalene 8 in 70% yield. Compound 8 was strongly fluorescent with an absorption maxima of 377 nm and an emission maxima of 510 nm. The emission maxima was significantly red-shifted from the structurally similar Prodan, which has an emission maxima of 440 nm in dichloroethane. Moreover, a quantum yield of 99% was measured for compound 8 in dichloroethane.

A thermal dehydrogenative Diels-Alder reaction affords cyclopenta-naphthalenes in excellent yield. For all cases examined, the styrene functioned only as a diene contrary to literature reports of competing reactivity. For the heteroatom-containing tether, dihydro-naphthalenes were obtained along with the naphthalene products. Investigations are underway to understand the mechanism by which these two products are formed. Finally, it has been demonstrated the synthetic utility of this method by preparing fluorophore 8 with interesting photophysical properties.

Prodan 8a is a compound whose fluorescent emission and quantum yield is unusually dependent upon solvent polarity; in cyclohexane the fluorescent emission is 410 nm and in water it is 534 nm, a bathochromic shift of 124 nm. Prodan is considered to be state of the art for application in biological systems and structural variants of this probe have been prepared, such as the lipophilic Laurdan 8b; the thiol reactive Acrylodan 8c and Badan 8d; and the amino acid-containing Aladan 8e. In addition, a spectrally red-shifted compound, Anthradan 8f, has been prepared that incorporates an anthracene ring between the electron donating and electron withdrawing groups; the emission spectra in hexanes is 483 nm, and in methanol 604 nm.

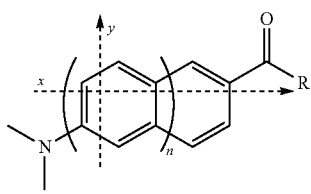

Prodan Derviatives
8a, R = $CH_2CH_3$, n = 1
8b, R = $(CH_2)_{10}CH_3$, n = 1
8c, R = $CHCH_2$, n = 1
8d, R = $CH_2Br$, n = 1
8e, R = $CH_2C(CO_2H)NHFmoc$, n = 1
8f, R = $CH_2CH_3$, n = 2

For each of these Prodan derivatives, the donor-acceptor substituents are located along the x-axis (longer axis) of the naphthalene pi-system, and the amino group can be characterized as exonuclear and sterically unhindered. For the anthracene analog, even though the emission wavelength was significantly red-shifted, the quantum efficiency was lower. The design and synthesis of new naphthalene-containing fluorophores could be significantly enhanced by novel methods for the construction of aromatic rings. As described herein, the synthesis and fluorescent properties of a series of novel Prodan derivatives, enabled by the microwave-assisted dehydrogenative Diels-Alder reaction, whereby the acceptor and/or donor substituents are located along the y-axis (shorter axis) of the conjugated system, providing a more rigid conjugated structure between the acceptor and donor groups.

With an eye towards the preparation of a series of aminonaphthalene derivatives, cross coupling reactions were examined for the introduction of electron donating amine groups via the chloronaphthalene. For this process, the versatile palladium-catalyzed amination of aryl halides has emerged as a valuable tool. For the first generation derivative, dimethylamine and chloronaphthalenes 6b, 6c, 6d and 6d' were selected so that photophysical properties of this first generation of derivatives could be directly compared to that of Prodan (Scheme 4). The coupling reaction of 6b and 6d using a commercially available RuPhos precatalyst (2.5 mol %) and LHMDS in dry THF afforded the corresponding N,N-dimethylamine substituted cyclopentanaphthalenes 10 and 12 in 70% and 49% yield, respectively. Different palladium sources (Pd(OAc)$_2$) and bases (K$_3$PO$_4$, CsCO$_3$) were also screened, but all resulted in lower yields of the coupling products. Interestingly, the inseparable mixture of 6d and 6d' gave two products: 11 in 52% yield along with 6a. It is hypothesized that 6a arises from a palladium catalyzed-dehalogenation reaction of 6d' facilitated by the close proximity of the methyl ketone. Next, a number of amines were coupled with 6b. Secondary cyclic amines such as pyrrole, piperidine, and morpholine gave the corresponding tertiary amines 13, 14, and 15 in 59%, 45% and 58% yield, respectively. Primary amines such as benzylamine, aniline, and para-methoxyaniline were also successfully coupled with 6b to afford 16, 17 and 18 in 89%, 78% and 71% yield, respectively.

Scheme 4. Palladium-catalyzed cross coupling reactions and photophysical properties of the amino-substituted naphthalenes

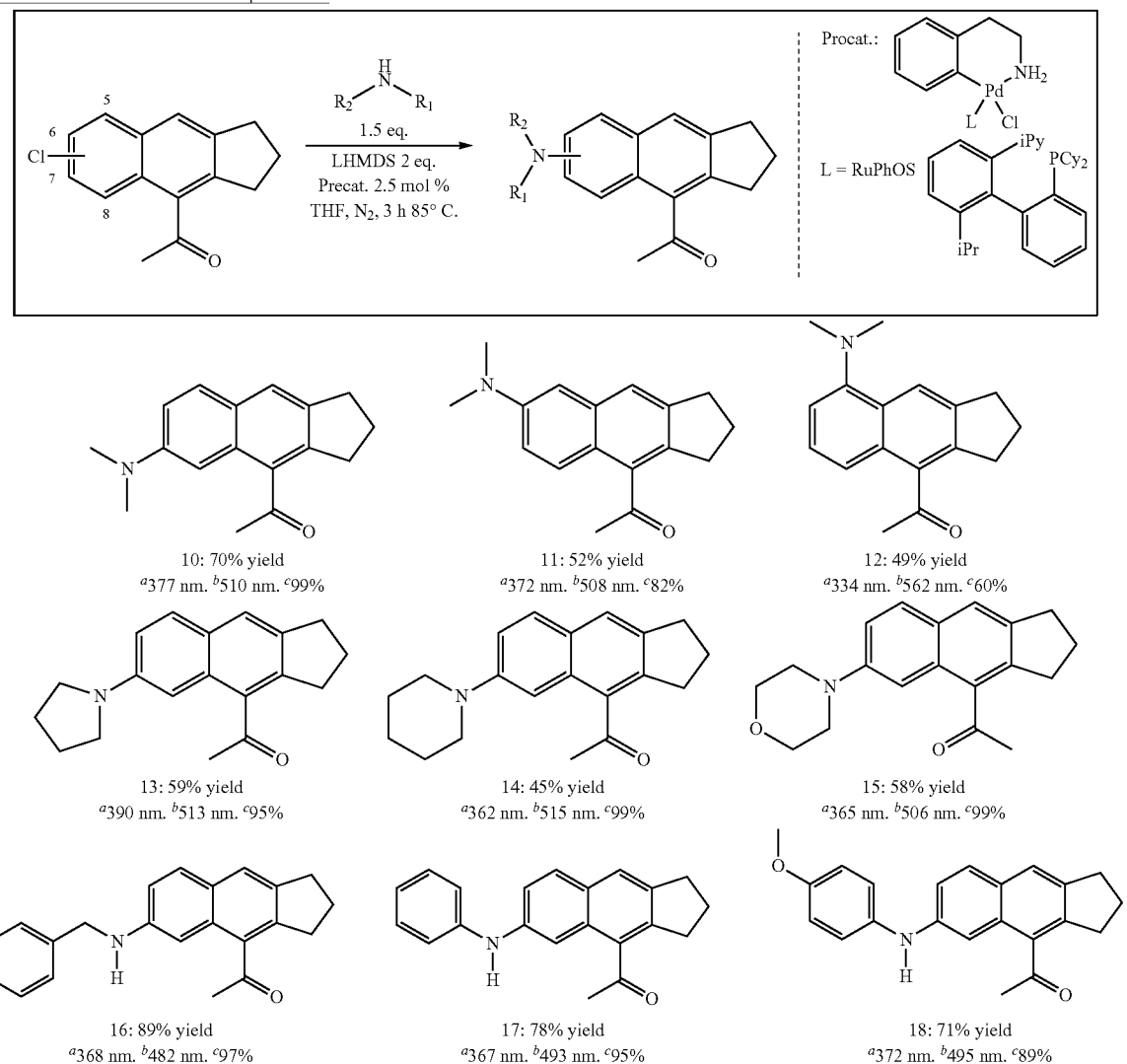

[a]Absorption maximum in $CH_2Cl_2$; [b]Emission maximum in $CH_2Cl_2$; [c]Fluorescence quantum yield vs Prodan in DMSO (91%).

With a series of compounds with the donor and acceptor groups separated by a naphthalene nucleus in hand, fluorescent absorption and emission maximum were measured in methylene chloride, along with quantum yields. Notable trends for this series of solvatochromic compounds were observed. Compound 12 containing a 1,5-substituted cyclopentanaphthalene moiety absorbed light at a much shorter wavelength (332 nm) and fluoresced at a much longer wavelength (562 nm) than either the 1,7- or 1,6-disubstituted compounds 10 or 11 (absorption and emission maximum ~375 nm and 510 nm). The tertiary cyclic amine series showed a range of absorption maxima (355-390 nm) while the emission maxima remained constant (508-515 nm). The emission spectra of the secondary amines 16, 17, and 18 were significantly blue-shifted (482-492 nm) when compared to the tertiary amines, but there were not significant differences in absorption or emission maxima between each of the secondary amines. Finally, the quantum yields for all fluorophores in Scheme 4 were extremely high, with one exception, compound 12.

Figure 2A:
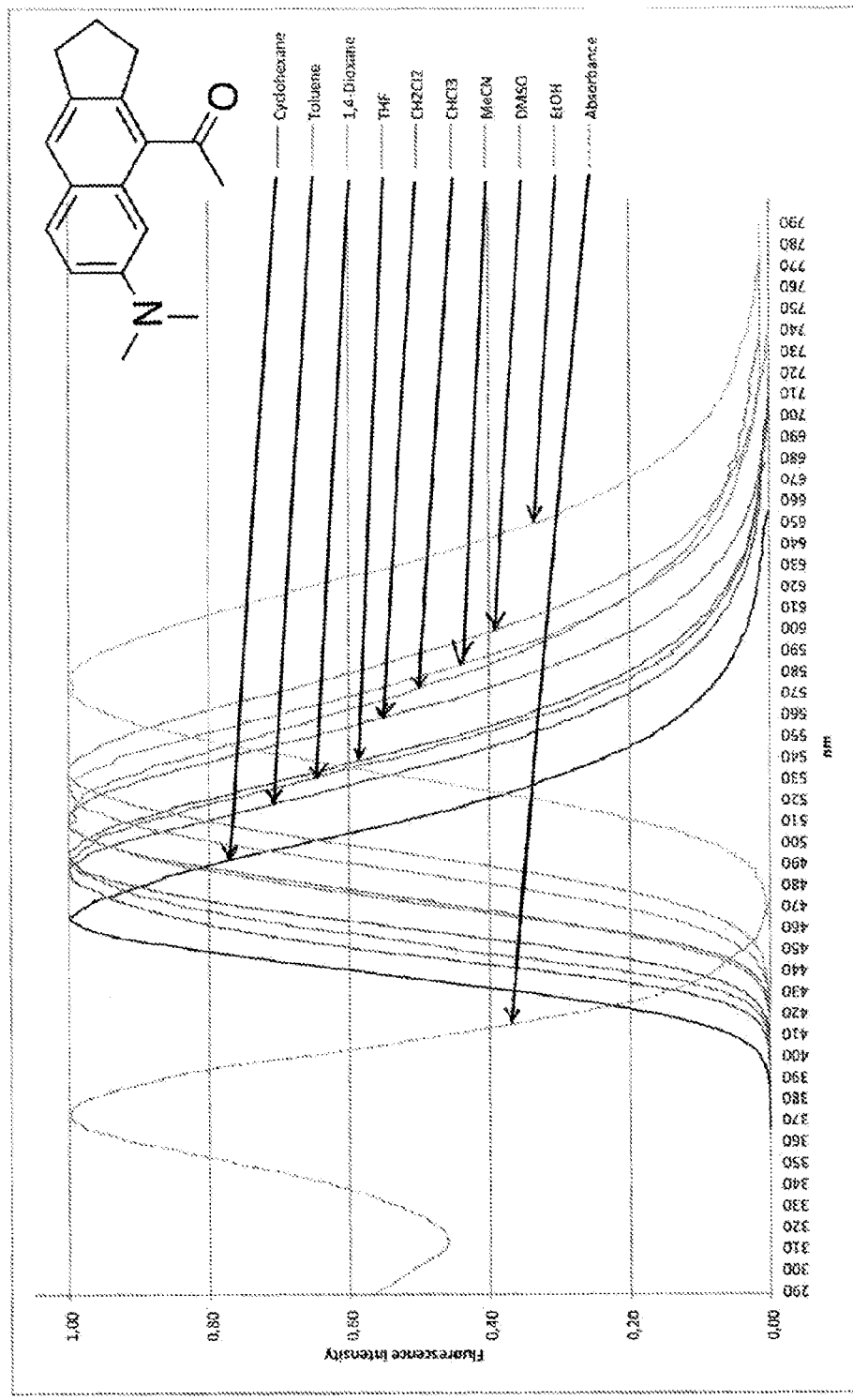
FIG. 2A is the absorption (dashed line) and fluorescent emission (solid lines) spectra of 1-(6-(dimethylamino)-2,3-dihydro-1H-cyclopenta[b]naphthalen-4-yl)ethanone in organic solvents of different polarity. Absorption spectrum was recorded in CH$_2$Cl$_2$. The excitation wavelength was 334 nm.
Figure 2B:
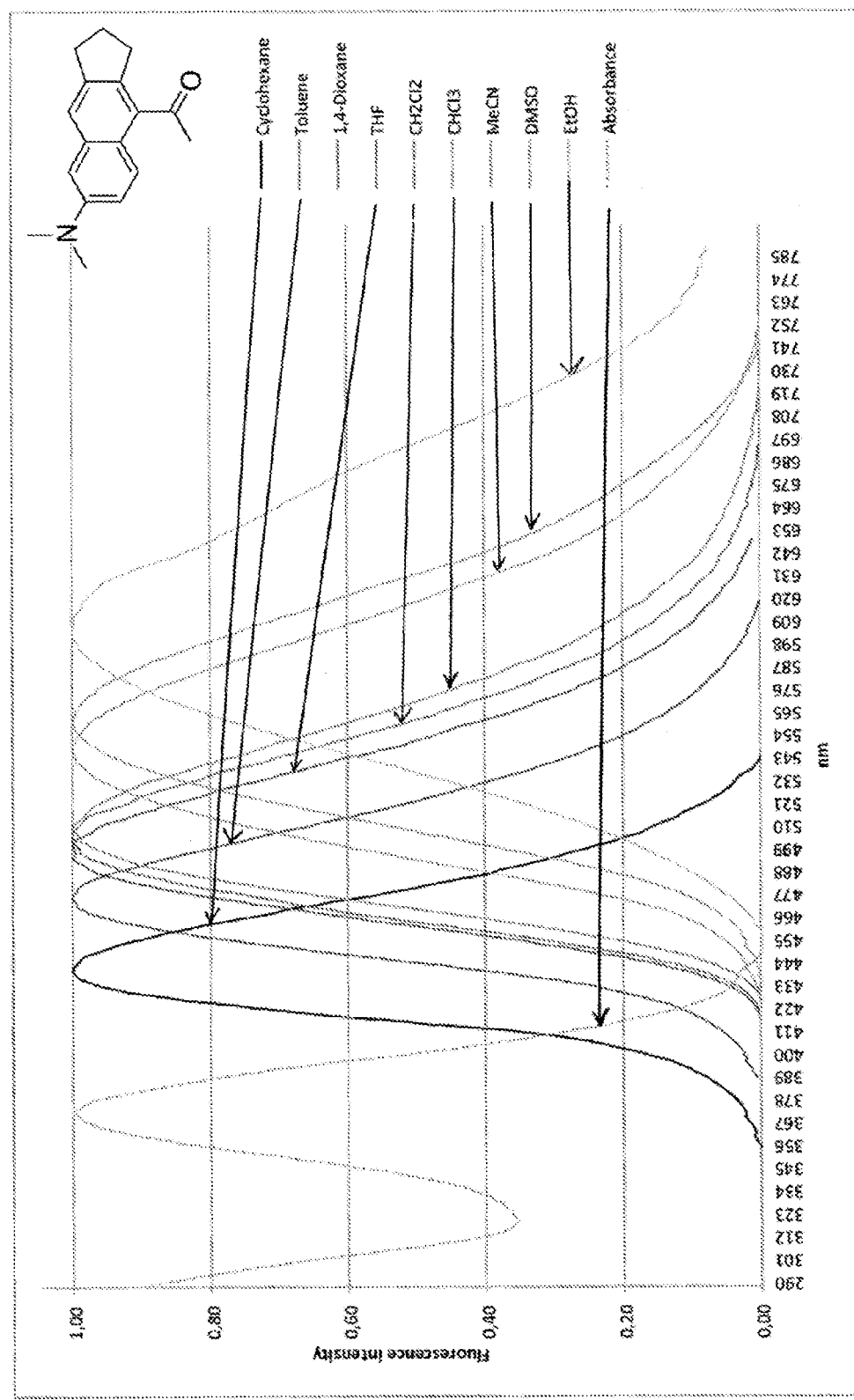
FIG. 2B is the absorption (dashed line) and fluorescent emission (solid lines) spectra of 1-(7-(dimethylamino)-2,3-dihydro-1H-cyclopenta[b]naphthalen-4-yl)ethanone in organic solvents of different polarity. Absorption spectrum was recorded in CH$_2$Cl$_2$. The excitation wavelength was 334 nm.
Figure 2C:
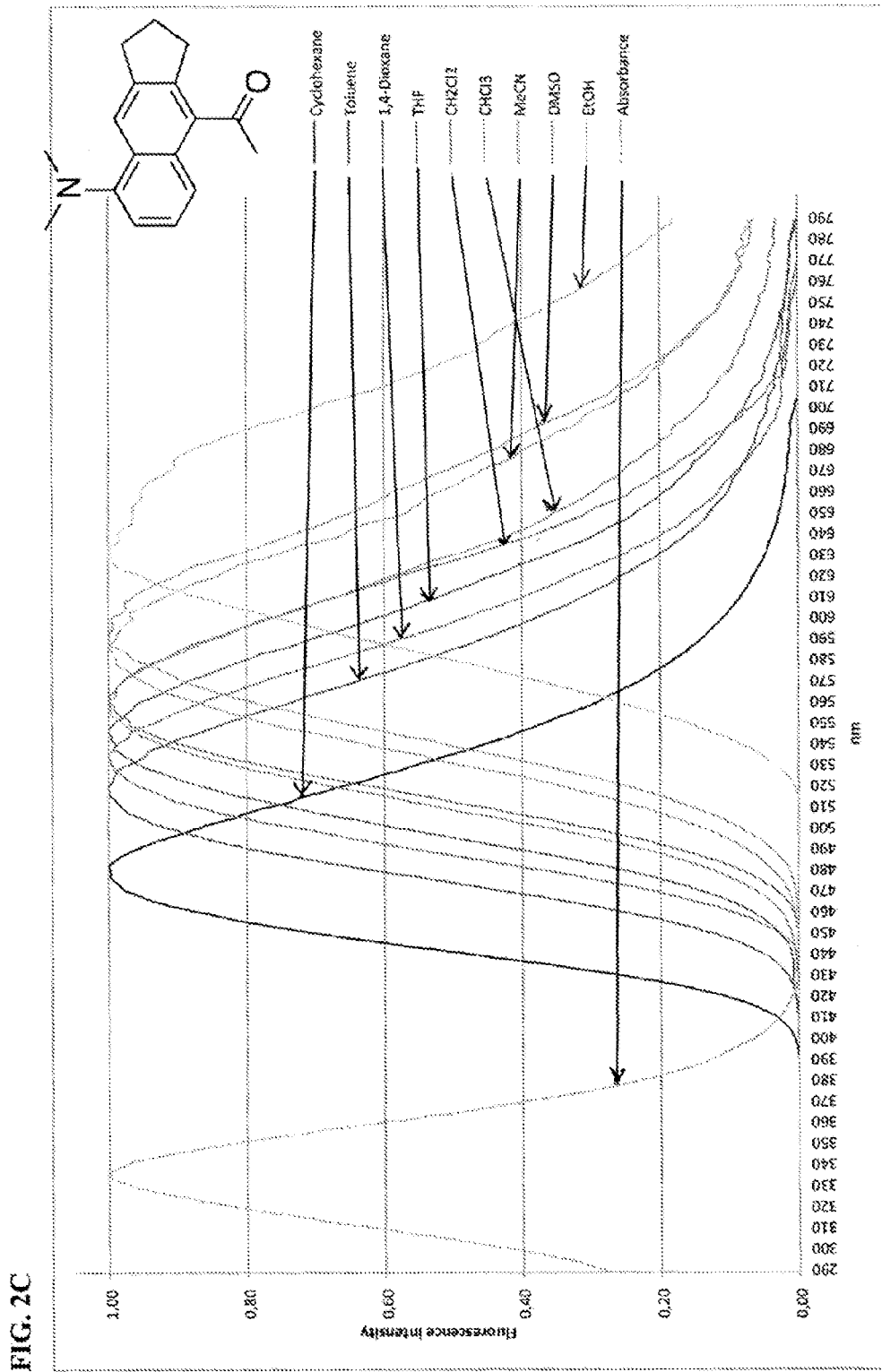
FIG. 2C is the absorption (dashed line) and fluorescent emission (solid lines) spectra of 1-(8-(dimethylamino)-2,3-dihydro-1H-cyclopenta[b]naphthalen-4-yl)ethanone in organic solvents of different polarity. Absorption spectrum was recorded in CH$_2$Cl$_2$. The excitation wavelength was 334 nm.
Figure 3E:
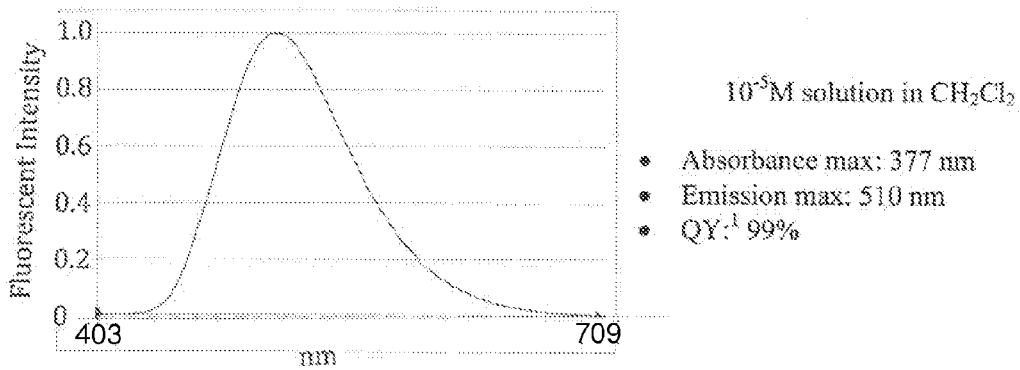
Figure 3F:
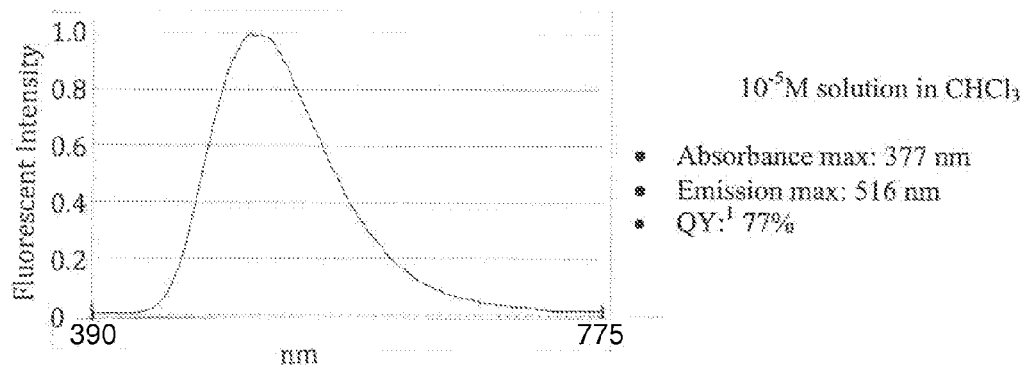
Figure 3G:
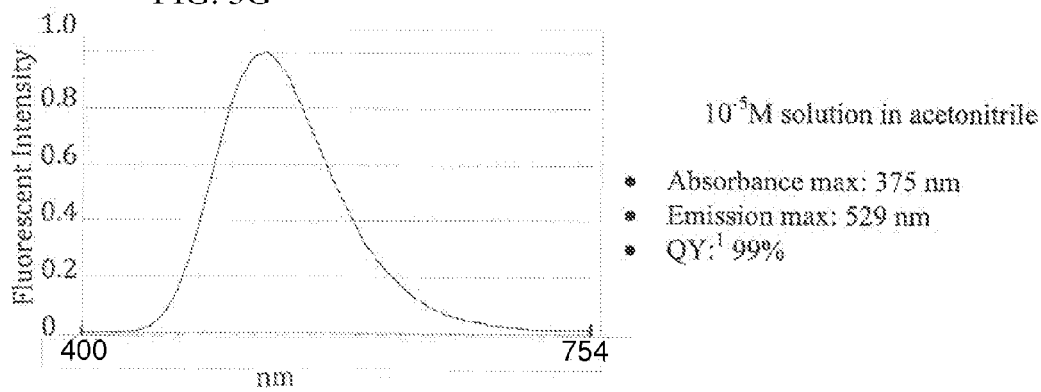
Figure 3H:
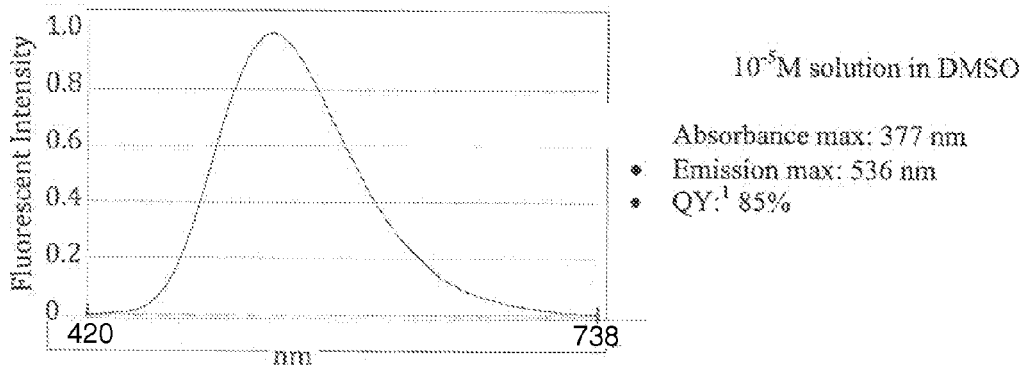
Figure 4C:
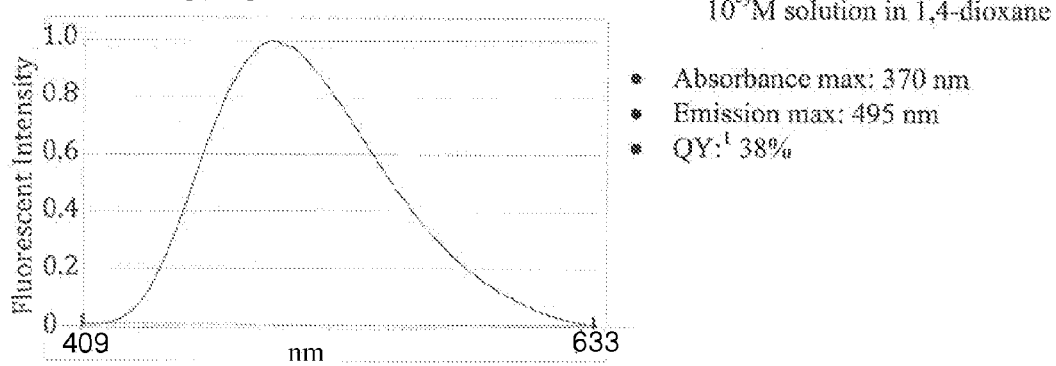
Figure 4D:
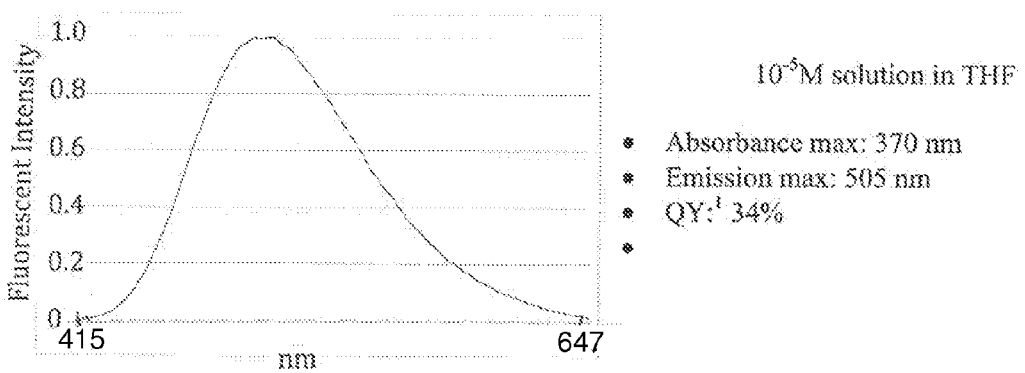
Figure 4E:
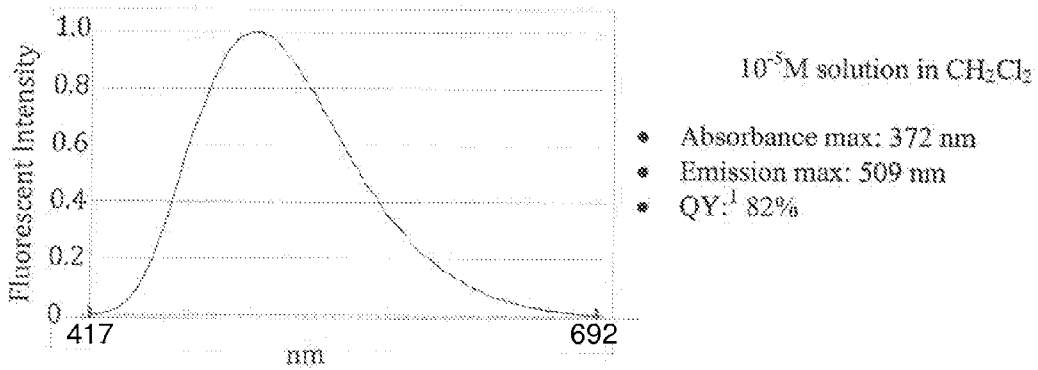
Figure 4F:
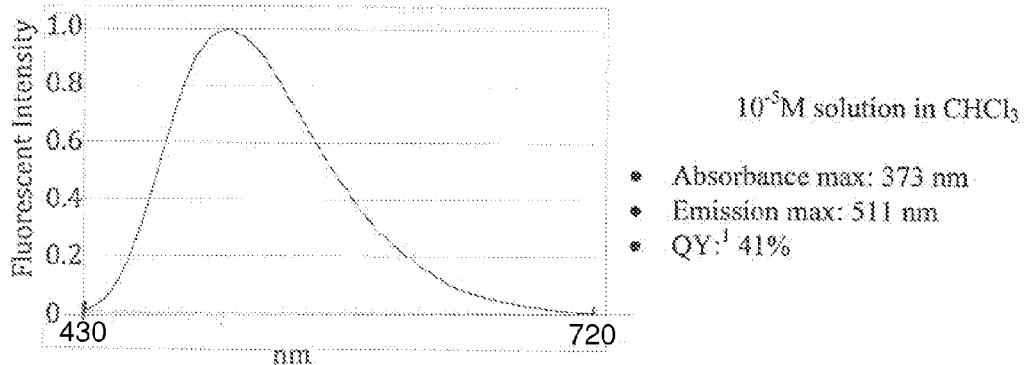
Figure 4G:
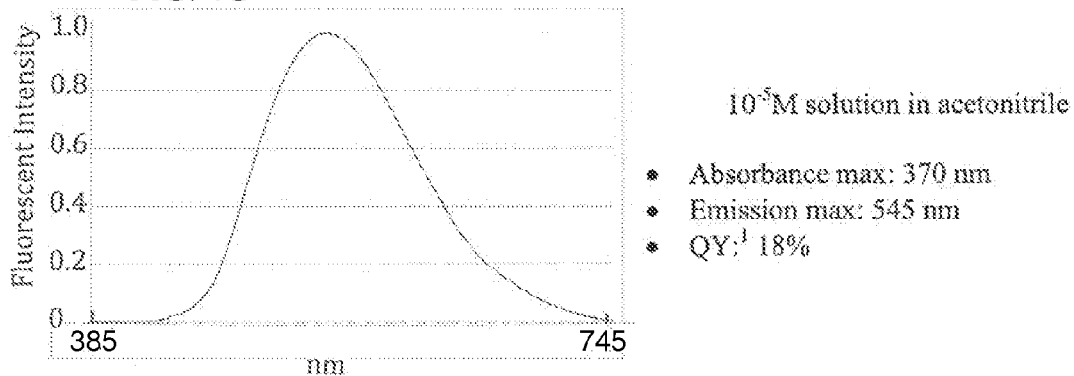
Figure 4H:
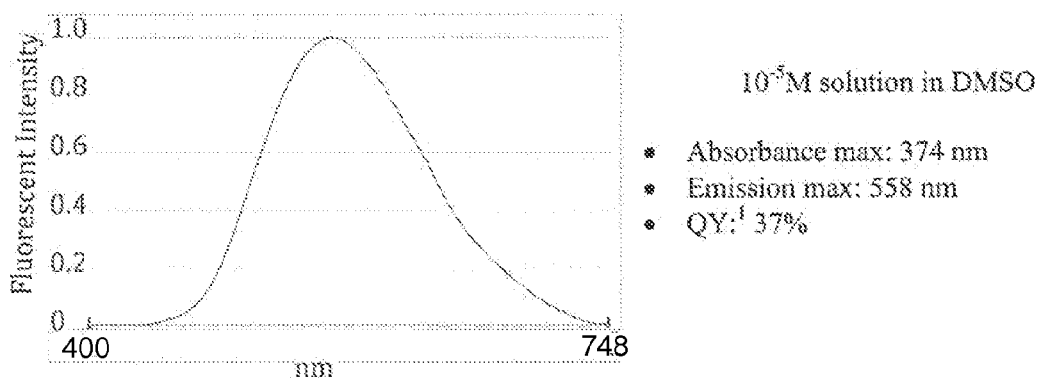
Figure 4I:
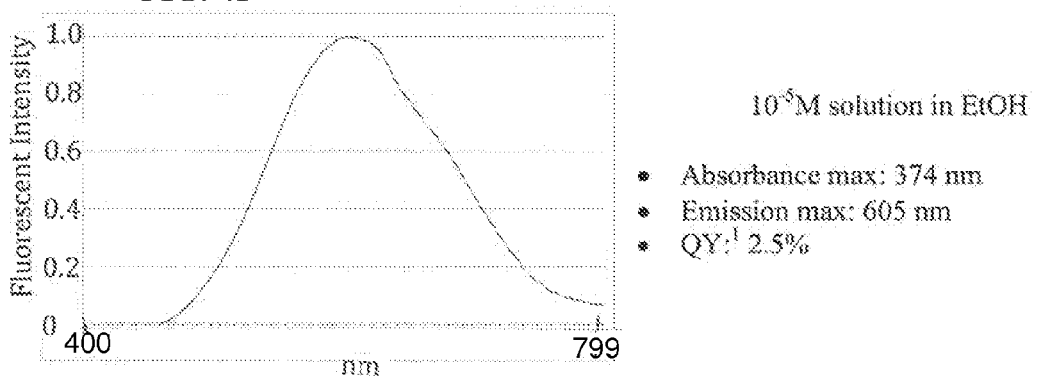
Figure 5E:
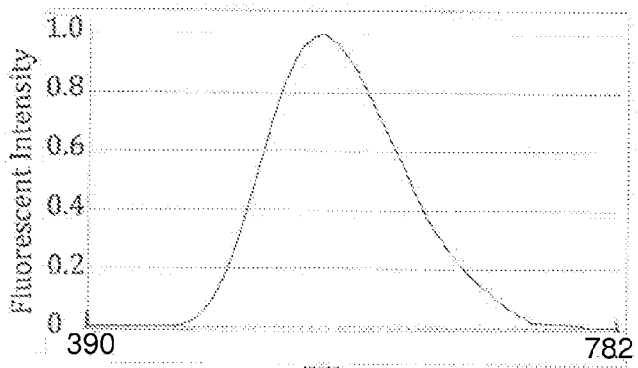
Figure 5F:
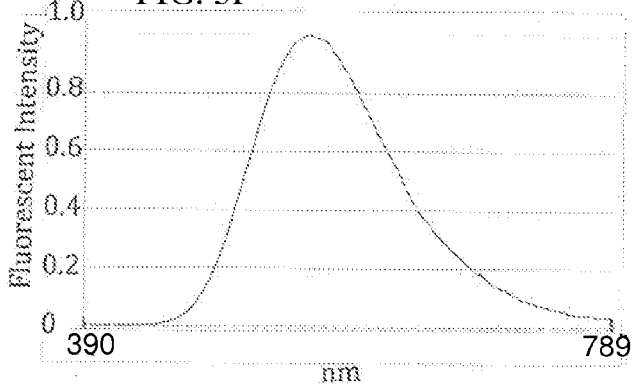
Figure 5G:
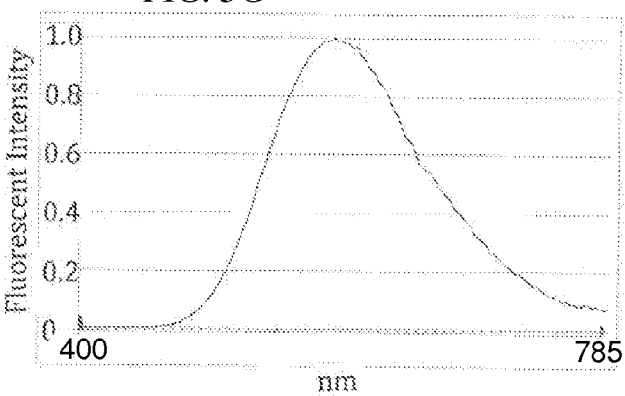
Figure 5H:
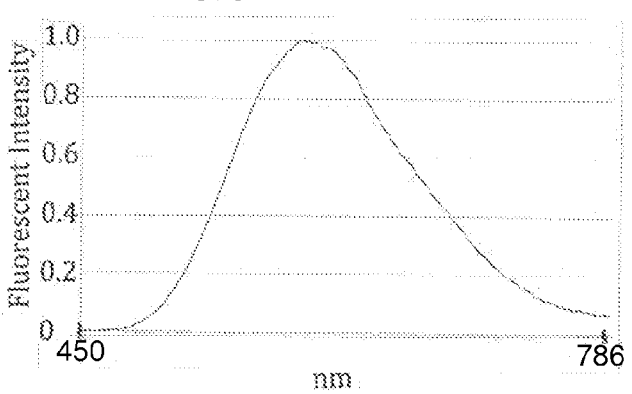
Figure 8:
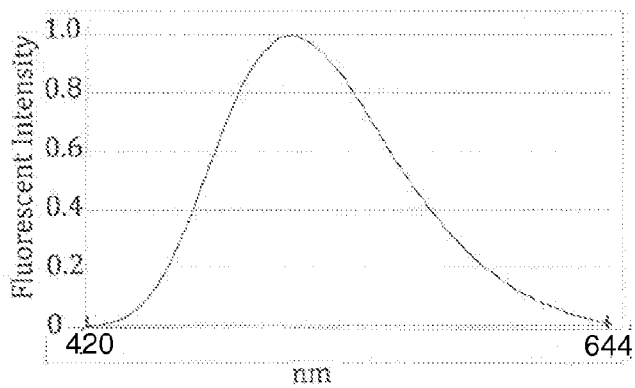
FIG. 8 shows the emission spectra for 1-(6-morpholino-2,3-dihydro-1H-cyclopenta[b]naphthalen-4-yl)ethanone, QY is fluorescence quantum yield vs PRODAN in DMSO (91%); excitation wavelength was 334 nm.
Figure 8:
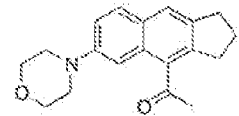
Figure 9:
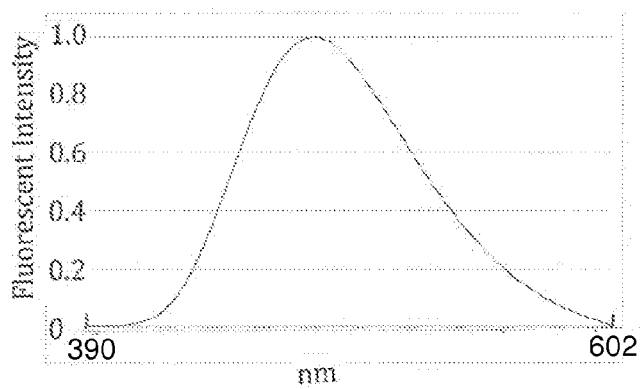
FIG. 9 shows the emission spectra for 1-(6-(benzylamino)-2,3-dihydro-1H-cyclopenta[b]naphthalen-4-yl)ethanone, QY is fluorescence quantum yield vs PRODAN in DMSO (91%); excitation wavelength was 334 nm.
Figure 9:
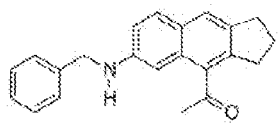
Figure 10:
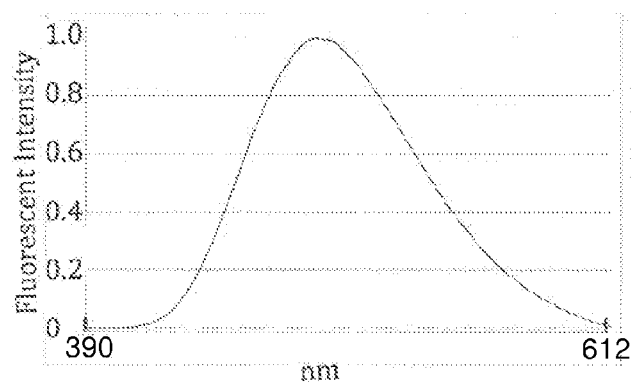
FIG. 10 shows the emission spectra for 1-(6-(phenylamino)-2,3-dihydro-1H-cyclopenta[b]naphthalen-4-yl)ethanone, QY is fluorescence quantum yield vs PRODAN in DMSO (91%); excitation wavelength was 334 nm.
Figure 10:
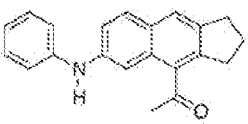
Figure 11:
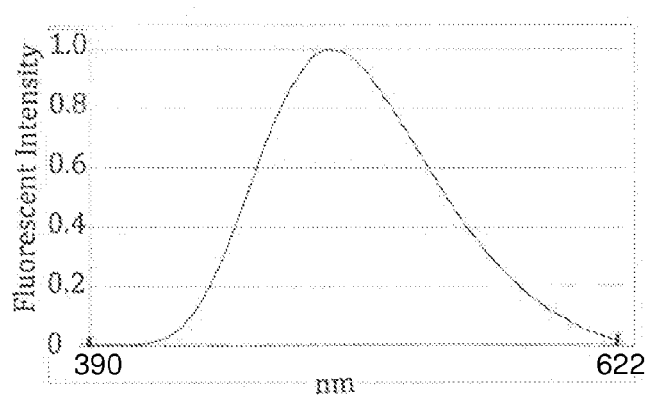
FIG. 11 shows the emission spectra for 1-(6-((4-methoxyphenyl)amino)-2,3-dihydro-1H-cyclopenta[b]naphthalen-4-yl) ethanone, QY is fluorescence quantum yield vs PRODAN in DMSO (91%); excitation wavelength was 334 nm.
Figure 11:
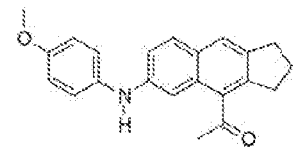

Finally, solvatochromic properties for compounds 10, 11, and 12 were measured in a number of solvents varying in polarity (FIG. 2). Several important findings emerged from these measurements, the first being that in the case of all fluorophores, as the solvent polarity increases the emission maxima are significantly red-shifted. For example, the emission maxima for compounds 10, 11, and 12 are 466, 445 and 480 nm in cyclohexane and 578, 605, and 634 nm in ethanol, respectively. Moreover, the emission spectra are significantly red-shifted from that of Prodan, which emits at 389 nm in hexanes and 485 nm in ethanol. Red-shifted fluorescent emissions are important for biological applications where background fluorescence can limit the magnitude of the fluorescent change.

TABLE 2

Spectroscopic properties of dyes 10, 11 and 12 in comparison to Prodan

| | | Prodan | | | 12 | | | 11 | | | 10 | | |
|---|---|---|---|---|---|---|---|---|---|---|---|---|---|
| Entry | Solvent | $\lambda_{abs}^a$ nm | $\lambda_{em}^b$ nm | QY % | $\lambda_{abs}^a$ nm | $\lambda_{em}^b$ nm | $QY^c$ % | $\lambda_{abs}^a$ nm | $\lambda_{em}^b$ nm | $QY^c$ % | $\lambda_{abs}^a$ nm | $\lambda_{em}^b$ nm | $QY^c$ % |
| 1 | n-Hexane | 340 | 389 | 2.0 | / | / | / | / | / | / | / | / | / |
| 2 | Cyclohexane | / | / | / | 314 | 480 | 28 | 363 | 445 | 8 | 373 | 466 | 45 |
| 3 | Toluene | 346 | 416 | 56 | 322 | 520 | 47 | 368 | 481 | 25 | 376 | 490 | 62 |
| 4 | 1,4-Dioxane | 346 | 422 | 75 | 319 | 534 | 44 | | | | 376 | 495 | 46 |
| 5 | THF | 348 | 430 | 78 | 330 | 543 | 39 | 370 | 505 | 34 | 377 | 497 | 75 |
| 6 | CH$_2$Cl$_2$ | 355 | 440 | 98 | 334 | 562 | 60 | 372 | 509 | 82 | 377 | 510 | 99 |
| 7 | CHCl$_3$ | / | / | / | 334 | 562 | 40 | 373 | 514 | 41 | 377 | 516 | 77 |
| 8 | Acetonitrile | 350 | 455 | 80 | 316 | 590 | 23 | 370 | 545 | 18 | 375 | 529 | 99 |
| 9 | DMSO | 357 | 462 | 91 | 334 | 598 | 48 | 374 | 558 | 37 | 377 | 536 | 85 |
| 10 | EtOH | 362 | 485 | 71 | 334 | 634 | / | 374 | 605 | 3 | 377 | 578 | 5 |

[a]Maximum absorption.
[b]Maximum emission.
[c]Fluorescence quantum yield vs Prodan in DMSO (91%), excitation was 334 nm (10$^{-5}$M solutions).

According to specific embodiments, the substituted, functionalized naphthalenes synthesized by the methods of the present disclosure may have a molecular structure according to Formula I.

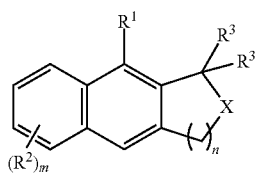

I

According to Formula I, R$^1$ may be a substituent selected from the group consisting of H, C$_1$-C$_{20}$ alkyl, C$_1$-C$_{20}$ alkoxy, phenyl, aryl, heteroaryl, —S(O)R$^4$, —S(O)$_2$R$^4$, P(O)(OR$^4$)$_2$, and —C(Y)R$^4$ where Y is O, NR$^5$, or S; each R$^2$ may be a halogen or an electron donating group selected from —N(R$^6$)$_2$, —OR$^6$, and —SR$^6$; each R$^3$ may be H, C$_1$-C$_{20}$ alkyl, or combined as =O; each R$^4$, R$^5$ and R$^6$ may be independently selected from H, C$_1$-C$_{20}$ alkyl, C$_1$-C$_{20}$ alkoxy, phenyl, aryl, heteroaryl or may come together to form a cyclic structure; X is CH$_2$, C(R$^6$)$_2$, C(CO$_2$Alkyl)$_2$, O, NTs, NH, NCOR$^5$ or NR$^5$; n is an integer from 0 to 2; m is an integer from 1 to 4. According to certain embodiments, suitable fluorescence may be observed when one of R$^1$ or R$^3$ has a pi bond that is in conjugation with the pi system of the naphthalene ring. Therefore, according to the naphthalenes of the present disclosure, at least one of R$^1$ and R$^3$ will comprise a pi bond in conjugation with the pi system of the naphthalene ring, i.e., provided that either R$^1$ is one of —S(O)R$^4$, —S(O)$_2$R$^4$, P(O)(OR$^4$)$_2$, and —C(Y)R$^4$ and/or R$^3$ is =O. The R$^2$ group in the various embodiments may further be selected from Cl, C$_1$-C$_{20}$ alkyl groups or phenyl, aryl, or heteroaryl groups when more than one R$^2$ group is present provided that at least one R$^2$ group is an electron donating group. Other electron donating groups that may be suited as R$^2$ such as groups with an atom having a lone pair of electrons that is attached either directly to the carbon of the naphthalene ring or attached indirectly to a carbon of the naphthalene ring by a pi system that is in conjugation with the pi system of the naphthalene. Examples include heteroaromatic groups, phenyl or aromatic groups with a conjugated electron donating group.

The structure according to Formula I, may further comprise substitution on the carbons of the naphthalene ring, or on the carbons of the non-aromatic ring, such as the cyclopentyl ring (where n=1). For example, according to certain embodiments, the naphthalene ring may be substituted on two adjacent carbons with at least one carbocyclic or heterocyclic ring fused to the naphthalene ring. In specific embodiments, the fused ring may be at least one aromatic ring or a heteroaromatic ring. For example, according to certain embodiments the naphthalene ring may have a phenyl ring(s) fused to the naphthalene ring, thereby making an anthracenyl-type ring system, a phenanthracenyl-type ring system. The ring(s) fused to the naphthalene rings may be substituted with various substituents, such as the ones described herein, and including electron withdrawing or electron donating groups (such as R$^2$-type groups). Without intending to be limited by any interpretation, it is believed that changing the substitution and/or extending the pi system of the naphthalene system may be used to tune the optical properties of the compound, such as the fluorescent properties.

In specific embodiments, R$^1$ may be —S(O)R$^4$, —S(O)$_2$R$^4$, P(O)(OR$^4$)$_2$, or —C(Y)R$^4$, Y may be O or NR$^5$ and R$^4$ and R$^5$ may independently be H, C$_1$-C$_{20}$ alkyl, C$_1$-C$_{20}$ alkoxy, phenyl, or aryl, and each R$^2$ is Cl, —N(R$^6$)$_2$, or —OR$^6$, where each R$^6$ may be H, C$_1$-C$_{20}$ alkyl, substituted or unsubstituted phenyl, or come together to form a cyclyl or heterocyclyl structure having 4-5 carbon atoms. According to particular embodiments, $R^1$ may —C(Y)$R^4$, Y is O, and $R^4$ may be H, $C_1$-$C_{20}$ alkyl, $C_1$-$C_{20}$ alkoxy, phenyl, or aryl.

In still other embodiments of the functionalized naphthalenes described herein, wherein $R^2$ may be Cl, such as in the product of the dehydrogenative dihydro Diels Alder reaction, or alternatively, in the resulting fluorescent compound. In other embodiments, at least one $R^2$ may be an electron donating group, such as, —N($R^6$)$_2$, or —O$R^6$, where each $R^6$ may be H, $C_1$-$C_{20}$ alkyl, substituted or unsubstituted phenyl, or come together to form a cyclyl or heterocyclyl structure having 4-5 carbon atoms. According to these embodiments, specific fluorescent properties, such as solvatochromic properties, may be observed with these substituted functionalized naphthalenes.

According to other embodiments, the $R^3$ groups may together form a carbonyl group (C=O). According to these embodiments, the $R^1$ group need not be in conjugation with the naphthalene ring in order to observe fluorescence. In specific embodiments, where the $R^3$ groups are combined as a carbonyl (C=O), the X group may be $CH_2$ (i.e., a cyclic ketone), C($R^6$)$_2$ (i.e., a cyclic ketone), O (a lactone), or NTs (an amide), $R^1$ may be any of the groups described herein and in specific embodiments may be H, $C_1$-$C_{20}$ alkyl, $C_1$-$C_{20}$ alkoxy, phenyl, aryl, or heteroaryl, and each $R^2$ may be Cl, or an electron donating group such as —N($R^6$)$_2$, or —O$R^6$, where each $R^6$ is H, $C_1$-$C_{20}$ alkyl, substituted or unsubstituted phenyl, or come together to form a cyclyl or heterocyclyl structure having 4-5 carbon atoms. As used herein the term "cyclyl" means a cyclic group where the two $R^6$ groups on the nitrogen come together to from a four, five, six or seven membered ring including 3-6 substituted or unsubstituted carbon atoms and the nitrogen of the electron donating group. As used herein the term "heterocyclyl" means a heterocyclic group where the two $R^6$ groups on the nitrogen come together to from a four, five, six or seven membered ring including 2-5 substituted or unsubstituted carbon atoms, at least one second heteroatom such as an O, N, P, or S, and the nitrogen of the electron donating group.

According to specific embodiments, the substituted functionalized naphthalenes of the present disclosure may have a structure:

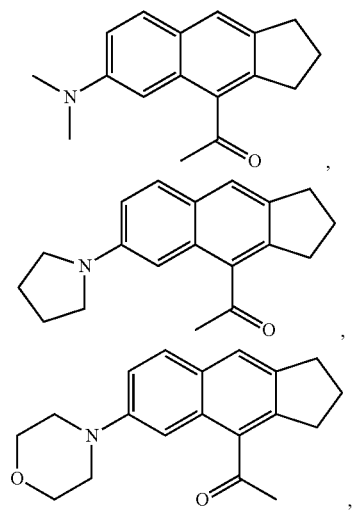

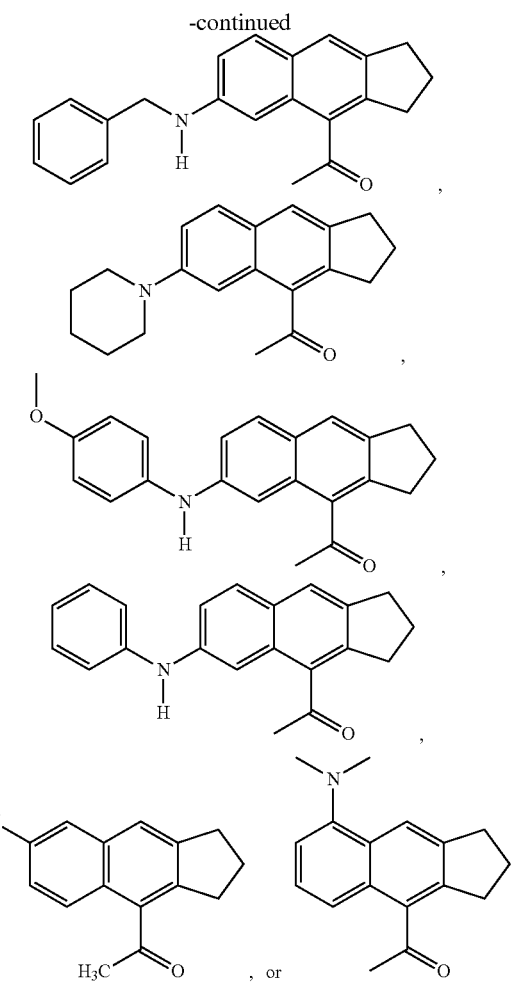

As described in detail herein, the substituted functionalized naphthalenes of the present disclosure, such as the naphthalenes according to Formula I, may be a fluorophore. That is, the substituted functionalized naphthalenes may absorb electromagnetic radiation at a short wavelength, such as a wavelength in the visible or UV region of the electromagnetic spectrum and emit or fluoresce light having a longer wavelength than the absorption wavelength. In particular embodiments, the fluorescent naphthalenes described herein may display a fluorescent emission maximum at a wavelength of from 450 nm to 650 nm. Emissions in these wavelengths may be of particular interest since many conventional fluorophores do not emit near the red end of the spectrum. The red shift observed for the present fluorophores make them potentially useful in a number of applications such as an imaging fluorescent agent, a tagging fluorescent agent, an ultimately use in medical diagnostics.

In specific embodiments, the various substituted functionalized naphthalenes of the present disclosure may be solvatochromic fluorophores. Solvatochromic fluorophores display different fluorescent properties, such as emission maxima, absorption maxima, quantum yields, depending on the solvents that they are dissolved or suspended in. Solvatochromism may allow the fluorescent species, such as a tagged compound, metabolite, cellular component, environmental contaminant etc., to be traced as it migrates from one solvated environment to another, for example by monitoring the fluorescent emission maximum of the fluorescent species. Conventional solvatochromic fluorophores, such as Prodan, may be limited because of their short wavelength emission maximum which can overlap with emission wavelength of other system components. In contrast, the solvatochromic fluorescent naphthalenes of the present disclosure may display a fluorescent emission maximum as wavelengths at least 50 nm longer than the fluorescent emission maximum of Prodan in the same solvent, and in certain embodiments up to 200 nm longer than the emission maximum of Prodan in the same solvent. Thus, the solvatochromic naphthalenes may display desired fluorescent properties not present in conventional sovlatochromic fluorophores.

Due to the relatively planar and rigid structure of the functionalized naphthalenes of the present disclosure, combined with their light absorption and emission properties, in certain embodiments the functionalized naphthalenes may be used as a liquid crystal.

Still further embodiments of the present disclosure provide methods for synthesizing the fluorescent functionalized naphthalenes described herein. According to the various embodiments, the methods comprise reacting a 2'-alkynyl substituted halostyrene by a dehydrogenative intramolecular dehydro Diels Alder reaction in the presence of microwave irradiation to form a halo substituted naphthalene; and reacting the halo substituted naphthalene to a cross coupling reaction to form a functionalized naphthalene having a structure according to Formula I,

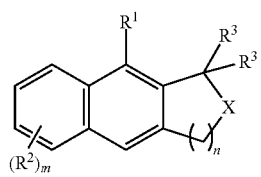

where $R^1$ is a substituent selected from the group consisting of H, $C_1$-$C_{20}$ alkyl, $C_1$-$C_{20}$ alkoxy, phenyl, aryl, heteroaryl, —S(O)$R^4$, —S(O)$_2R^4$, P(O)(O$R^4$)$_2$, and —C(Y)$R^4$ where Y is O, N$R^5$, or S; each $R^2$ is a halogen or an electron donating group selected from —N($R^6$)$_2$, —O$R^6$, and —S$R^6$; each $R^3$ is H, $C_1$-$C_{20}$ alkyl, or combined as =O; each $R^4$, $R^5$ and $R^6$ is independently selected from H, $C_1$-$C_{20}$ alkyl, $C_1$-$C_{20}$ alkoxy, substituted or unsubstituted phenyl, aryl, heteroaryl, benzyl, or may come together to form a cyclic structure; X is CH$_2$, C($R^6$)$_2$, C(CO$_2$Alkyl)$_2$, O, NTs, NH, NCO$R^5$ or N$R^5$; n is an integer from 0 to 2; m is an integer from 1 to 4, provided that either $R^1$ is one of —S(O)$R^4$, —S(O)$_2R^4$, P(O)(O$R^4$)$_2$, and —C(Y)$R^4$ or the $R^3$ groups are combined as =O. In these embodiments, the 2' alkynyl substituted halostyrene may have a structure as shown herein, for example where the alkyl may be substituted, the tether between the styryl double bond and the alkyne may have substitution and functionality (such as a carbonyl, ether, amine, amide, gem-diester, or alkyl substitution), and the aromatic ring may be substituted with a chlorine or a variety of other groups represented by $R^2$. As described herein the cross coupling reaction converts the halogen on the halo substituted naphthalene to an electron donating group, such as a group selected from —N($R^6$)$_2$, —O$R^6$, and —S$R^6$. Examples of cross coupling reactions include transition metal mediated cross coupling reactions, such as a palladium catalyst in the Buchwald-Hartwig reaction.

According to various embodiments of the described methods, the functionalized naphthalenes may have a structure where $R^1$ is —S(O)$R^4$, —S(O)$_2R^4$, P(O)(O$R^4$)$_2$, or —C(Y)$R^4$, Y is O or N$R^5$ and $R^4$ and $R^5$ are independently H, $C_1$-$C_{20}$ alkyl, $C_1$-$C_{20}$ alkoxy, phenyl, or aryl, and each $R^2$ is Cl, —N($R^6$)$_2$, or —O$R^6$, where each $R^6$ is H, $C_1$-$C_{20}$ alkyl, substituted or unsubstituted phenyl, or come together to form a cyclyl or heterocyclyl structure having 4-5 carbon atoms. According to specific embodiments of the methods, the functionalized naphthalene may have a structure

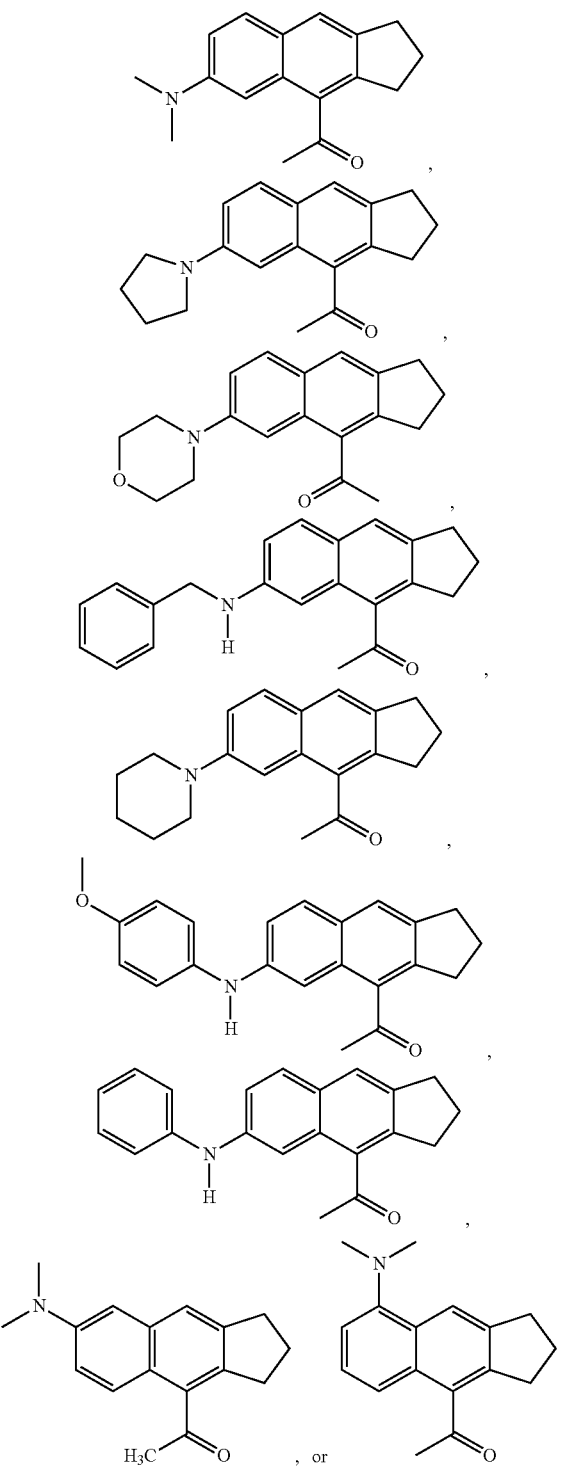

According to still other embodiments, the present disclosure provides methods for fluorescing a fluorescent functionalized naphthalene having a structure according to any of the embodiments described herein. For example, the functionalized naphthalene may have a structure

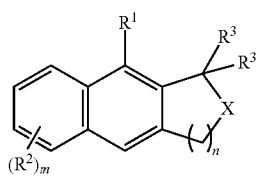

where $R^1$ is a substituent selected from the group consisting of H, $C_1$-$C_{20}$ alkyl, $C_1$-$C_{20}$ alkoxy, phenyl, aryl, heteroaryl, —S(O)$R^4$, —S(O)$_2R^4$, P(O)(O$R^4$)$_2$, and —C(Y)$R^4$ where Y is O, N$R^5$, or S; each $R^2$ is a halogen or an electron donating group selected from —N($R^6$)$_2$, —O$R^6$, and —S$R^6$; each $R^3$ is H, $C_1$-$C_{20}$ alkyl, or combined as =O; each $R^4$, $R^5$ and $R^6$ is independently selected from H, $C_1$-$C_{20}$ alkyl, $C_1$-$C_{20}$ alkoxy, substituted or unsubstituted phenyl, aryl, heteroaryl, benzyl, or may come together to form a cyclic structure; X is CH$_2$, C($R^6$)$_2$, C(CO$_2$Alkyl)$_2$, O, NTs, NH, NCO$R^5$ or N$R^5$; n is an integer from 0 to 2; m is an integer from 1 to 4, provided that either $R^1$ is one of —S(O)$R^4$, —S(O)$_2R^4$, P(O)(O$R^4$)$_2$, and —C(Y)$R^4$ or the $R^3$ groups are combined as =O. According to the various embodiments of these methods, the method may comprise the steps of irradiating the functionalized naphthalene with electromagnetic radiation and measuring the amount of fluorescent light emitted by the irradiated functionalized naphthalene. In specific embodiments the fluorescent light emitted by the irradiated functionalized naphthalene may have a emission maximum at a wavelength from 450 nm to 650 nm.

In still other embodiments, the functionalized, substituted naphthalenes of the present disclosure may have a structure where the naphthalene has a group(s) attached either directly or indirectly, for example, via a tether, that is capable of forming a bond with another molecule or substrate. The bond may be a covalent bond or an ionic bond. According to these embodiments, the other molecule or substrate may be "tagged" with the functionalized naphthalene. For example, according to embodiments where the functionalized naphthalene has fluorescent properties, the naphthalene may act as a fluorescent tag, wherein the tagged substrate or molecule fluoresces at a wavelength determined by the presence of the tagging functionalized naphthalene. The tagging naphthalenes may be used to tag various substrates, such as organic compounds, inorganic compounds, proteins, enzymes, nucleic acids, other cellular components and the like. According to specific embodiments, functionalized naphthalenes having a group capable of forming a bond with another substrate may include a carboxylic acid, ester, amide, diol, triazole, thiol, or other known tagging functional groups. Non-limiting examples of substituted naphthalene structures that have a functional group capable of tagging are illustrated in Scheme 5.

Scheme 5:
Naphthalenes that can act as fluorescent tags-synthesis

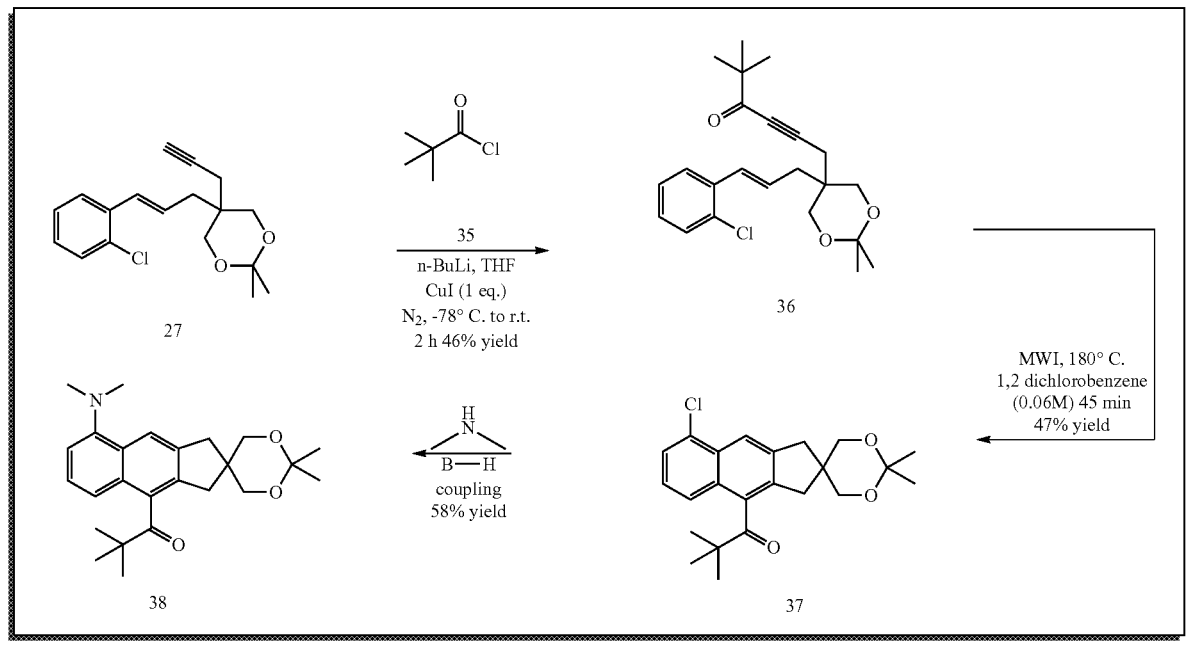

-continued
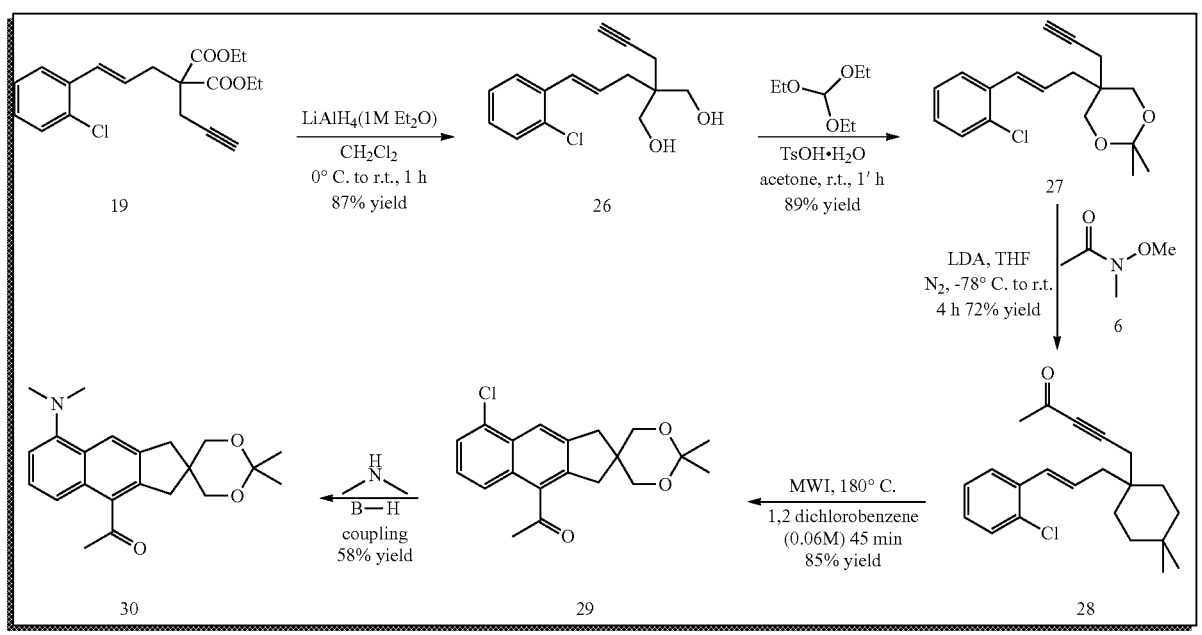
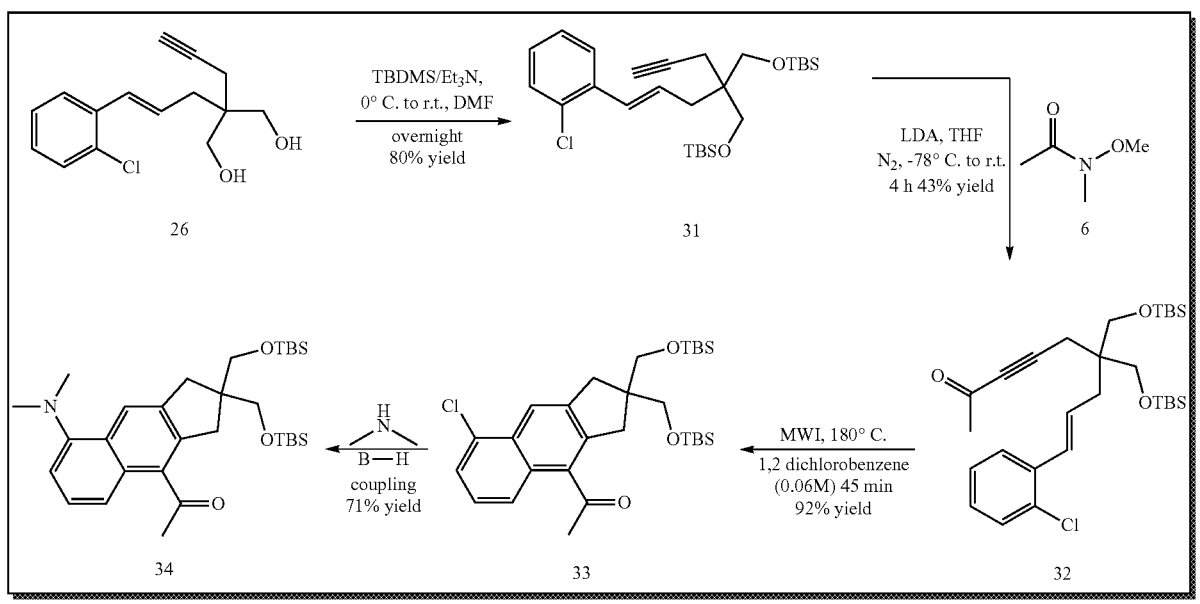

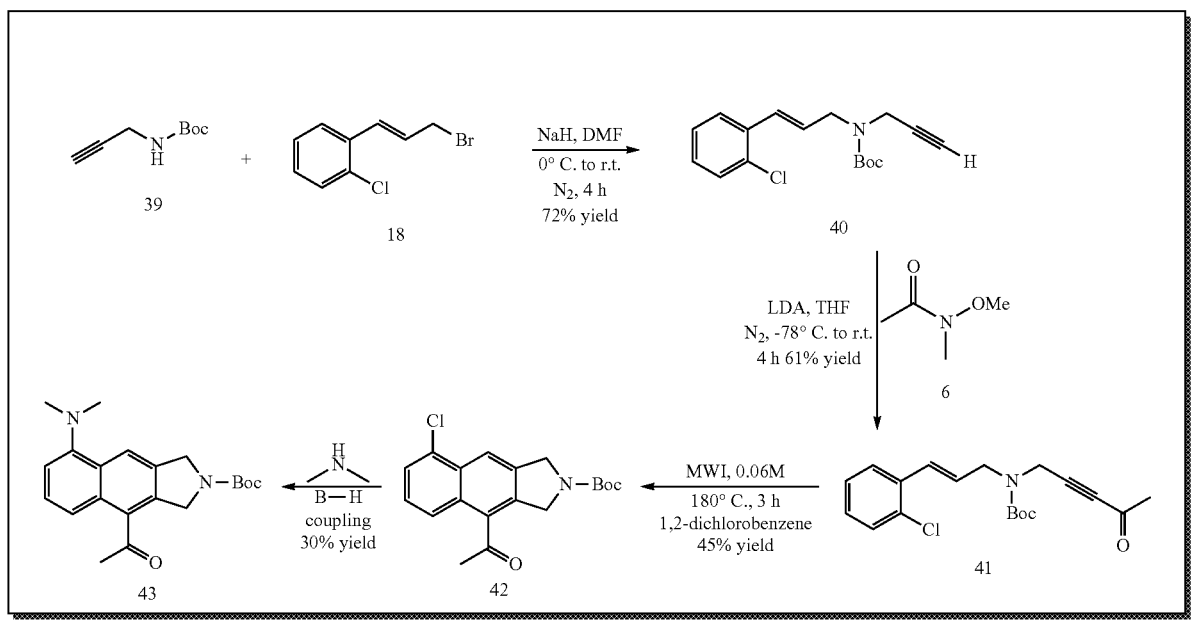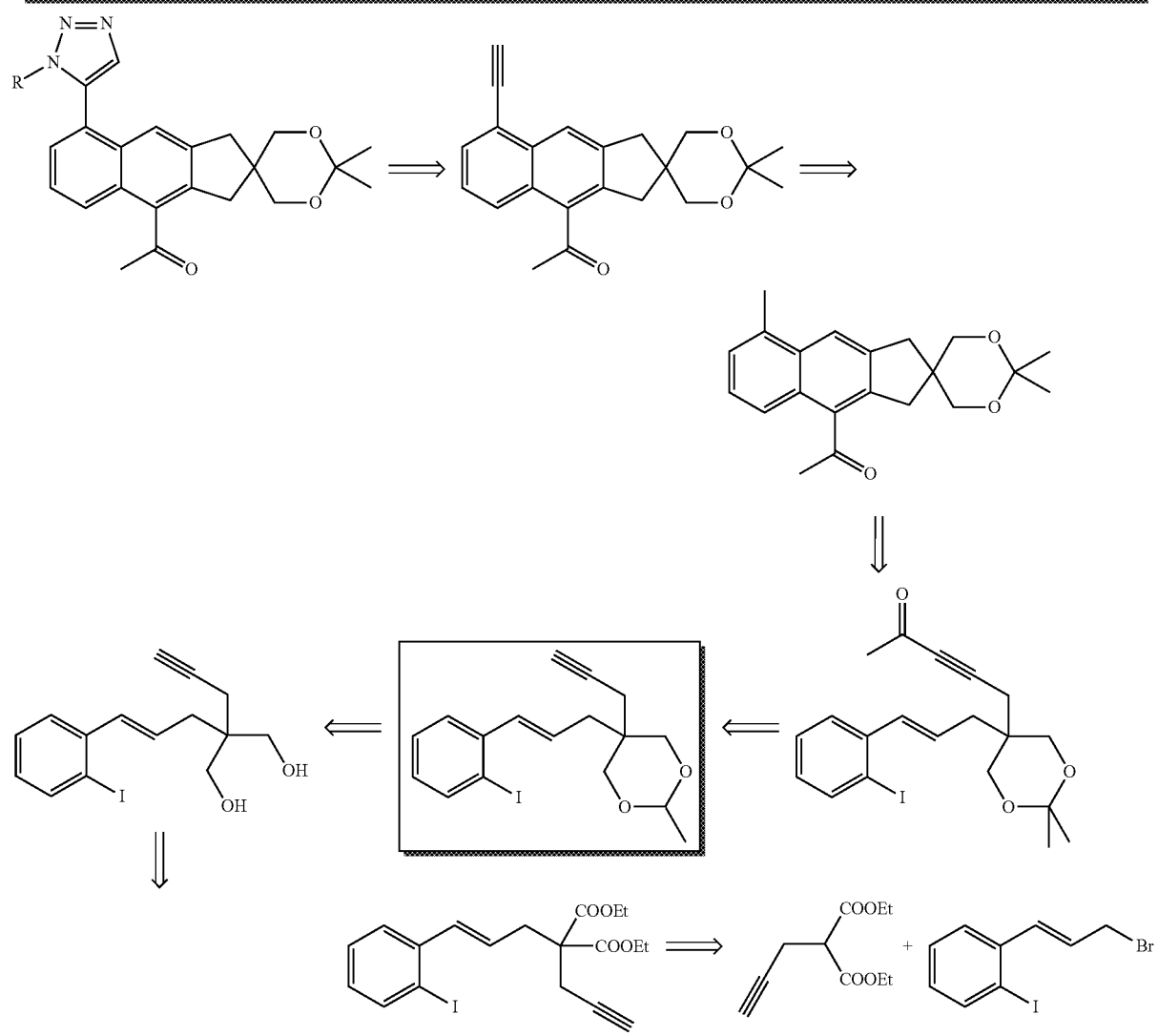

According to various embodiments, the present disclosure may provide for a fluorescent sensor. According to these embodiments, the fluorescent sensor may comprise a functionalized, substituted naphthalene having a structure according to the various embodiments described herein. According to certain embodiments, the fluorescent sensor may comprise a functionalized, substituted naphthalene having a structure

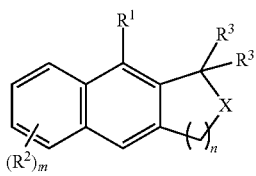

where $R^1$ is a substituent selected from the group consisting of H, $C_1$-$C_{20}$ alkyl, $C_1$-$C_{20}$ alkoxy, phenyl, aryl, heteroaryl, —S(O)$R^4$, —S(O)$_2R^4$, P(O)(O$R^4$)$_2$, and —C(Y)$R^4$ where Y is O, N$R^5$, or S; each $R^2$ is a halogen or an electron donating group selected from —N($R^6$)$_2$, —O$R^6$, and —S$R^6$; each $R^3$ is H, $C_1$-$C_{20}$ alkyl, or combined as =O; each $R^4$, $R^5$ and $R^6$ is independently selected from H, $C_1$-$C_{20}$ alkyl, $C_1$-$C_{20}$ alkoxy, substituted or unsubstituted phenyl, aryl, heteroaryl, benzyl, or may come together to form a cyclic structure; X is CH$_2$, C($R^6$)$_2$, C(CO$_2$Alkyl)$_2$, O, NTs, NH, NCOR$^5$ or N$R^5$; n is an integer from 0 to 2; m is an integer from 1 to 4, provided that either $R^1$ is one of —S(O)$R^4$, —S(O)$_2R^4$, P(O)(O$R^4$)$_2$, and —C(Y)$R^4$ or the $R^3$ groups are combined as =O.

Still further embodiments of the present disclosure may include a solvatochromic fluorophore. According to these embodiments, the solvatochromic fluorophore may comprise a functionalized, substituted naphthalene having a structure according to the various embodiments described herein. According to certain embodiments, the solvatochromic fluorophore may comprise a functionalized, substituted naphthalene having a structure

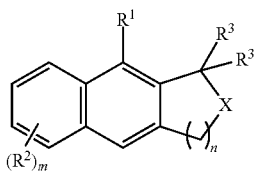

where $R^1$ is a substituent selected from the group consisting of H, $C_1$-$C_{20}$ alkyl, $C_1$-$C_{20}$ alkoxy, phenyl, aryl, heteroaryl, —S(O)$R^4$, —S(O)$_2R^4$, P(O)(O$R^4$)$_2$, and —C(Y)$R^4$ where Y is O, N$R^5$, or S; each $R^2$ is a halogen or an electron donating group selected from —N($R^6$)$_2$, —O$R^6$, and —S$R^6$; each $R^3$ is H, $C_1$-$C_{20}$ alkyl, or combined as =O; each $R^4$, $R^5$ and $R^6$ is independently selected from H, $C_1$-$C_{20}$ alkyl, $C_1$-$C_{20}$ alkoxy, substituted or unsubstituted phenyl, aryl, heteroaryl, benzyl, or may come together to form a cyclic structure; X is CH$_2$, C($R^6$)$_2$, C(CO$_2$Alkyl)$_2$, O, NTs, NH, NCOR$^5$ or N$R^5$; n is an integer from 0 to 2; m is an integer from 1 to 4, provided that either $R^1$ is one of —S(O)$R^4$, —S(O)$_2R^4$, P(O)(O$R^4$)$_2$, and —C(Y)$R^4$ or the $R^3$ groups are combined as =O.

According to various embodiments of the fluorescent sensor or the solvatochromic fluorophore, the sensor or the solvatochromic fluorophore may have a functionalized, substituted naphthalene structure:

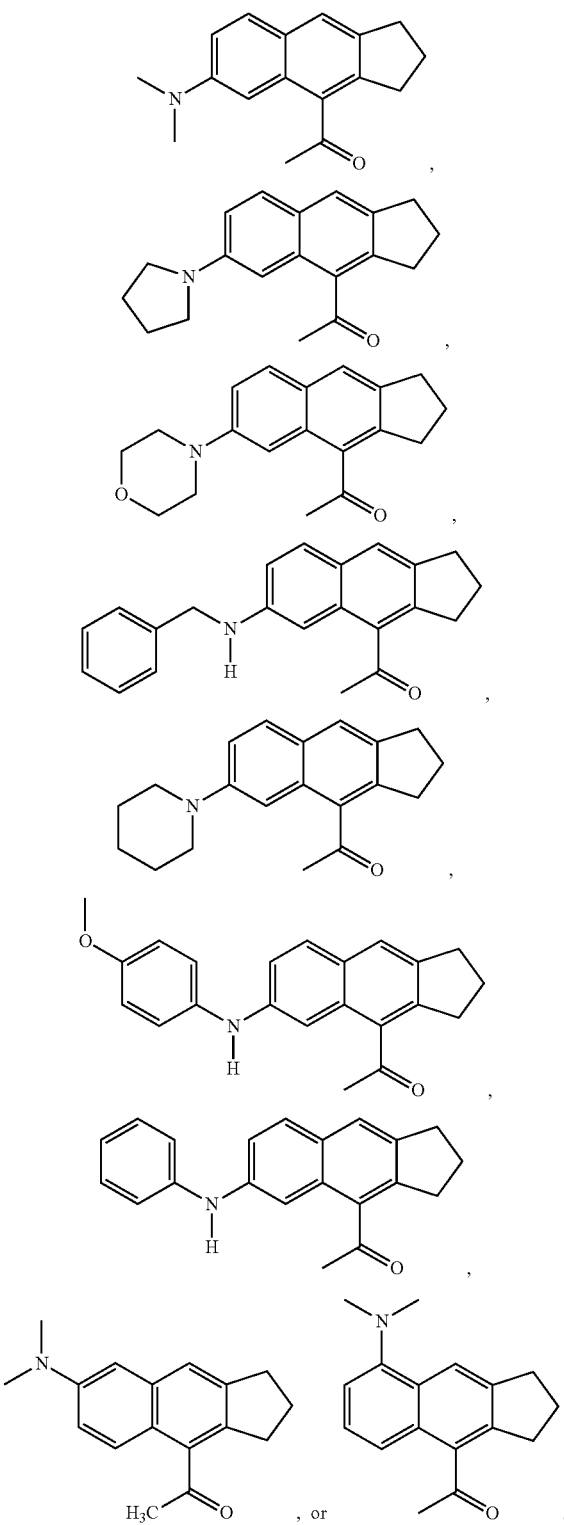

These and other features of the various embodiments of the present disclosure will become more apparent upon consideration of the following examples. The various embodiments of this disclosure described in the following examples are not to be considered as limiting the invention to their details.

EXAMPLES

General Methods

All commercially available compounds were purchased from Aldrich Chemical Co., GFS Chemicals, Strem Chemicals, Acros Organics, Alfa Aesar, and Advanced Chemtech and used as received, except for p-toluenesulfonyl hydrazide, which was recrystallized from methanol. Amines were purchased from Aldrich Chemical Co. as purified by redistillation and used as received. Tetrahydrofuran (THF), diethyl ether ($Et_2O$), and dichloromethane ($CH_2Cl_2$) were purified by passing through alumina using the Sol-Tek ST-002 solvent purification system. Acetonitrile (MeCN) and toluene were freshly distilled from $CaH_2$ prior to use. Benzene was freshly distilled from sodium/benzophenone prior to use Anhydrous N,N-dimethylformamide (DMF), 1,2-dichloroethane (DCE), and 1,4-dioxane were purchased and used as received from Aldrich Chemical Co. Purification of the compounds by flash column chromatography was performed using silica gel (32-63 μm particle size, 60 Å pore size) purchased from Silicycle, or by using a Biotage Horizon flash purification system with either Biotage SNAP KP-SIL silica cartridges, or Teledyne ISCO RediSep Rf normal phase disposable flash columns (40-60 micron). TLC analyses were performed on EMD Chemicals Silica Gel 60 $F_{254}$ glass plates (250 μm thickness). $^1$H NMR and $^{13}$C NMR spectra were recorded on Bruker Avance 300 MHz, 500 MHz, or 600 MHz spectrometers. Spectra were referenced to residual chloroform (7.27 ppm, $^1$H, 77.0 ppm, $^{13}$C) or 1,2-dichlorobenzene (6.93 ppm, $^1$H, 127.19 ppm, $^{13}$C). Chemical shifts are reported in ppm, multiplicities are indicated by s (singlet), d (doublet), t (triplet), q (quartet), p (pentet), and m (multiplet). Coupling constants, J, are reported in hertz (Hz). All NMR spectra were obtained at room temperature unless otherwise specified. IR spectra were obtained using a Nicolet Avatar E.S.P. 360 FT-IR. EI mass spectroscopy was performed on a Waters Micromass GCT high resolution mass spectrometer. ES mass spectroscopy was performed on a Waters Q-TOF Ultima API, Micromass UK Limited high resolution mass spectrometer. GC mass spectrometry was performed on a Shimadzu GCMS-17A/QP5050A spectrometer. All microwave-mediated reactions were carried out using a Biotage Initiator™ Exp microwave synthesizer. The microwave parameters were set to variable power, constant temperature, with the fixed hold time set to on. The microwave reactions were carried out in 0.2-0.5 mL, 0.5-2 mL, 2-5 mL, or 10-20 mL Biotage microwave vials. References located after compound names refer to literature protocols for how to prepare these or similar compounds by comparable methodology. Absorption and fluorescence spectra were recorded on Lambda 9 spectrophotometer (Perkin Elmer) and FluoroMax-3 spectrofluorometer (Jobin Yvon, Horiba), respectively. Fluorescence quantum yields were determined by taking Prodan in DMSO (quantum yield, QY=91%) as a reference. The quantum yield values were corrected for the solvent refractive index. For spectroscopic measurements, $10^{-5}$ M solutions of dyes in 10 mm quartz-cuvettes were used (excitation wavelength was 334 nm; slits open to 2 nm).

Synthesis of Functionalized Naphthalenes

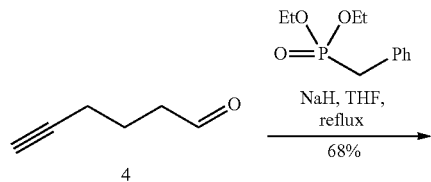

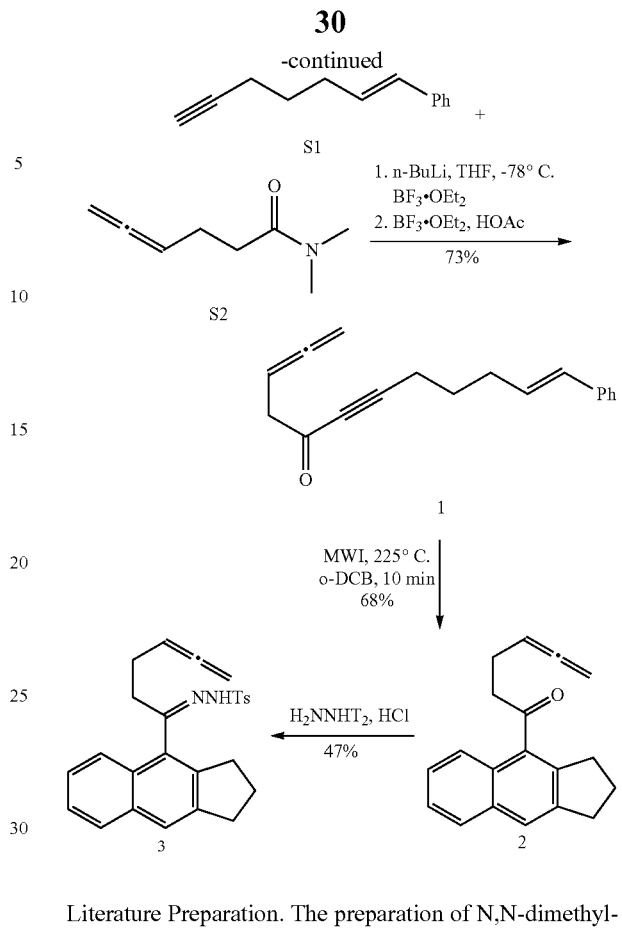

Literature Preparation. The preparation of N,N-dimethyl-hexa-4,5-dien-amide (S2) followed the procedure reported by Brummond et al., *Org. Lett.* 2005, 7, 3473.

Hex-5-ynal (4). To a one-neck 250 mL round-bottomed flask equipped with a septum pierced with a needle and a stir bar was added pyridinium chlorochromate (15.6 g, 72.6 mmol) and DCM (133 mL) with stirring. 5-Hexyn-1-ol (4.00 mL, 36.3 mmol) was added all at once via syringe, and the reaction turned dark brown and thick. The reaction was stirred at rt for 2 h until complete by TLC, followed by addition of $Et_2O$ (100 mL) and silica gel (50 g). The suspension was stirred for 30 min, filtered through a pad of silica gel with $Et_2O$ washings, and then concentrated under reduced pressure to yield the aldehyde 4 as a light yellow oil (2.98 g, 85%). The crude product was carried on without further purification. Compound 4 was previously characterized.

(E)-Hept-1-en-6-yn-1-ylbenzene (S1). To a flame-dried two-neck 250 mL round-bottomed flask equipped with a reflux condenser, an argon inlet adapter, a septum, and a stir bar was added sodium hydride (1.26 g of a 60% dispersion in oil, 31.4 mmol). The flask was flushed with argon, and THF (38 mL) was added via syringe with stirring. Diethyl benzylphosphonate (6.00 mL, 28.8 mmol) in THF (19 mL) was added dropwise over 10 min via syringe, and the reaction was stirred for 15 min at rt. Aldehyde 4 (1.26 g, 13.1 mmol) in THF (19 mL) was added dropwise over 10 min via syringe, turning the reaction from cloudy white to yellow. The reaction was heated at reflux for 2 h until it was complete by TLC. The reaction turned dark brown in color while refluxing. Once the reaction was complete by TLC, it was cooled to rt and quenched with sat'd aq ammonium chloride causing precipitation of tan solids. The aqueous layer was separated and extracted with $Et_2O$ (2×). The combined organic layers were washed with brine, dried over magnesium sulfate, gravity filtered, and concentrated under reduced pressure to yield a crude yellow oil. The crude product was purified by silica gel column chromatography (50 g silica cartridge, 0-25% ethyl acetate/hexanes) to yield enyne S1 as a colorless oil (1.51 g, 68%).

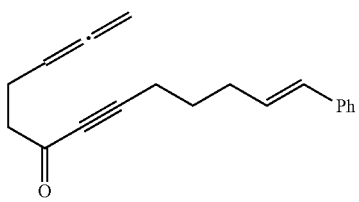

(E)-13-Phenyltrideca-1,2,12-trien-7-yn-6-one (1). To a flame-dried two-neck round-bottomed flask equipped with an argon inlet adapter, a septum, and a stir bar was added enyne S1 (0.225 g, 1.32 mmol) in THF (3.5 mL). The solution was cooled at −78° C. (bath temperature) in a dry ice/acetone bath, and n-butyllithium (0.76 mL of a 1.6 M solution in hexanes, 1.22 mmol) was added dropwise via syringe turning the reaction purple. The reaction was stirred at −78° C. for 45 min, and amide S2 (0.142 g, 1.02 mmol) in THF (3.5 mL) was added dropwise via syringe turning the reaction yellow. The reaction was stirred for 5 min, followed by dropwise addition of boron trifluoride diethyl etherate (0.16 mL, 1.28 mmol) via syringe. The reaction was stirred at −78° C. for 3 h until complete by TLC. Boron trifluoride diethyl etherate (0.16 mL, 1.28 mmol) and acetic acid (70 µL, 1.28 mmol) were added sequentially via syringe. The reaction was then warmed to −20° C. and quenched with sat'd aq ammonium chloride. The aqueous layer was separated and extracted with Et$_2$O (2×). The combined organic layers were washed with brine, dried over magnesium sulfate, gravity filtered, and concentrated under reduced pressure. The crude product was purified by silica gel column chromatography (25 g silica cartridge, 0-10% ethyl acetate/hexanes) to yield the product 1 as a light yellow oil (197 mg, 73%).

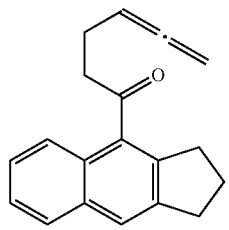

1-(2,3-Dihydro-1H-cyclopenta[b]naphthalen-4-yl)hexa-4,5-dien-1-one (2). To a 2-5 mL MWI vial equipped with a stir bar was added the ene-allene-yne 1 (50 mg, 0.19 mmol) in o-dichlorobenzene (2.5 mL), and the reaction was irradiated with stirring at 225° C. for 10 min until complete by TLC. The reaction was then transferred directly to a silica gel cartridge and purified by silica gel column chromatography (25 g silica cartridge, 0-3% Et$_2$O/pentane) to yield 2 as a light yellow oil (34 mg, 68%).

Data for 2 (LSK-2-162)

$^1$H NMR (400 MHz, CDCl$_3$) 7.79 (s, 1H), 7.31-7.23 (m, 2H), 7.44-7.42 (m, 2H), 5.27 (p, J=7.6 Hz, 1H), 4.71-4.68 (m, 2H), 3.09-3.01 (m, 6H), 2.51-2.49 (m, 2H), 2.17 (p, J=7.2 Hz, 2H) ppm $^{13}$C NMR (100 MHz, CDCl$_3$) 208.4, 208.2, 143.1, 139.5, 134.6, 133.0, 128.6, 128.1, 125.9, 125.4, 124.0, 89.1, 76.1, 43.5, 32.4, 31.9, 26.2, 22.4 ppm IR (thin film) 3057, 2951, 2829, 2283, 1954, 1693, 1607, 1575 cm$^{-1}$ LRMS (TOF MS ES+) m/z (%): 263 (100), 246 (14), 245 (52), 206 (10), 205 (23), 195 (27), 193 (10), 167 (4)

HRMS (TOF MS ES+) [M+H]$^+$ calcd for C$_{19}$H$_{19}$O, 263.1436; found, 263.1436

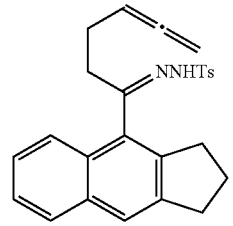

N'-(1-(2,3-dihydro-1H-cyclopenta[b]naphthalen-4-yl)hexa-4,5-dien-1-ylidene)-4-methylbenzene-sulfonohydrazide (3). To a flame-dried one-neck 1 mL flask was added p-toluenesulfonyl hydrazide (0.015 g, 0.080 mmol). The flask was equipped with a septum and purged with argon. Naphthalene 2 (0.021 g, 0.080 mmol) in absolute ethanol (0.25 mL) was added all at once with stirring, and the reaction mixture was heated to reflux in an oil bath. Concentrated hydrochloric acid (5 µL, 0.060 mmol) was added, and the reaction became yellow in color. The reaction remained heating at reflux for 4 h, was let cool to rt, and was stirred at rt for 16 h. The reaction mixture was then taken up in DCM and washed with brine (1×). The organic layer was dried over magnesium sulfate, gravity filtered, and concentrated under reduced pressure to produce a yellow solid. The crude product was purified by silica gel column chromatography (10 g silica cartridge, 0-10% ethyl acetate/hexanes) to yield naphthalene 3 as a white solid (0.016 g, 47% yield). The product still contained some unknown impurity by $^1$H NMR.

Data for 3 (LSK-2-170)

$^1$H NMR (400 MHz, CDCl$_3$) 7.79 (d, J=8.4 Hz, 1H), 7.75-7.72 (m, 3H), 7.42 (t, J=7.4 Hz, 1H), 7.35 (d, J=8.0 Hz, 2H), 7.19 (t, J=7.4 Hz, 1H), 7.10 (s, 1H), 6.96 (d, J=7.7 Hz, 1H), 5.11 (p, J=6.6 Hz, 1H), 4.63-4.59 (m, 2H), 3.07 (t, J=7.5, Hz, 2H), 2.67-2.62 (m, 2H), 2.59-2.53 (m, 2H), 2.51 (s, 3H), 2.33-2.25 (m, 2H), 2.15-2.02 (m, 2H) ppm

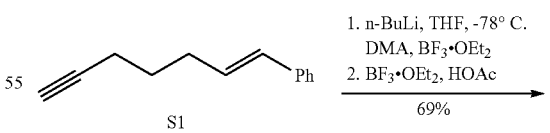

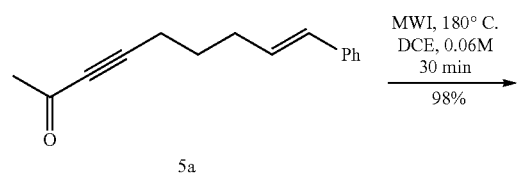

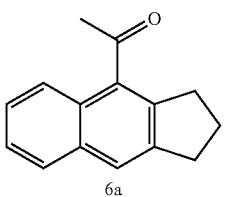

6a

General Procedure A: Acylation of Alkynes

To a flame-dried two-neck round-bottomed flask equipped with an argon inlet adapter, a septum, and a stir bar was added enyne (1.3 equiv) in THF (0.40 M). The solution was cooled at −78° C. (bath temperature) in a dry ice/acetone bath, and n-butyllithium (1.2 equiv) was added dropwise. The reaction was stirred at −78° C. for 45 min, and amide (1.0 equiv) in THF (0.30 M) was added dropwise via syringe. The reaction was stirred for 5 min, followed by dropwise addition of boron trifluoride diethyl etherate (1.25 equiv) via syringe. The reaction was stirred at −78° C. until complete by TLC. Boron trifluoride diethyl etherate (1.25 equiv) and acetic acid (1.25 equiv) were added sequentially via syringe. The reaction was then warmed to −20° C. and quenched with sat'd aq ammonium chloride. The aqueous layer was separated and extracted with Et$_2$O (2×). The combined organic layers were washed with brine, dried over magnesium sulfate, gravity filtered, and concentrated under reduced pressure. The crude product was purified by silica gel column chromatography.

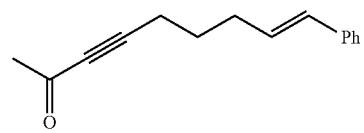 [SMILES: CC(=O)C#CCCC/C=C/c1ccccc1]

(E)-9-Phenylnon-8-en-3-yn-2-one (5a). Follows general procedure A: enyne S1 (0.495 g, 2.91 mmol), THF (8 mL), n-butyllithium (1.7 mL of a 1.6 M solution in hexanes, 2.69 mmol), N,N-dimethylacetamide (0.21 mL, 2.24 mmol), THF (8 mL), boron trifluoride diethyl etherate (0.35 mL, 2.80 mmol), and acetic acid (0.16 mL, 2.80 mmol). The reaction turned yellow upon addition of n-butyllithium, and turned orange upon addition of acetic acid. The reaction was complete after 3 h. The crude product was purified by silica gel column chromatography (50 g silica cartridge, 0-10% ethyl acetate/hexanes) to yield product 5a as a yellow oil (0.329 g, 69%).

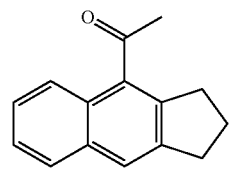 [SMILES: CC(=O)c1c2c(cc3ccccc13)CCC2]

1-(2,3-Dihydro-1H-cyclopenta[b]naphthalen-4-yl)ethanone (6a). To a 0.5-2 mL microwave irradiation vial equipped with a stir bar was added enyne 5a (0.020 g, 0.094 mmol) in DCE (1.6 mL). The reaction was irradiated with stirring at 180° C. for 30 min until complete by TLC. The reaction turned golden in color. The reaction was then transferred to a vial, concentrated under reduced pressure, and dried under vacuum to yield naphthalene 6a as a black oil (0.020 g, quant.).

Data for 6a (LSK-3-046)

$^1$H NMR (400 MHz, CDCl$_3$) 7.82-7.76 (m, 2H), 7.72 (s, 1H), 7.44 (t, J=4.4 Hz, 2H), 3.09-3.04 (m, 4H), 2.66 (s, 3H), 2.17 (p, J=7.4 Hz, 2H) ppm $^{13}$C NMR (100 MHz, CDCl$_3$) 206.3, 143.2, 139.8, 134.7, 133.1, 128.4, 128.1, 126.0, 125.4, 124.4, 124.2, 32.4, 32.2, 32.1, 26.1 ppm IR (thin film) 3023, 3060, 2949, 2853, 2210, 1689, 1597, 1499 cm$^{-1}$ LRMS (TOF MS ES+) m/z (%): 211 (28), 209 (15), 196 (18), 195 (100), 191 (83), 169 (12), 167 (6)

HRMS (TOF MS ES+) [M+H]$^+$ calcd for C$_{15}$H$_{15}$O, 211.1123; found, 211.1154

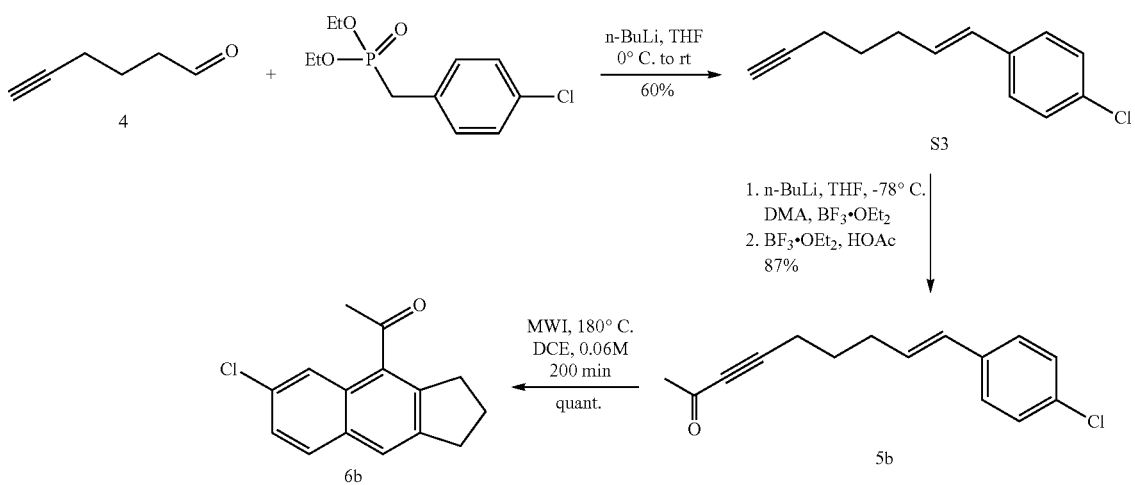

(E)-1-Chloro-4-(hept-1-en-6-yn-1-yl)benzene (S3). (Paquette, L. A. Org. Lett. 2003, 5, 78) To a flame-dried two-neck 100 mL round-bottom flask equipped with an argon inlet adapter, a septum, and a stir bar was added diethyl 4-chlorobenzylphosphonate (2.54 mL, 11.5 mmol) and THF (29 mL) with stirring. The solution was cooled in an ice bath, and n-butyllithium (7.80 mL of a 1.6 M solution in hexanes, 12.5 mmol) was added dropwise via syringe over 10 min, turning the reaction brown. After stirring for 30 min, aldehyde 4 (0.500 g, 5.21 mmol) in THF (18 mL) was added dropwise via syringe over 10 min. The reaction was stirred for 30 min in the ice bath, the ice bath was removed, and then the reaction was warmed to rt and stirred for 3 h. The reaction became darker in color. The reaction was slowly quenched with sat'd aq ammonium chloride, causing the solution to become yellow and to precipitate tan solids. The aqueous layer was separated and extracted with Et$_2$O (2×). The combined organic layers were washed with brine, dried over magnesium sulfate, gravity filtered, and concentrated under reduced pressure. The crude product was purified by silica gel column chromatography (25 g silica cartridge, 2-10% ethyl acetate/hexanes) to yield enyne S3 as a yellow oil (0.632 g, 60%).

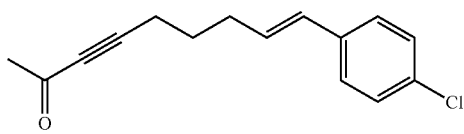 [SMILES: CC(=O)C#CCCC/C=C/c1ccc(Cl)cc1]

(E)-9-(4-Chlorophenyl)non-8-en-3-yn-2-one (5b). Follows general procedure A: enyne S3 (0.904 g, 4.43 mmol), THF (12 mL), n-butyllithium (2.56 mL of a 1.6 M solution in hexanes, 4.09 mmol), N,N-dimethylacetamide (0.32 mL, 3.41 mmol), THF (12 mL), boron trifluoride diethyl etherate (0.53 mL, 4.26 mmol), and acetic acid (0.24 mL, 4.26 mmol). The reaction was complete after 3 h. The crude product was purified by silica gel column chromatography (50 g silica cartridge, 0-10% ethyl acetate/hexanes) to yield the product 5b as a yellow oil (0.729 g, 87%).

Data for 5b (LSK-3-053)
$^1$H NMR (400 MHz, CDCl$_3$) 7.27 (s, 4H), 6.38 (d, J=15.8 Hz, 1H), 6.16 (dt, J=6.8, 15.8 Hz, 1H), 2.42 (t, J=7.2 Hz, 2H), 2.34 (q, J=7.2 Hz, 2H), 2.31 (s, 3H), 1.77 (p, J=7.2 Hz, 2H) ppm
$^{13}$C NMR (125 MHz, CDCl$_3$) 184.8, 135.9, 132.7, 130.0, 129.7, 128.7 (2C), 127.2 (2C), 93.3, 81.8, 32.8, 31.9, 27.2, 18.4 ppm IR (thin film) 3026, 2936, 2855, 2835, 2210, 1674, 1585, 1490, 1090 cm$^{-1}$
LRMS (TOF MS ES+) m/z (%): 248 (42), 246 (100), 230 (40), 228 (56), 204 (50), 202 (98), 194 (18), 193 (60), 192 (35), 168 (33), 167 (26), 166 (15)
HRMS (TOF MS ES+) M+H]$^+$ calcd for C$_{15}$H$_{16}$OCl, 247.0890; found, 247.0914

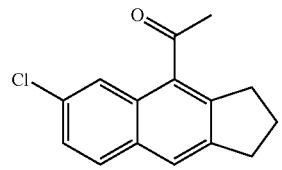 [SMILES: CC(=O)c1c2c(cc3ccc(Cl)cc13)CCC2]

1-(6-Chloro-2,3-dihydro-1H-cyclopenta[b]naphthalen-4-yl)ethanone (6b). To a 2-5 mL microwave irradiation vial equipped with a stir bar was added enyne 5b (0.028 g, 0.12 mmol) in DCE (2.1 mL). The reaction was irradiated with stirring at 180° C. for 200 min until complete by TLC. The reaction turned golden in color. The reaction was then transferred to a vial, concentrated under reduced pressure, and dried under vacuum to yield naphthalene 6b as a brown oil (0.027 g, quant.).

Data for 6b (LSK-3-057)
$^1$H NMR (300 MHz, CDCl$_3$) 7.80 (d, J=1.8 Hz, 1H), 7.72 (d, J=9.0 Hz, 1H), 7.70 (s, 1H), 7.38 (dd, J=1.8, 9.0 Hz, 1H), 3.07 (t, J=7.1 Hz, 4H), 2.66 (s, 3H), 2.18 (p, J=7.1 Hz, 2H) ppm
$^{13}$C NMR (100 MHz, CDCl$_3$) 205.4, 143.6, 141.2, 133.8, 131.9, 131.3, 129.4, 129.0, 126.3, 124.2, 123.5, 32.4, 32.3, 32.1, 26.1 ppm
IR (thin film) 2952, 2884, 2839, 2206, 1688, 1597, 1489, 1088 cm$^{-1}$
LRMS (TOF MS EI+) m/z (%): 246 (18), 244 (47), 231 (38), 229 (100), 201 (28), 191 (20), 166 (35), 165 (75), 63 (20)
HRMS (TOF MS ES+) [M+H]$^+$ calcd for C$_{15}$H$_{14}$OCl, 245.0733; found 245.0743

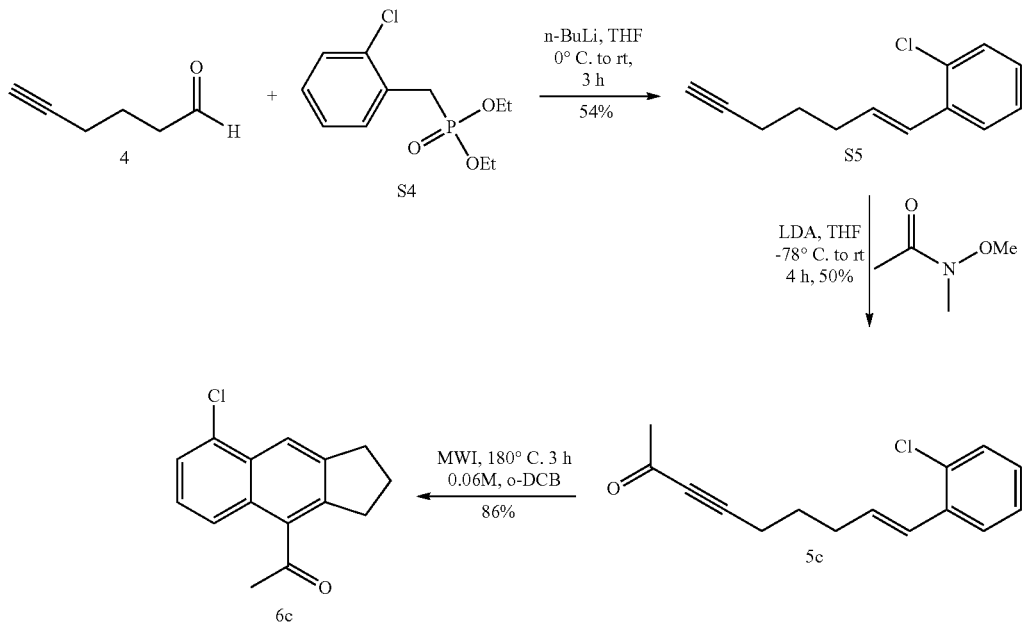

Literature Preparation. Diethyl 2-chlorobenzylphosphonate (S4) was prepared from 1-(bromomethyl)-2-chlorobenzene and triethyl phosphite via the procedure reported by Luscombe (Doubina, N.; Paniagua, S. A.; Soldatova, A. V.; Jen, A. K. Y.; Marder, S. R.; Luscombe C. K. *Macromolecules* 2011, 44, 512).

1-Chloro-2-(hept-1-en-6-yn-1-yl)benzene (S5). An oven-dried 250 mL three-necked round-bottomed flask under a nitrogen atmosphere was charged with 3-chlorobenzylphosphonate (3.9 g, 15 mmol) and THF (60 mL). The solution was cooled to 0° C. in an ice bath for 15 min, then n-BuLi (12 mL of a 1.6 M n-hexane solution, 19 mmol) was added dropwise over 10 min via syringe. The mixture was stirred at 0° C. for 30 min, then aldehyde 4 (1.0 g, 10 mmol) in THF (40 mL) was added. The solution was warmed to rt and was stirred for 3 h. The consumption of the starting material was monitored by TLC (AcOEt/n-hexane 0.5:9.5). The reaction was quenched by adding sat'd aq ammonium chloride solution (70 mL). The layers were separated and the aqueous phase was extracted with ether (3×50 mL). The combined organic layers were washed with brine (2×50 mL), dried over Na$_2$SO$_4$, gravity filtered, and concentrated under reduced pressure. The reaction residue was purified by silica gel flash chromatography, eluting with AcOEt/n-hexane 0.5:9.5, to provide 1.11 g of the title compound as a colorless oil in a 54% yield.

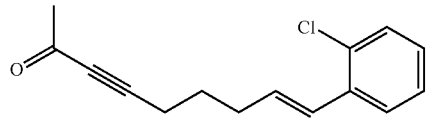 [SMILES: CC(=O)C#CCCC/C=C/c1ccccc1Cl]

9-(2-Chlorophenyl)non-8-en-3-yn-2-one (5c). An oven-dried 100 mL three-necked round-bottomed flask under a nitrogen atmosphere was charged with enyne S5 (1.11 g, 5.4 mmol) and THF (25 mL). The solution was cooled to −78° C. in a dry ice/acetone bath for 15 min, then n-BuLi (3.37 mL of a 1.6 M n-hexane solution, 5.4 mmol) was added via syringe. The mixture was stirred at −78° C. for 40 min, then N,N-dimethylacetamide (0.55 mL, 5.9 mmol) and BF$_3$.Et$_2$O (0.74 mL, 5.9 mmol) were added. The reaction was stirred at −78° C. for an additional 3 h. The consumption of the starting material was monitored by TLC (AcOEt/n-hexane 0.2:9.8). The reaction was quenched by adding sat'd aq ammonium chloride solution (35 mL). The layers were separated and the aqueous phase was extracted with ether (3×30 mL). The combined organic layers were dried over Na$_2$SO$_4$, gravity filtered, and concentrated under reduced pressure. The reaction residue was purified by silica gel flash chromatography, eluting with AcOEt/n-hexane 0.2:9.8 to 1:9, to provide 0.67 g of the title compound as a yellow oil in a 50% yield.

$^1$H NMR (400 MHz, CDCl$_3$) 7.49 (d, J=7.6 Hz, 1H), 7.33 (d, J=7.8 Hz, 1H), 7.24-7.10 (m, 2H), 6.80 (d, J=15.7 Hz, 1H), 6.16 (dt, J=15.7, 7.0 Hz, 1H), 2.43 (t, J=7.1 Hz, 2H), 2.37 (t, J=7.1 Hz, 2H), 2.33 (s, 3H), 1.79 (p, J=7.1 Hz, 2H) ppm $^{13}$C NMR (100 MHz, CDCl$_3$) 184.9, 135.6, 132.7, 132.0, 129.7, 128.3, 127.6, 126.9, 126.8, 93.5, 81.9, 32.9, 32.2, 27.2, 18.5 ppm IR (thin film) 3061, 2933, 2862, 2210, 1647, 1437, 1230 cm$^{-1}$ HRMS (TOF MS ES+) [M+H]$^+$ calcd for C$_{15}$H$_{16}$ClO, 247.0890; found 247.0874

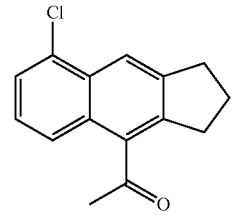 [SMILES: CC(=O)c1c2c(cc3c(Cl)cccc13)CCC2]

1-(8-Chloro-2,3-dihydro-1H-cyclopenta[b]naphthalen-4-yl)ethanone (6c). A microwave irradiation vial (10-20 mL) was equipped with a sir bar (1.5 cm) and was charged with compound 5c (0.20 g, 0.81 mmol) and 1,2-dichlorobenzene (13.5 mL). The reaction was irradiated with stirring at 180° C. for 3 h, turning gold in color. The solution was directly added to a silica gel column, which was eluted with n-hexane to separate the 1,2-dichlorobenzene and then AcOEt/n-hexane 1:9 to collect the pure product. The title compound was isolated as a yellow solid in a 86% yield (0.17 g).

$^1$H NMR (400 MHz, CDCl$_3$) 8.19 (s, 1H), 7.68 (d, J=8.5 Hz, 1H), 7.53 (d, J=7.3 Hz, 1H), 7.34 (t, J=8.0 Hz, 1H), 3.12 (t, J=7.3 Hz, 2H), 3.05 (t, J=7.3 Hz, 2H), 2.64 (s, 3H), 2.19 (p, J=7.3 Hz, 2H) ppm $^{13}$C NMR (100 MHz, CDCl$_3$) 206.0, 144.9, 140.5, 135.2, 132.2, 130.4, 129.7, 125.9, 125.8, 123.6, 120.6, 32.8, 32.3, 32.1, 26.2 ppm IR (thin film) 2952, 1690, 1410, 1350, 1187 cm$^{-1}$ HRMS (TOF MS ES+) [M+H]$^+$ calcd for C$_{15}$H$_{14}$ClO, 245.0733; found 245.0719

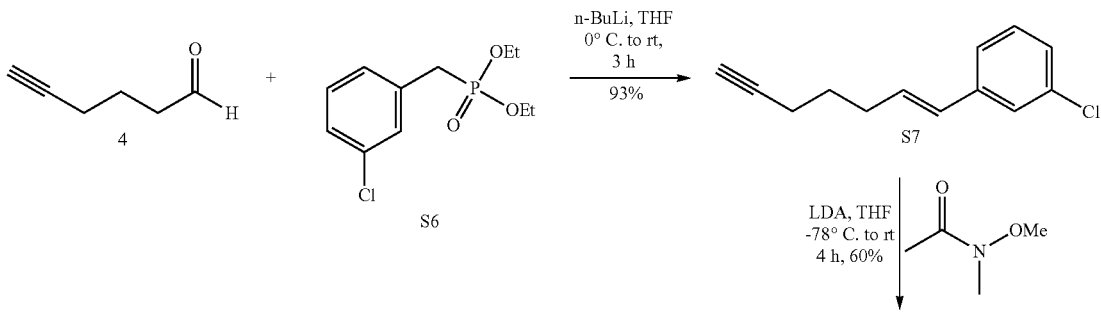

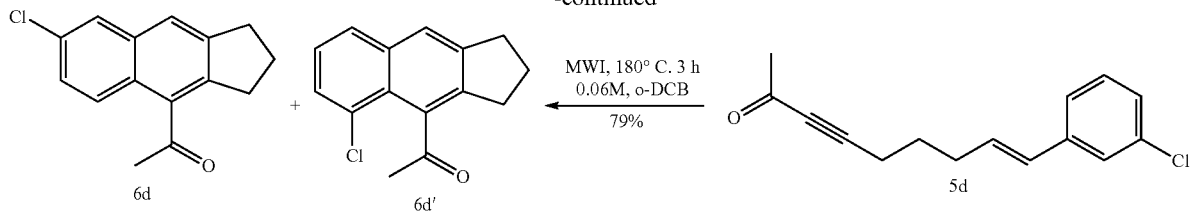

1.4:1 mixture of inseparable isomers

Literature Preparation. Diethyl 3-chlorobenzylphosphonate (S6) prepared from 1-(bromomethyl)-3-chlorobenzene and triethyl phosphite via the procedure reported by Luscombe.

1-Chloro-3-(hept-1-en-6-yn-1-yl)benzene (S7). An oven-dried 250 mL three-necked round-bottomed flask under a nitrogen atmosphere was charged with 3-chlorobenzylphosphonate S6 (4.74 g, 18 mmol) and THF (60 mL). The solution was cooled to 0° C. in an ice bath for 15 min, then n-BuLi (12 mL of a 1.6 M n-hexane solution, 19 mmol) was added dropwise over 10 min via syringe. The mixture was stirred at 0° C. for 30 min, then aldehyde 4 (1.0 g, 10 mmol) in THF (40 mL) was added. The reaction was warmed to rt and was stirred for 3 h. The consumption of the starting material was monitored by TLC (AcOEt/n-hexane 1:9). The reaction was quenched by adding sat'd aq ammonium chloride solution (70 mL). The layers were separated and the aqueous phase was extracted with ether (3×50 mL). The combined organic layers were washed with brine (2×50 mL), dried over $Na_2SO_4$, gravity filtered, and concentrated under reduced pressure. The reaction residue was purified by silica gel flash chromatography, eluting with AcOEt/n-hexane 0.5:9.5, to provide 1.9 g of the title compound as a colorless oil in a 93% yield.

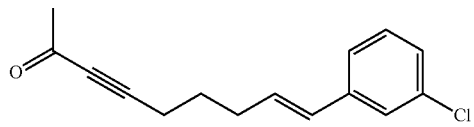 [SMILES: CC(=O)C#CCCC/C=C/c1cccc(Cl)c1]

9-(3-Chlorophenyl)non-8-en-3-yn-2-one (5d). An oven-dried 100 mL three-necked round-bottomed flask under a nitrogen atmosphere was charged with enyne S7 (0.7 g, 3.4 mmol) and THF (40 mL). The solution was cooled to −78° C. in a dry ice/acetone bath for 15 min, then LDA (2 mL of a 2.0 M heptane/THF/ethylbenzene solution, 4.0 mmol) was added via syringe. The mixture was stirred at −78° C. for 1 h, then N-methoxy-N-methylacetamide (0.4 mL, 3.7 mmol) was added. The solution was warmed to rt and was stirred for 4 h. The consumption of the starting material was monitored by TLC (AcOEt/n-hexane 2:8). The reaction was quenched by adding sat'd aq ammonium chloride solution (70 mL). The layers were separated and the aqueous phase was extracted with ether (3×50 mL). The combined organic layers were dried over $Na_2SO_4$, gravity filtered, and concentrated under reduced pressure. The reaction residue was purified by silica gel flash chromatography, eluting with AcOEt/n-hexane 1.5:8.5, to provide 0.52 g of the title compound as a colorless oil in a 60% yield.

Data for 5d (EB-026)

$^1$H NMR (400 MHz, CDCl$_3$) 7.33 (s, 1H), 7.19 (td, J=7.2, 2.2 Hz, 3H), 6.37 (d, J=15.8 Hz, 1H), 6.31-6.04 (m, 1H), 2.42 (t, J=7.1 Hz, 2H), 2.34 (d, J=8.9 Hz, 5H), 1.76 (p, J=7.2 Hz, 2H) ppm $^{13}$C NMR (100 MHz, CDCl$_3$) 184.9, 139.4, 134.6, 130.7, 130.0, 129.9, 127.2, 126.0, 124.4, 93.4, 81.9, 32.9, 32.0, 27.3, 18.5 ppm IR (thin film) 2934, 2210, 1674, 1229, 964 cm$^{-1}$ HRMS (TOF MS ES+) [M+H]$^+$ calcd for $C_{15}H_{16}ClO$, 247.0890; found 247.0886

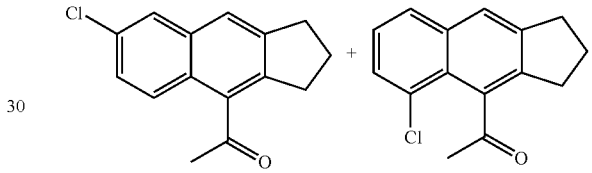

1-(7-chloro-2,3-dihydro-1H-cyclopenta[b]naphthalen-4-yl)ethanone (6d) and 1-(5-Chloro-2,3-dihydro-1H-cyclopenta[b]naphthalen-4-yl)ethanone (6d').A 10-20 mL microwave irradiation vial was equipped with a sir bar and was charged with compound 5d (0.2 g, 0.81 mmol) and 1,2-dichlorobenzene (13.5 mL). The reaction was irradiated with stirring at 180° C. for 3 h, turning gold in color. The solution was directly added to a silica gel column, which was eluted with n-hexane to separate the 1,2-dichlorobenzene and then AcOEt/n-hexane 1:9 to collect the pure products. The title compounds were isolated as a 1.4:1 mixture of inseparable isomers in a 79% yield.

Data for 6d and 6d' (EB-028)

$^1$H NMR (400 MHz, CDCl$_3$) 7.73-7.58 (m, 2H major isomer and 2H minor isomer), 7.53 (s, 1H major isomer), 7.44 (d, J=7.4 Hz, 1H minor isomer), 7.35-7.21 (m, 1H major isomer and 1H minor isomer), 3.02-2.97 (m, 4H major isomer and 4H minor isomer), 2.60 (s, 3H, minor isomer), 2.59 (s, 3H, major isomer), 2.14-2.06 (m, 2H major isomer and 2H minor isomer) ppm $^{13}$C NMR (100 MHz, CDCl$_3$) 206.7 (minor isomer), 205.5 (major isomer), 144.6 (major isomer), 144.0 (major isomer), 141.3 (minor isomer), 140.3 (major isomer), 135.1 (major isomer), 134.7 (minor isomer), 134.6 (1C major isomer and 1C minor isomer), 133.9 (major isomer), 131.2 (major isomer), 129.4 (minor isomer), 127.7 (minor isomer), 127.5 (major isomer), 126.7 (major isomer), 126.7 (minor isomer), 126.3 (minor isomer), 126.0 (major isomer), 125.4 (minor isomer), 124.0 (minor isomer), 123.4 (major isomer), 33.7 (minor isomer), 32.4 (minor isomer), 32.4 (major isomer), 32.2 (major isomer), 32.1 (major isomer), 31.6 (minor isomer), 26.1 (major isomer), 25.8 (minor isomer) ppm IR (thin film) 2949, 1969, 1598, 1418, 1142 cm$^{-1}$ HRMS (TOF MS ES+) [M+H]⁺ calcd for $C_{15}H_{14}ClO$, 245.0733; found 245.0728

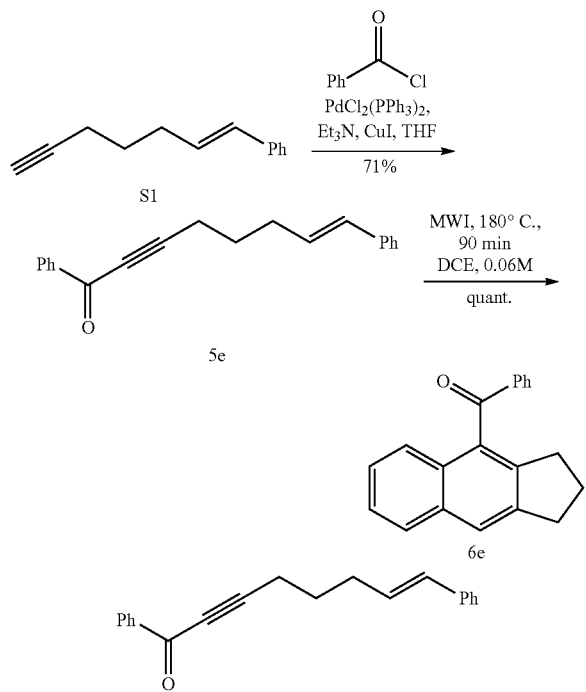

(E)-1,8-Diphenyloct-7-en-2-yn-1-one (5e). (Cacchi, S. et al. *Org. Lett.* 2008, 10, 2629) To a flame-dried two-neck 10 mL round-bottomed flask equipped with an argon inlet adapter, a septum, and a stir bar was added $PdCl_2(PPh_3)_2$ (0.012 g, 0.017 mmol), THF (3 mL), triethylamine (0.14 mL, 1.03 mmol), and benzoyl chloride (0.12 mL, 1.03 mmol). The solution was stirred for 10 min at rt, and copper(I) iodide (0.007 g, 0.034 mmol) was added all at once through the sidearm turning the reaction from cloudy yellow to clear orange. The reaction was stirred for 10 min, and enyne S1 (0.146 g, 0.86 mmol) in THF (0.5 mL) was added all at once via syringe. The reaction was stirred for 3 h until complete by TLC, in which time the reaction became cloudy and yellow. Water was added to the reaction, and the aqueous layer was separated and extracted with ethyl acetate (2×). The combined organic layers were washed with 1 M hydrochloric acid, sat'd aq ammonium chloride, and brine, dried over magnesium sulfate, gravity filtered, and concentrated under reduced pressure. The crude product was purified by silica gel column chromatography (25 g silica cartridge, 0-10% ethyl acetate/hexanes) to yield product 5e as a yellow oil (0.168 g, 71%).

Data for 5e (LSK-3-042)

¹H NMR (400 MHz, $CDCl_3$) 8.16 (d, J=7.7 Hz, 2H), 7.61 (t, J=7.7 Hz, 1H), 7.49 (t, J=7.7 Hz, 2H), 7.36 (d, J=7.7 Hz, 2H), 7.31 (t, J=7.7 Hz, 2H), 7.22 (t, J=7.7 Hz, 1H), 6.47 (d, J=15.8 Hz, 1H), 6.22 (dt, J=7.1, 15.8 Hz, 1H), 2.58 (t, J=7.2 Hz, 2H), 2.43 (q, J=7.2 Hz, 2H), 1.89 (p, J=7.2 Hz, 2H) ppm ¹³C NMR (100 MHz, $CDCl_3$) 178.2, 137.5, 136.9, 134.0, 131.3, 129.6 (2C), 128.9, 128.6 (2C), 128.5 (2C), 127.2, 126.1 (2C), 96.3, 80.1, 32.1, 27.5, 18.7 ppm IR (thin film) 3080, 3059, 3025, 2935, 2851, 2234, 2200, 1642, 1596, 1579, 1492, 1449, 742 cm⁻¹

LRMS (TOF MS ES+) m/z (%): 275 (65), 274 (35), 257 (100), 258 (29), 242 (18), 215 (12)

HRMS (TOF MS ES+) [M+H]⁺ calcd for $C_{20}H_{19}O$, 275.1436; found, 275.1380

(2,3-Dihydro-1H-cyclopenta[b]naphthalen-4-yl)(phenyl)methanone (6e). To a 2-5 mL microwave irradiation vial equipped with a stir bar was added enyne 5e (0.050 g, 0.18 mmol) in DCE (3.0 mL). The reaction was irradiated with stirring at 180° C. for 90 min until complete by TLC. The reaction turned golden in color. The reaction was then transferred to a vial, concentrated under reduced pressure, and dried under vacuum to yield naphthalene 6e as a black oil (0.050 g, quant.).

Data for 6e (LSK-3-050)

¹H NMR (400 MHz, $CDCl_3$) 7.72 (t, J=8.1 Hz, 2H), 7.79 (s, 1H), 7.58 (d, J=8.1 Hz, 2H), 7.47-7.39 (m, 4H), 7.33 (t, J=8.1 Hz, 1H), 2.98 (t, J=7.4 Hz, 2H), 2.70 (t, J=7.4 Hz, 2H), 1.98 (p, J=7.4 Hz, 2H) ppm ¹³C NMR (100 MHz, $CDCl_3$) 199.3, 143.1, 141.3, 137.7, 133.7, 133.0, 132.3, 130.0, 129.9 (2C), 128.8, 125.8, 125.4, 125.1, 124.0, 32.4, 31.8, 26.0 ppm IR (thin film) 3080, 3059, 3023, 2950, 2835, 1664, 1595, 1448, 749 cm⁻¹

LRMS (TOF MS EI+) m/z (%): 272 (100), 271 (50), 257 (22), 255 (26), 253 (22), 167 (19), 165 (50), 152 (20), 105 (15), 77 (20)

HRMS (TOF MS ES+) [M+H]⁺ calcd for $C_{20}H_{17}O$, 273.1279; found, 273.1301

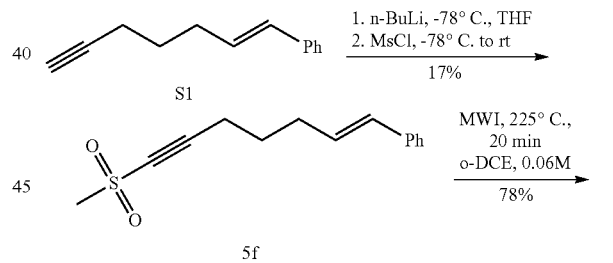

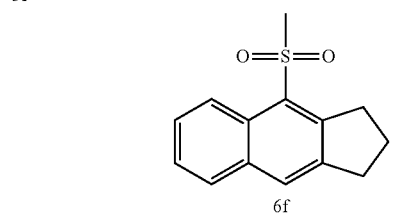

(E)-(7-(Methylsulfonyl)hept-1-en-6-yn-1-yl)benzene (5f). (Saberi, S. P. et al., *J. Chem. Soc., Perkin Trans.* 1 1994, 167) To a flame-dried two-neck 25 mL round-bottomed flask equipped with an argon inlet adapter, a septum, and a stir bar was added enyne S1 (0.400 g, 2.35 mmol) and THF (5 mL) via syringe. The solution was cooled at −78° C. (bath temperature) in a dry ice/acetone bath, and n-butyllithium (1.53 mL, 2.44 mmol) was added dropwise via syringe turning the reaction pink. The reaction was stirred at −78° C. for 1 h, and methanesulfonyl chloride (0.19 mL, 2.40 mmol) was added dropwise via syringe turning the reaction yellow. The reaction was stirred at −78° C. for 45 min, and was then warmed to rt and stirred for 1 h. The reaction was quenched with sat'd aq ammonium chloride, and the aqueous layer was separated. The aqueous layer was extracted with Et₂O (5×), and the combined organic layers were washed with brine, dried over magnesium sulfate, gravity filtered, and concentrated under reduced pressure. The crude product was purified by silica gel column chromatography (50 g silica cartridge, 0-30% ethyl acetate/hexanes) to yield product 5f as a colorless oil (0.101 g, 17%).

Data for 5f (LSK-3-013)

$^1$H NMR (400 MHz, CDCl₃) 7.36 (d, J=7.1 Hz, 2H), 7.31 (t, J=7.1 Hz, 2H), 7.23 (t, J=7.1 Hz, 1H), 6.44 (d, J=15.7 Hz, 1H), 6.16 (dt, J=7.4, 15.7 Hz, 1H), 3.18 (s, 3H), 2.48 (t, J=7.4 Hz, 2H), 2.35 (q, J=7.4 Hz, 2H), 1.82 (p, J=7.4 Hz, 2H) ppm $^{13}$C NMR (100 MHz, CDCl₃) 137.2, 131.6, 128.6 (2C), 128.3, 127.3, 126.1 (2C), 95.2, 77.7, 46.7, 31.9, 26.6, 18.2 ppm IR (thin film) 3084, 3043, 3024, 2925, 2847, 2200, 1596, 1492, 1320, 1147, 771 cm$^{-1}$ LRMS (TOF MS ES+) m/z (%): 250 (10), 249 (100), 231 (20), 219 (36), 186 (22), 185 (36), 168 (22)

HRMS (TOF MS ES+) [M+H]⁺ calcd for C₁₄H₁₇O₂S, 249.0949; found, 249.0939

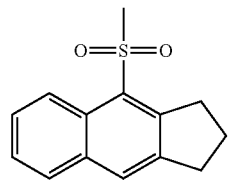 [SMILES: CS(=O)(=O)c1c2c(cc3ccccc13)CCC2]

4-(Methylsulfonyl)-2,3-dihydro-1H-cyclopenta[b]naphthalene (6f). To a 2-5 mL microwave irradiation vial equipped with a stir bar was added enyne 5f (0.050 g, 0.20 mmol) in o-dichlorobenzene (2.3 mL). The reaction was irradiated with stirring at 225° C. for 20 min until complete by TLC. The reaction turned golden in color. The crude product was purified by silica gel column chromatography (14 g silica cartridge, 0-15% ethyl acetate/hexanes) to yield naphthalene 6f as a colorless oil (0.038 g, 78%).

Data for 6f (LSK-3-019)

$^1$H NMR (400 MHz, CDCl₃) 8.86 (d, J=8.8 Hz, 1H), 7.92 (s, 1H), 7.85 (d, J=8.0 Hz, 1H), 7.61 (t, J=8.4 Hz, 1H), 7.53 (t, J=7.2 Hz, 1H), 3.62 (t, J=7.4 Hz, 2H), 3.21 (s, 3H), 3.08 (t, J=7.4 Hz, 2H), 2.16 (p, J=7.4 Hz, 2H) ppm $^{13}$C NMR (100 MHz, CDCl₃) 147.7, 144.2, 133.8, 130.4, 129.0, 128.8, 128.7, 127.5, 126.0, 124.1, 44.7, 34.6, 32.2, 25.6 ppm IR (thin film) 3015, 2957, 2933, 2876, 2839, 1607, 1495, 1302, 1134 cm$^{-1}$ LRMS (TOF MS ES+) m/z (%): 247 (100), 246 (28), 168 (75), 166 (15)

HRMS (TOF MS ES+) [M+H]⁺ calcd for C₁₄H₁₅O₂S, 247.0793; found, 247.0762

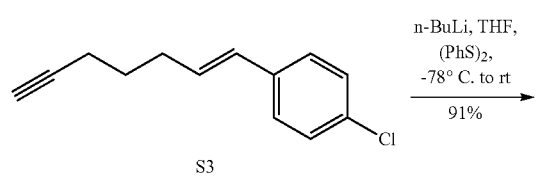

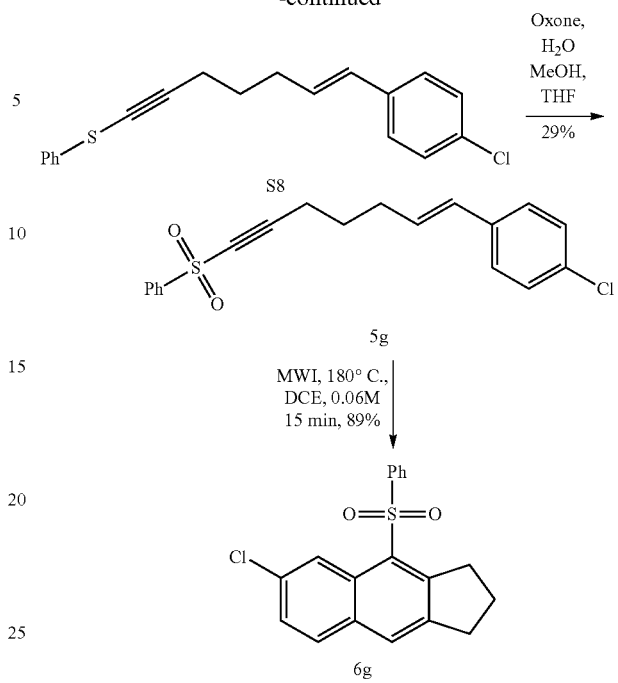

(E)-(7-(4-Chlorophenyl)hept-6-en-1-yn-1-yl)(phenyl)sulfane (S8). (Corlay, H. et al. *Tetrahedron* 1995, 51, 3303.) To a flame-dried two-neck 50 mL round-bottomed flask equipped with an argon inlet adapter, a septum, and a stir bar was added enyne S3 (0.465 g, 2.23 mmol) in THF (21 mL). The solution was cooled at −78° C. (bath temperature) in a dry ice/acetone bath and n-butyllithium (1.68 mL of a 1.6 M solution in hexanes, 2.68 mmol) was added dropwise via syringe turning the reaction yellow. The reaction was stirred at −78° C. for 1 h, and then diphenyl disulfide (0.681 g, 3.12 mmol) in THF (5.5 mL) was added dropwise via syringe turning the reaction colorless. The reaction was stirred at −78° C. for 30 min, and then was warmed to rt and stirred for 3 h turning the reaction yellow. The reaction was diluted with water and the layers were separated. The aqueous layer was extracted with Et₂O (3×), and the combined organic layers were washed with brine, dried over magnesium sulfate, gravity filtered, and concentrated under reduced pressure. The crude product was purified by silica gel column chromatography (40 g silica cartridge, pentane) to yield sulfide S8 as a yellow oil (0.636 g, 91%).

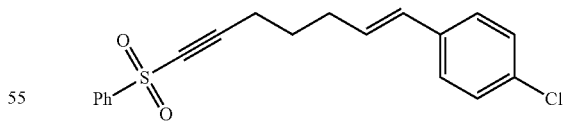

(E)-1-Chloro-4-(7-(phenylsulfonyl)hept-1-en-6-yn-1-yl)benzene (5g). (Trost, B. M.; Curran, D. P. *Tet. Lett.* 1981, 22, 1287) To a scintillation vial equipped with a stir bar was added sulfide S8 (0.139 g, 0.45 mmol) in methanol (1.6 mL) and THF (1.6 mL). The solution was cooled in an ice bath, and oxone (0.479 g, 3.15 mmol) in water (1.6 mL) was added dropwise via pipette with vigorous stirring causing the reaction to turn white and cloudy. The reaction was stirred at rt for 3 days, and was then diluted with water (3 mL). The aqueous layer was separated and extracted with DCM (3×). The combined organic layers were washed with brine, dried over magnesium sulfate, gravity filtered, and concentrated under reduced pressure. The crude product was purified by silica gel column chromatography (4 g silica cartridge, 0-50% ethyl acetate/hexanes) to yield sulfone 5g as a pink oil (45 mg, 29%).

Data for 5g (LSK-3-185)

$^1$H NMR (300 MHz, CDCl$_3$) 8.02 (dd, J=7.6, 1.4 Hz, 2H), 7.69 (dt, J=7.4, 1.0 Hz, 1H), 7.59 (t, J=7.8 Hz, 2H), 7.29 (m, 4H), 6.32 (d, J=15.8 Hz, 1H), 6.08 (dt, J=7.0, 15.8 Hz, 1H), 2.43 (t, J=7.1 Hz, 2H), 2.28 (q, J=7.1 Hz, 2H), 1.75 (p, J=7.1 Hz, 2H) ppm $^{13}$C NMR (125 MHz, CDCl$_3$) 142.1, 135.8, 134.0, 132.8, 130.4, 129.3 (2C), 129.0, 128.7 (2C), 127.2 (2C), 127.2 (2C), 97.2, 78.7, 31.8, 26.4, 18.3 ppm IR (thin film) 3063, 3023, 2933, 2868, 2200, 1585, 1489, 1328, 1160, 756, 728 cm$^{-1}$ LRMS (TOF MS ES+) m/z (%): 346 (60), 316 (55), 282 (74), 220 (75), 203 (100)

HRMS (TOF MS ES+) [M–H]$^+$ calcd for C$_{19}$H$_{16}$O$_2$SCl, 343.0560; found, 343.0562

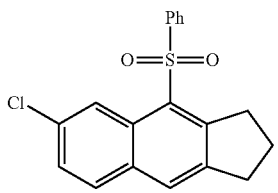 [SMILES: O=S(=O)(c1ccccc1)c1c2c(cc3ccc(Cl)cc13)CCC2]

6-Chloro-4-(phenylsulfonyl)-2,3-dihydro-1H-cyclopenta[b]naphthalene (6g). To a 2-5 mL microwave irradiation vial equipped with a stir bar was added enyne 5g (0.045 g, 0.13 mmol) in DCE (2.2 mL). The reaction was irradiated with stirring at 180° C. for 15 min until complete by TLC. The reaction turned light yellow in color. The reaction was then transferred to a vial, concentrated under reduced pressure, and dried under vacuum to yield naphthalene 6g as a white solid (0.040 g, 89%).

Data for 6g (LSK-3-204)

MP Decomposes at 140° C.

$^1$H NMR (300 MHz, CDCl$_3$) 8.94 (s, 1H), 7.93 (d, J=7.7 Hz, 2H), 7.85 (s, 1H), 7.70 (d, J=8.6 Hz, 1H), 7.55-7.46 (m, 3H), 7.40 (dd, J=1.9, 8.6 Hz, 1H), 3.68 (t, J=7.5 Hz, 2H), 3.08 (t, J=7.5 Hz, 2H), 2.18 (p, J=7.5 Hz, 2H) ppm $^{13}$C NMR (100 MHz, CDCl$_3$) 149.3, 144.5, 142.8, 133.3, 133.0, 132.0, 129.7, 129.7, 129.4, 129.1 (2C), 128.9, 126.8, 126.4 (2C), 123.7, 35.1, 32.1, 25.5 ppm IR (thin film) 3065, 2961, 2921, 2859, 1623, 1599, 1487, 1305, 1154, 754, 719 cm$^{-1}$ LRMS (TOF MSMS ES+) m/z (%): 342 (100), 307 (12), 265 (18), 243 (75), 202 (45), 200 (25)

HRMS (TOF MS ES+) [M+H]$^+$ calcd for C$_{19}$H$_{16}$O$_2$SCl, 343.0560; found, 343.0548

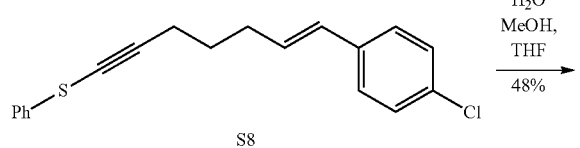

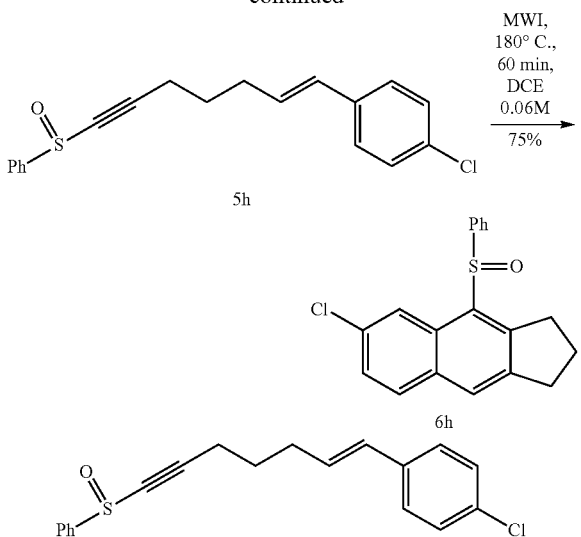

(E)-1-Chloro-4-(7-(phenylsulfinyl)hept-1-en-6-yn-1-yl)benzene (5h). To a scintillation vial equipped with a stir bar was added sulfide S8 (0.075 g, 0.24 mmol) in methanol (0.85 mL) and THF (0.85 mL). The solution was cooled in an ice bath, and oxone (0.110 g, 0.72 mmol) in water (0.85 mL) was added dropwise via pipette with vigorous stirring causing the reaction to turn white and cloudy. The reaction was stirred at rt for 13 h, and was then diluted with water (2 mL). The aqueous layer was separated and extracted with DCM (3×). The combined organic layers were washed with brine, dried over magnesium sulfate, gravity filtered, and concentrated under reduced pressure. The crude product was purified by silica gel column chromatography (10 g silica cartridge, 0-50% ethyl acetate/hexanes) to yield sulfoxide 5h as a colorless oil (38 mg, 48%).

Data for 5 h (LSK-3-186)

$^1$H NMR (300 MHz, CDCl$_3$) 7.83-7.80 (m, 2H), 7.58-7.54 (m, 3H), 7.26 (s, 4H), 6.33 (d, J=16.0 Hz, 1H), 6.11 (dt, J=6.8, 16.0 Hz, 1H), 2.49 (t, J=7.0 Hz, 2H), 2.30 (q, J=7.0 Hz, 2H), 1.76 (p, J=7.0 Hz, 2H) ppm $^{13}$C NMR (125 MHz, CDCl$_3$) 144.4, 135.9, 132.7, 131.6, 130.1, 129.5 (2C), 129.5 (2C), 128.7 (2C), 127.2 (2C), 124.9 (2C), 105.4, 78.9, 31.8, 27.0, 19.2 ppm IR (thin film) 3057, 3025, 2932, 2862, 2180, 1646, 1593, 1489, 1088, 800, 749 cm$^{-1}$ LRMS (TOF MSMS ES+) m/z (%): 327 (55), 310 (100), 275 (12)

HRMS (TOF MS ES+) [M+H]$^+$ calcd for C$_{19}$H$_{18}$OSCl, 329.0767; found, 329.0745

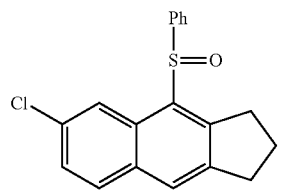 [SMILES: O=S(c1ccccc1)c1c2c(cc3ccc(Cl)cc13)CCC2]

6-Chloro-4-(phenylsulfinyl)-2,3-dihydro-1H-cyclopenta[b]naphthalene (6h). To a 0.5-2 mL microwave irradiation vial equipped with a stir bar was added enyne 5h (0.036 g, 0.11 mmol) in DCE (1.8 mL). The reaction was irradiated with stirring at 180° C. for 60 min until complete by TLC. The reaction turned golden in color. The reaction was then transferred to a vial, concentrated under reduced pressure, and dried under vacuum to yield naphthalene xx as a golden oil (0.027 g, 75%).

Data for 6 h (LSK-3-190)

$^1$H NMR (300 MHz, CDCl$_3$) 8.60 (s, 1H), 7.76 (s, 1H), 7.72 (d, J=8.7 Hz, 1H), 7.56-7.54 (m, 2H), 7.47-7.37 (m, 4H), 3.52-3.41 (m, 1H), 3.17-3.09 (m, 1H), 3.04 (t, J=7.5 Hz, 2H), 2.23-2.11 (m, 2H) ppm $^{13}$C NMR (100 MHz, CDCl$_3$) 147.5, 144.4, 143.9, 132.5, 132.3, 132.0, 130.6, 130.0, 129.7, 129.0 (2C), 126.8, 126.7, 124.3 (2C), 122.7, 31.9, 31.5, 25.8 ppm IR (thin film) 3057, 2949, 2921, 2847, 1595, 1487, 1441, 1084, 1043, 746 cm$^{-1}$ LRMS (TOF MS ES+) m/z (%): 327 (100), 309 (50)

HRMS (TOF MS ES+) [M+H]$^+$ calcd for C$_{19}$H$_{16}$OSCl, 327.0610; found, 327.0617 over magnesium sulfate, gravity filtered, and concentrated under reduced pressure. The crude product was purified by silica gel column chromatography (10 g silica cartridge, 0-80% ethyl acetate/hexanes) to yield product 5i as a yellow oil (0.056 g, 22%).

Data for 5i (LSK-4-001)

$^1$H NMR (300 MHz, CDCl$_3$) 7.27 (s, 4H), 6.38 (d, J=15.9 Hz, 1H), 6.14 (dt, J=7.0, 15.9 Hz, 1H), 4.16 (p, J=7.3 Hz, 4H), 2.41 (q, J=7.3 Hz, 2H), 2.34 (q, J=7.3 Hz, 2H), 1.78 (p, J=7.3 Hz, 2H), 1.38 (t, J=7.1 Hz, 6H) ppm $^{13}$C NMR (100 MHz, CDCl$_3$) 135.8, 132.6, 130.0, 129.4, 128.6 (2C), 127.2 (2C), 102.3 (d, J=53.0 Hz), 70.9 (d, J=301 Hz), 62.9 (d, J=5 Hz), 31.8, 26.9 (d, J=5 Hz), 18.6 (d, J=4 Hz), 16.0 (d, J=8 Hz) ppm IR (thin film) 2983, 2934, 2896, 2203, 1650, 1489, 1263, 1026, 751 cm$^{-1}$ LRMS (TOF MS ES+) m/z (%): 341 (100), 283 (12), 203 (38), 155 (21)

HRMS (TOF MS ES+) [M+H]$^+$ calcd for C$_{17}$H$_{23}$O$_3$PCl, 341.1073; found, 341.1078

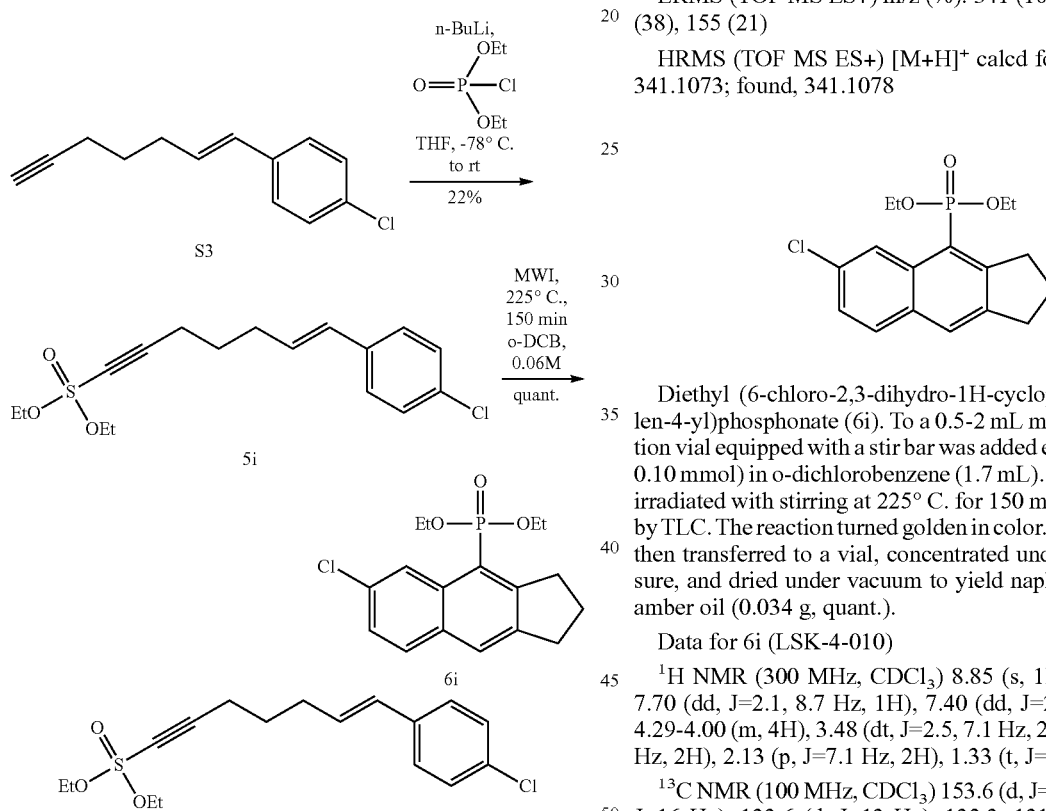

Diethyl (6-chloro-2,3-dihydro-1H-cyclopenta[b]naphthalen-4-yl)phosphonate (6i). To a 0.5-2 mL microwave irradiation vial equipped with a stir bar was added enyne 5i (0.034 g, 0.10 mmol) in o-dichlorobenzene (1.7 mL). The reaction was irradiated with stirring at 225° C. for 150 min until complete by TLC. The reaction turned golden in color. The reaction was then transferred to a vial, concentrated under reduced pressure, and dried under vacuum to yield naphthalene 6i as an amber oil (0.034 g, quant.).

Data for 6i (LSK-4-010)

$^1$H NMR (300 MHz, CDCl$_3$) 8.85 (s, 1H), 7.80 (s, 1H), 7.70 (dd, J=2.1, 8.7 Hz, 1H), 7.40 (dd, J=2.1, 8.7 Hz, 1H), 4.29-4.00 (m, 4H), 3.48 (dt, J=2.5, 7.1 Hz, 2H), 3.04 (t, J=7.1 Hz, 2H), 2.13 (p, J=7.1 Hz, 2H), 1.33 (t, J=6.9 Hz, 6H) ppm $^{13}$C NMR (100 MHz, CDCl$_3$) 153.6 (d, J=11 Hz), 143.6 (d, J=16 Hz), 133.6 (d, J=13 Hz), 132.3, 131.2 (d, J=12 Hz), 130.5, 129.4, 127.7, 127.4 (d, J=3 Hz), 126.2, 125.8 (d, J=3 Hz), 61.8 (d, J=5 Hz), 35.2, 32.3, 25.6, 16.3 (d, J=6 Hz) ppm IR (thin film) 3080, 2979, 2900, 1621, 1598, 1488, 1238 cm$^{-1}$ LRMS (TOF MS ES+) m/z (%): 339 (100), 338 (95), 311 (73), 303 (65), 283 (72)

HRMS (TOF MS ES+) [M+H]$^+$ calcd for C$_{17}$H$_{21}$O$_3$PCl, 339.0917; found, 339.0928

(E)-Diethyl (7-(4-chlorophenyl)hept-6-en-1-yn-1-yl) phosphonate (5i). (Knierzinger, A. et al. Helv. Chim. Acta 1991, 74, 517.) To a flame-dried two-neck 5 mL round-bottomed flask equipped with an argon inlet adapter, a septum, and a stir bar was added enyne S3 (0.150 g, 0.74 mmol) in THF (2.5 mL). The solution was cooled at −78° C. (bath temperature) in a dry ice/acetone bath and n-butyllithium (0.69 mL of a 1.6 M solution in hexanes, 1.10 mmol) was added dropwise via syringe turning the reaction amber. The reaction was stirred at −78° C. for 1.5 h, and then diethyl chlorophosphate (0.13 mL, 0.89 mmol) was added dropwise via syringe turning the reaction golden. The reaction was stirred at −78° C. for 1 h, and then was warmed to −20° C. and poured into sat'd aq ammonium chloride solution (5 mL). The aqueous layer was separated and extracted with Et$_2$O (2×). The combined organic layers were washed with brine, dried

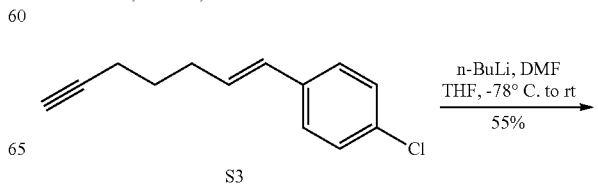

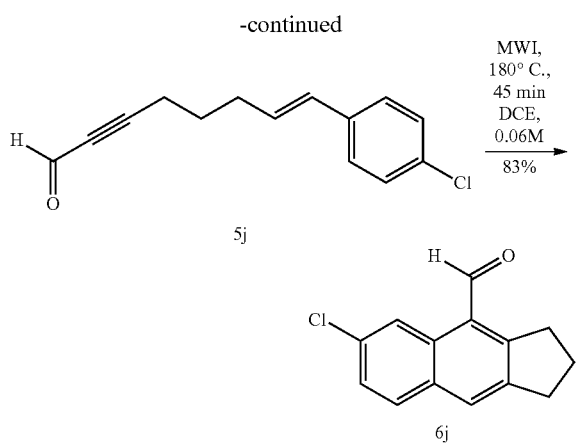

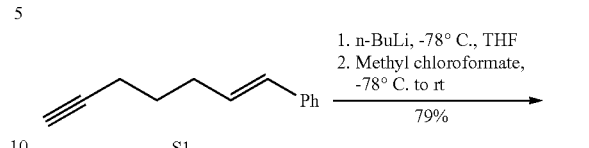

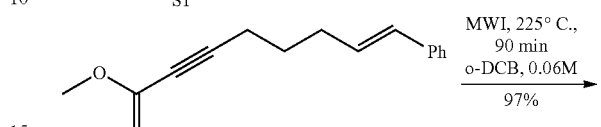

<sup>13</sup>C NMR (100 MHz, CDCl$_3$) 192.0, 153.4, 143.9, 134.2, 131.5, 130.6, 129.3, 128.7, 127.2, 126.8, 124.6, 123.9, 31.7, 31.4, 25.7 ppm

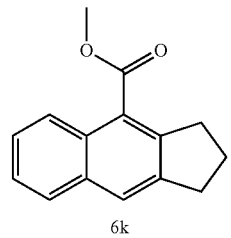

(E)-Methyl 8-phenyloct-7-en-2-ynoate (5k). (Michaelides, I. N.; Darses, B.; Dixon, D. J. *Org. Lett.* 2011, 13, 664.) To a flame-dried two-neck 10 mL round-bottomed flask equipped with an argon inlet adapter, a septum, and a stir bar was added enyne S1 (0.250 g, 1.47 mmol) and THF (3 mL) via syringe. The solution was cooled at −78° C. (bath temperature) in a dry ice/acetone bath, and n-butyllithium (1.0 mL of a 1.6 M solution in hexanes, 1.62 mmol) was added dropwise turning the reaction purple. The reaction was stirred at −78° C. for 45 min, then methyl chloroformate (0.15 mL, 1.91 mmol) was added dropwise via syringe turning the reaction yellow. The reaction was stirred for 1 h at −78° C., then warmed to rt over 3 h. The reaction was quenched with sat'd aq ammonium chloride, and the aqueous layer was separated. The aqueous layer was extracted with Et$_2$O (2×), and the combined organic layers were washed with brine, dried over magnesium sulfate, gravity filtered, and concentrated under reduced pressure. The crude product was purified by silica gel column chromatography (25 g silica cartridge, 2-10% ethyl acetate/hexanes) to yield product 5k as a colorless oil (0.263 g, 79%).

Data for 5k (LSK-3-052)

<sup>1</sup>H NMR (400 MHz, CDCl$_3$) 7.34 (t, J=7.6 Hz, 2H), 7.30 (d, J=7.6 Hz, 2H), 7.21 (t, J=7.6 Hz, 1H), 6.44 (d, J=16.1 Hz, 1H), 6.18 (dt, J=7.1, 16.1 Hz, 1H), 3.78 (s, 3H), 2.40 (t, J=7.2 Hz, 2H), 2.35 (q, J=7.2 Hz, 2H), 1.78 (p, J=7.2 Hz, 2H) ppm <sup>13</sup>C NMR (100 MHz, CDCl$_3$) 154.2, 137.5, 131.2, 128.9, 128.6 (2C), 127.1, 126.1 (2C), 89.4, 73.3, 52.6, 31.9, 27.1, 18.1 ppm IR (thin film) 3084, 3051, 3025, 2949, 2863, 2831, 2235, 1712, 1597, 1492, 1254, 748 cm$^{-1}$ LRMS (TOF MS ES+) m/z (%): 229 (93), 228 (15), 227 (10), 197 (41), 196 (51), 170 (27), 169 (100)

HRMS (TOF MS ES+) [M+H]$^+$ calcd for C$_{15}$H$_{17}$O$_2$, 229.1229; found, 229.1228

(E)-8-(4-Chlorophenyl)oct-7-en-2-ynal (5j). To a flame-dried two-neck 10 mL round-bottomed flask equipped with an argon inlet adapter, a septum, and a stir bar was added enyne S3 (0.203 g, 1.00 mmol) and THF (2.7 mL) via syringe. The solution was cooled at −78° C. (bath temperature) in a dry ice/acetone bath, and n-butyllithium (0.63 mL, 1.00 mmol) was added dropwise via syringe turning the reaction brown. The reaction was stirred at −78° C. for 30 min, and N,N-dimethylformamide (0.15 mL, 2.00 mmol) was added dropwise via syringe turning the reaction colorless. The reaction was stirred at −78° C. for 30 min, and was then warmed to rt and stirred for 2 h. The reaction was added to a cold solution of ethyl acetate (3 mL) and 10% KH$_2$PO$_4$ (6 mL) and stirred for 30 min. The aqueous layer was separated and the organic layer was washed with brine, dried over magnesium sulfate, gravity filtered, and concentrated under reduced pressure. The crude product was purified by silica gel column chromatography (10 g silica cartridge, 0-10% ethyl acetate/hexanes) to yield product 5j as a colorless oil (0.128 g, 55%).

Data for 5j (LSK-4-028)

<sup>1</sup>H NMR (300 MHz, CDCl$_3$) 9.19 (s, 1H), 7.27 (s, 4H), 6.39 (d, J=15.9 Hz, 1H), 6.15 (dt, J=6.6, 15.9 Hz, 1H), 2.48 (t, J=6.9 Hz, 2H), 2.35 (q, J=7.2 Hz, 2H), 1.80 (p, J=7.2 Hz, 2H) ppm <sup>13</sup>C NMR (100 MHz, CDCl$_3$) 177.0, 135.8, 132.5, 129.9, 129.4, 128.5, 127.1, 98.4, 81.9, 31.7, 26.9, 18.4 ppm

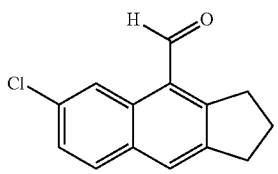 [SMILES: O=Cc1c2c(cc3ccc(Cl)cc13)CCC2]

6-Chloro-2,3-dihydro-1H-cyclopenta[b]naphthalene-4-carbaldehyde (6j). To a 2-5 mL microwave irradiation vial equipped with a stir bar was added enyne 5j (0.035 g, 0.15 mmol) in DCE (2.5 mL). The reaction was irradiated with stirring at 180° C. for 45 min until complete by TLC. The reaction turned golden in color. The reaction was then transferred to a vial, concentrated under reduced pressure, and dried under vacuum to yield naphthalene 6j as a golden sticky solid (0.029 g, 83%).

Data for 6j (LSK-4-015)

<sup>1</sup>H NMR (300 MHz, CDCl$_3$) 10.75 (s, 1H), 9.19 (s, 1H), 7.87 (s, 1H), 7.73 (d, J=8.4 Hz, 1H), 7.44 (d, J=9.0 Hz, 1H), 3.47 (t, J=7.2 Hz, 2H), 3.08 (q, J=6.6 Hz, 2H), 2.25 (p, J=7.2 Hz, 2H) ppm

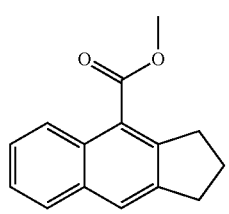 [SMILES: COC(=O)c1c2c(cc3ccccc13)CCC2]

Methyl 2,3-dihydro-1H-cyclopenta[b]naphthalene-4-carboxylate (6k). To a 10-20 mL microwave irradiation vial equipped with a stir bar was added enyne 5k (0.150 g, 0.66 mmol) in o-dichlorobenzene (11 mL). The reaction was irradiated with stirring at 225° C. for 90 min until complete by TLC. The reaction turned golden in color. The reaction was then transferred to a vial and concentrated under high vacuum to yield naphthalene 6k as a black oil (0.144 g, 97%).

Data for 6k (LSK-3-087)

$^1$H NMR (300 MHz, CDCl$_3$) 8.24 (d, J=8.2 Hz, 1H), 7.78 (d, J=8.2 Hz, 1H), 7.77 (s, 1H), 7.46 (dp, J=1.3, 8.2 Hz, 2H), 4.03 (s, 3H), 3.21 (t, J=7.4 Hz, 2H), 3.08 (dt, J=1.0, 7.4 Hz, 2H), 2.15 (p, J=7.4 Hz, 2H) ppm $^{13}$C NMR (100 MHz, CDCl$_3$) 169.2, 144.9, 143.0, 133.1, 129.9, 127.9, 126.2, 125.7, 125.4, 125.1, 124.6, 51.9, 33.4, 32.6, 25.8 ppm IR (thin film) 3051, 3002, 2950, 2835, 1609, 1716, 1228 cm$^{-1}$ LRMS (TOF MS EI+) m/z (%): 227 (5), 195 (10), 166 (22), 83 (100), 82 (74), 70 (65), 62 (61)

HRMS (TOF MS ES+) [M] calcd for C$_{15}$H$_{14}$O$_2$, 226.0994; found, 226.0998

3.5 h until complete by TLC, followed by addition of Et$_2$O (25 mL) and silica gel (10 g). The suspension was stirred for 30 min, filtered through a pad of silica gel with Et$_2$O washings, and then concentrated under reduced pressure to yield the aldehyde xx as a yellow oil (0.478 g, 81%). The crude product was carried on without further purification. Compound S11 was previously characterized.

(E)-Oct-1-en-7-yn-1-ylbenzene (S12). To a flame-dried two-neck 25 mL round-bottomed flask equipped with a reflux condenser, an argon inlet adapter, a septum, and a stir bar was added sodium hydride (0.399 g of a 60% dispersion in oil, 9.98 mmol). The flask was flushed with argon, and THF (12 mL) was added via syringe with stirring. Diethyl benzylphosphonate (1.90 mL, 9.11 mmol) in THF (6 mL) was added dropwise over 5 min via syringe, and the reaction was stirred for 15 min at rt. Aldehyde S11 (0.478 g, 4.34 mmol) in THF (6 mL) was added dropwise over 5 min via syringe, turning the reaction from cloudy white to light yellow. The reaction was heated at reflux for 4 h until it was complete by TLC. The reaction turned dark brown in color while refluxing. Once the reaction was complete by TLC, it was cooled to rt and quenched with sat'd aq ammonium chloride causing precipitation of tan solids. The aqueous layer was separated and extracted with Et$_2$O (2×). The combined organic layers were washed with brine, dried over magnesium sulfate, gravity filtered, and concentrated under reduced pressure to yield a crude yellow oil. The crude product was purified by silica gel column chromatography (25 g silica cartridge, 0-25% ethyl acetate/hexanes) to yield enyne 512 as a yellow oil (0.157 g, 20%).

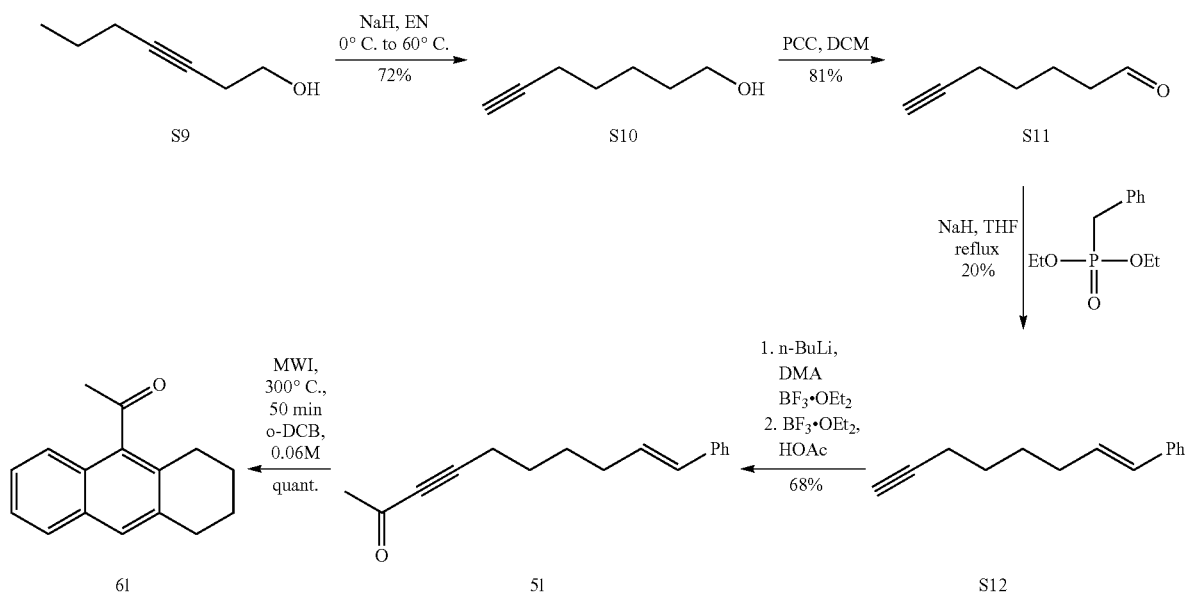

Literature Preparation. The preparation of hept-6-yn-1-ol (S10) from hept-3-yn-1-ol (S9) followed the procedure reported by Curran, et al. *J. Org. Chem.* 2010, 75, 2942.

Hept-6-ynal (S11). To a one-neck 50 mL round-bottomed flask equipped with a septum pierced with a needle and a stir bar, was added pyridinium chlorochromate (2.31 g, 10.7 mmol) and DCM (20 mL) with stirring. Alcohol S10 (0.600 g, 5.35 mmol) was added all at once via syringe, and the reaction turned dark brown and thick. The reaction was stirred at rt for

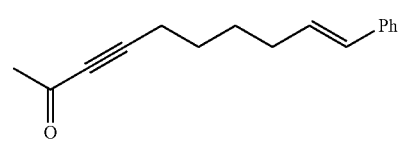 [SMILES: CC(=O)C#CCCCC/C=C/c1ccccc1]

(E)-10-Phenyldec-9-en-3-yn-2-one (5l). Follows general procedure A: enyne S12 (0.132 g, 0.72 mmol), THF (2 mL), n-butyllithium (0.41 mL of a 1.6 M solution in hexanes, 0.66 mmol), N,N-dimethylacetamide (56 µL, 0.60 mmol), THF (2 mL), boron trifluoride diethyl etherate (0.1 mL, 0.75 mmol), and acetic acid (43 µL, 0.75 mmol). The reaction was complete after 3 h. After addition of the amide the reaction turned yellow. The crude product was purified by silica gel column chromatography (10 g silica cartridge, 0-10% ethyl acetate/hexanes) to yield the product 5l as a colorless oil (0.093 g, 68%).

Data for 5l (LSK-3-123)

$^1$H NMR (300 MHz, CDCl$_3$) 7.37-7.30 (m, 4H), 7.21 (t, J=7.0 Hz, 1H), 6.41 (d, J=15.9 Hz, 1H), 6.20 (dt, J=6.7, 15.9 Hz, 1H), 2.40 (t, J=6.4 Hz, 2H), 2.33 (s, 3H), 2.26 (q, J=6.6 Hz, 2H), 1.70-1.58 (m, 4H) ppm color. The reaction was then transferred to a vial and concentrated under high vacuum to yield naphthalene 6l as a brown oil (0.044 g, quant.).

Data for 6l (LSK-3-141)

$^1$H NMR (300 MHz, CDCl$_3$) 7.78-7.73 (m, 1H), 7.59 (s, 1H), 7.56-7.52 (m, 1H), 7.44-7.38 (m, 2H), 3.02-3.98 (m, 2H), 2.86-2.82 (m, 2H), 2.63 (s, 3H), 1.90-1.86 (m, 4H) ppm $^{13}$C NMR (100 MHz, CDCl$_3$) 209.0, 138.7, 135.9, 131.8, 130.5, 127.8, 127.6, 127.3, 125.9, 125.4, 123.6, 32.9, 30.1, 27.0, 23.0, 22.8 ppm IR (thin film) 3055, 2933, 2859, 2831, 1698, 1596, 1498 cm$^{-1}$ LRMS (ASAP MSMS) m/z (%): 224 (100), 225 (81), 210 (12), 209 (49)

HRMS (TOF MS ES+) [M+H]$^+$ calcd for C$_{16}$H$_{17}$O, 225.1279; found, 225.1282

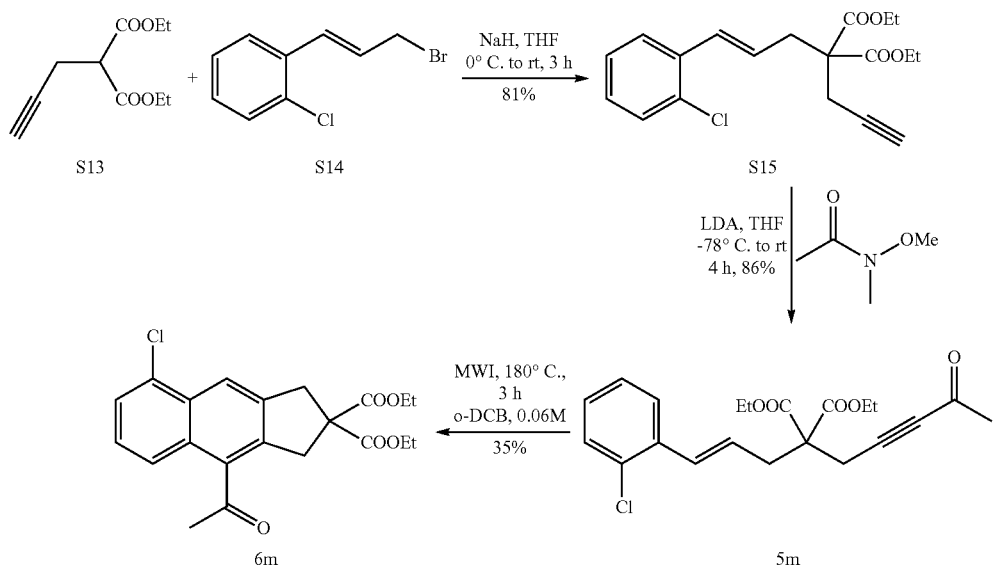

$^{13}$C NMR (100 MHz, CDCl$_3$) 185.0, 137.6, 130.4, 130.1, 128.5 (2C), 127.0, 126.0 (2C), 93.8, 81.6, 32.8, 32.4, 28.5, 27.2, 18.8 ppm IR (thin film) 3085, 3056, 3025, 2935, 2859, 2210, 1674, 1598, 1493, 745 cm$^{-1}$ LRMS (TOF MS ES+) m/z (%): 227 (100), 226 (52), 211 (10), 209 (12), 183 (9)

HRMS (TOF MS ES+) [M+H]$^+$ calcd for C$_{16}$H$_{19}$O, 227.1436; found, 227.1420

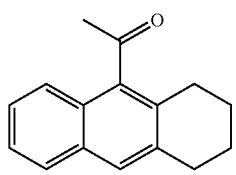 [SMILES: CC(=O)c1c2c(cc3ccccc13)CCCC2]

1-(1,2,3,4-Tetrahydroanthracen-9-yl)ethanone (6l). To a 10 mL microwave irradiation vial equipped with a stir bar was added enyne 5l (0.042 g, 0.19 mmol) in o-dichlorobenzene (3.1 mL). The reaction was irradiated with stirring at 300° C. for 50 min in an Anton Parr Monowave 300 microwave reactor until complete by TLC. The reaction turned light brown in Literature Preparation. Diethyl 2-(prop-2-yn-1-yl)malonate (S13) was prepared from triethyl methanetricarboxylate through a procedure previously reported by Brummond et al., *J. Am. Chem. Soc.* 2002, 124, 15186. (E)-1-(3-Bromoprop-1-en-1-yl)-2-chlorobenzene (S14) was prepared from 2-chlorobenzaldehyde via the procedure reported by Fering a, et al. *Adv. Synth. Catal.* 2004, 346, 413.

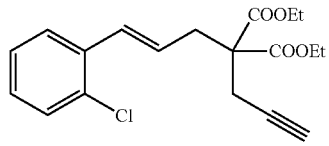 [SMILES: C#CCC(C/C=C/c1ccccc1Cl)(C(=O)OCC)C(=O)OCC]

Diethyl 2-(3-(2-chlorophenyl)allyl)-2-(prop-2-yn-1-yl) malonate (S15). An oven-dried, 100 mL three-necked round-bottomed flask under a nitrogen atmosphere was charged with diethyl 2-(prop-2-yn-1-yl)malonate S13 (1.8 g, 9.1 mmol), (E)-1-(3-bromoprop-1-en-1-yl)-2-chlorobenzene S14 (2.1 g, 11.0 mmol), and THF (60 mL). The solution was cooled to 0° C. in an ice bath for 15 min, then NaH (0.43 g of a 60% dispersion in mineral oil, 11.0 mmol) was added in one portion. The solution was stirred at 0° C. for 2 h. The consumption of the starting material was monitored by TLC (AcOEt/n-hexane 0.5:9.5). The reaction was then quenched with sat'd aq ammonium chloride solution (70 mL). The layers were separated and the aqueous phase was extracted with AcOEt (3×50 mL). The combined organic layers were dried over Na$_2$SO$_4$, gravity filtered, and concentrated under reduced pressure. The reaction residue was purified by silica gel flash chromatography, eluting with AcOEt/n-hexane 0.5:9.5, to provide 2.55 g of the title compound as a yellow oil in 81% yield.

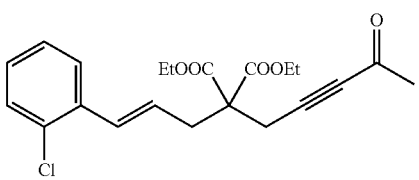 [SMILES: CCOC(=O)C(CC#CC(C)=O)(C/C=C/c1ccccc1Cl)C(=O)OCC]

Diethyl 2-(3-(2-chlorophenyl)allyl)-2-(4-oxopent-2-yn-1-yl)malonate (5m). An oven-dried 100 mL three-necked round-bottomed flask under a nitrogen atmosphere was charged with compound enyne S15 (0.5 g, 1.4 mmol) and THF (20 mL). The solution was cooled to −78° C. in a dry ice/acetone bath for 15 min, then LDA (0.7 mL of 2.0 M heptane/THF/ethylbenzene solution, 1.4 mmol) was added via syringe. The mixture was stirred at −78° C. for 1 h, then N-methoxy-N-methylacetamide (0.16 mL, 1.54 mmol) was added. The solution was warmed to rt and was stirred for 4 h. The consumption of the starting material was monitored by TLC (AcOEt/n-hexane 1:9). The reaction was quenched by adding sat'd aq ammonium chloride solution (40 mL). The layers were separated and the aqueous phase was extracted with ether (3×30 mL). The combined organic layers were dried over Na$_2$SO$_4$, gravity filtered, and concentrated under reduced pressure. The reaction residue was purified by silica gel flash chromatography, eluting with AcOEt/n-hexane 2:8, to provide 0.47 g of the title compound as a colorless oil in 86% yield.

Data for 5m (EB-079)
$^1$H NMR (400 MHz, CDCl$_3$) 7.53 (d, J=7.2 Hz, 1H), 7.39 (t, J=7.7 Hz, 1H), 7.36-7.14 (m, 2H), 6.98 (d, J=15.6 Hz, 1H), 6.11 (dt, J=15.6, 7.6 Hz, 1H), 4.33 (q, J=7.1 Hz, 4H), 3.11 (s, 2H), 3.07 (d, J=7.6 Hz, 2H), 2.40 (s, 3H), 1.36 (t, J=7.1 Hz, 6H) ppm
$^{13}$C NMR (100 MHz, CDCl$_3$) 183.9, 169.2 (2C), 134.9, 132.7, 131.3, 129.6, 128.7, 126.9, 126.9, 125.9, 87.7, 83.6, 62.1 (2C), 56.8, 36.3, 32.9, 23.4, 14.1 (2C) ppm
IR (thin film) 2982, 2936, 2213, 1734, 1679, 1203 cm$^{-1}$
HRMS (TOF MS ES+) [M+H]$^+$ calcd for C$_{21}$H$_{24}$O$_5$Cl, 391.1312; found, 391.1299

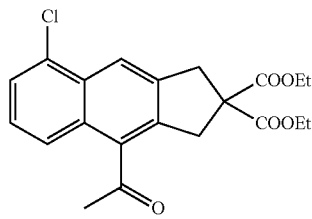 [SMILES: CCOC(=O)C1(C(=O)OCC)Cc2cc3c(Cl)cccc3c(C(C)=O)c2C1]

Diethyl 4-acetyl-8-chloro-1H-cyclopenta[b]naphthalene-2,2(3H)-dicarboxylate (6m). A microwave irradiation vial (10-20 mL) was equipped with a sir bar (1.5 cm) and was charged with compound 5m (0.3 g, 0.77 mmol) and 1,2-dichlorobenzene (12.8 mL). The reaction was irradiated with stirring at 180° C. for 30 min, turning gold in color. The reaction was directly added to a silica gel column, which was eluted with n-hexane to separate the 1,2-dichlorobenzene and then AcOEt/n-hexane 2:8 to collect the pure product. The title compound was isolated as a yellow oil in quant. yield (0.298 g). Small traces of contaminants were observed.

Data for 6m (EB-081)
$^1$H NMR (400 MHz, CDCl$_3$) 8.17 (s, 1H), 7.67 (d, J=8.5 Hz, 1H), 7.53 (d, J=7.4 Hz, 1H), 7.35 (t, J=8.0 Hz, 1H), 4.27-4.17 (m, 4H), 3.76 (s, 2H), 3.68 (s, 2H), 2.66 (s, 3H), 1.38-1.13 (m, 6H)
$^{13}$C NMR (100 MHz, CDCl$_3$) 205.0, 170.9 (2C), 140.5, 136.7, 135.4, 132.3, 130.7, 130.0, 126.3, 126.3, 123.7, 121.0, 62.1 (2C), 60.9, 40.1, 39.4, 32.3, 14.1 (2C)
IR (thin film) 2981, 2935, 1731, 1697, 1253, 1185 cm$^{-1}$
HRMS (TOF MS ES+) [M+H]$^+$ calcd for C$_{21}$H$_{22}$O$_5$Cl, 389.1156; found, 389.1166

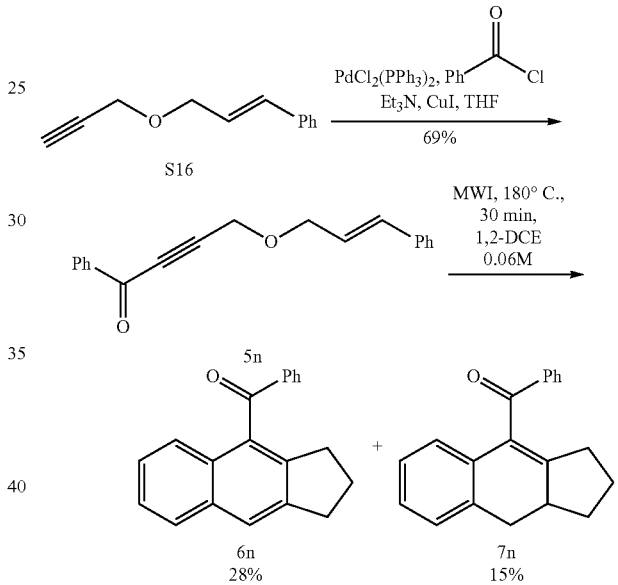

Literature Preparation. The preparation of (E)-(3-(prop-2-yn-1-yloxy)prop-1-en-1-yl)benzene (S16) followed the procedure reported by Lee et al. *Org. Lett.* 2002, 4, 4369.

4-(Cinnamyloxy)-1-phenylbut-2-yn-1-one (5n). To a flame-dried two-neck 50 mL round-bottomed flask equipped with an argon inlet adapter, a septum, and a stir bar was added PdCl$_2$(PPh$_3$)$_2$ (0.024 g, 0.034 mmol), THF (6 mL), triethylamine (0.29 mL, 2.06 mmol), and benzoyl chloride (0.24 mL, 2.06 mmol). The solution was stirred for 10 min at rt, and copper(I) iodide (0.013 g, 0.069 mmol) was added all at once through the sidearm turning the reaction from cloudy yellow to clear orange. The reaction was stirred for 10 min, and enyne S16 (0.296 g, 1.72 mmol) in THF (0.5 mL) was added all at once via syringe. The reaction was stirred for 4 h until complete by TLC, in which time the reaction became cloudy and orange. Water was added to the reaction, and the aqueous layer was separated and extracted with EtOAc (2×). The combined organic layers were washed with 1 M hydrochloric acid, sat'd aq ammonium chloride, and brine, dried over magnesium sulfate, gravity filtered, and concentrated under reduced pressure. The crude product was purified by silica gel column chromatography (50 g silica cartridge, 0-10% ethyl acetate/hexanes) to yield product 5n as a yellow oil (0.330 g, 69%).

Data for 5n (LSK-3-096)

$^1$H NMR (400 MHz, CDCl$_3$) 8.16 (d, J=7.5 Hz, 2H), 7.64 (t, J=7.5 Hz, 1H), 7.50 (t, J=7.5 Hz, 2H), 7.42 (d, J=7.5 Hz, 2H), 7.34 (t, J=7.5 Hz, 2H), 7.27 (t, J=7.5 Hz, 1H), 6.70 (d, J=16.0 Hz, 1H), 6.23 (dt, J=6.2, 16.0 Hz, 1H), 4.51 (s, 2H), 4.35 (dd, J=1.2, 6.2 Hz, 2H) ppm $^{13}$C NMR (100 MHz, CDCl$_3$) 177.5, 136.4, 136.3, 143.4, 134.0, 129.7 (2C), 128.7 (2C), 128.7 (2C), 128.1, 126.6 (2C), 124.5, 90.3, 84.2, 70.9, 57.1 ppm IR (thin film) 3076, 3059, 3027, 2933, 2850, 2226, 1645, 1596, 1493, 1262, 745 cm$^{-1}$ LRMS (TOF MSMS ES+) m/z (%): 276 (39), 275 (100), 258 (9), 257 (22), 245 (8)

HRMS (TOF MS ES+) [M+H]$^+$ calcd for C$_{19}$H$_{17}$O$_2$, 277.1229; found 277.1216 with a stir bar was added enyne 5n (0.054 g, 0.20 mmol) in DCE (3.3 mL). The reaction was irradiated with stirring at 180° C. for 30 min to yield a mixture of products 6n, 7n, and other unidentified byproducts, as observed by crude $^1$H NMR spectroscopy. The crude mixture was purified by silica gel column chromatography (10 g silica cartridge, 0-15% ethyl acetate/hexanes) to yield 6n (0.015 g, 28%) and 7n (0.008 g, 15%).

Data for 6n (LSK-3-022-001, 28% yield)

$^1$H NMR (400 MHz, CDCl$_3$) 7.90 (d, J=8.3 Hz, 1H), 7.82 (d, J=8.3 Hz, 3H), 7.68 (d, J=8.3 Hz, 1H), 7.62 (t, J=7.5 Hz, 1H), 7.51-7.38 (m, 4H), 5.26 (s, 2H), 5.01 (s, 2H) ppm $^{13}$C NMR (125 MHz, CDCl$_3$) 197.9, 138.0, 137.4, 137.3, 134.0, 133.4, 130.5, 129.9 (2C), 129.2, 128.9 (2C), 128.4, 126.7, 126.2, 125.6, 121.5 72.7, 72.3 ppm IR (thin film) 3061, 3019, 2921, 2852, 1765, 1662, 1578, 1233, 1055, 751 cm$^{-1}$ LRMS (TOF MSMS ES+) m/z (%): 274 (100), 273 (80), 259 (71), 245 (41), 231 (45)

HRMS (TOF MS ES+) [M] calcd for C$_{19}$H$_{14}$O$_2$, 274.0994, found: 274.0957

Data for 7n (LSK-3-022-002, 15% yield)

$^1$H NMR (400 MHz, CDCl$_3$) 7.82 (d, J=7.2 Hz, 2H), 7.56 (d, J=7.2 Hz, 1H), 7.44 (t, J=7.6 Hz, 3H), 7.27-7.23 (m, 1H), 7.16 (t, J=7.2 Hz, 1H), 7.06 (t, J=7.6 Hz, 1H), 6.86 (d, J=7.6 Hz, 1H), 4.69 (dd, J=1.6, 16.0 Hz, 1H), 4.44 (t, J=8.4 Hz, 1H), 4.32 (dd, J=2.8, 16.0 Hz, 1H), 3.59 (t, J=8.8 Hz, 1H), 3.25-3.17 (m, 1H), 3.00 (dd, J=6.4, 14.8 Hz, 1H), 2.83 (t, J=15.2 Hz, 1H) ppm $^{13}$C NMR (125 MHz, CDCl$_3$) 196.9, 150.5, 137.0, 133.9, 133.4, 129.9, 129.6 (2C), 128.9, 128.7 (2C), 128.2, 127.6, 127.0, 126.0, 74.0, 69.5, 41.1, 31.5 ppm IR (thin film) 3061, 3025, 2921, 2851, 1723, 1663, 1595, 1449, 1230, 1042 cm$^{-1}$ LRMS (TOF MSMS ES+) m/z (%): 277 (5), 276 (100), 275 (40), 261 (25), HRMS (TOF MS ES+) [M] calcd for C$_{19}$H$_{16}$O$_2$, 276.1150; found, 276.1126

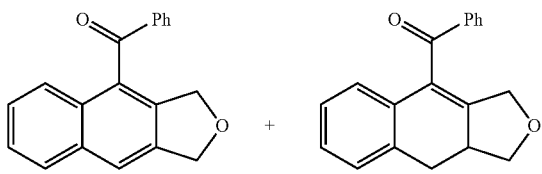 [SMILES: O=C(c1ccccc1)c1c2c(cc3ccccc13)COC2 ; O=C(C1=C2COCC2Cc2ccccc21)c1ccccc1]

1-(1,3-Dihydronaphtho[2,3-c]furan-4-yl)ethanone (6n) and 1-(1,3,9,9a-tetrahydronaphtho[2,3-c]furan-4-yl)ethanone (7n). To a 2-5 mL microwave irradiation vial equipped

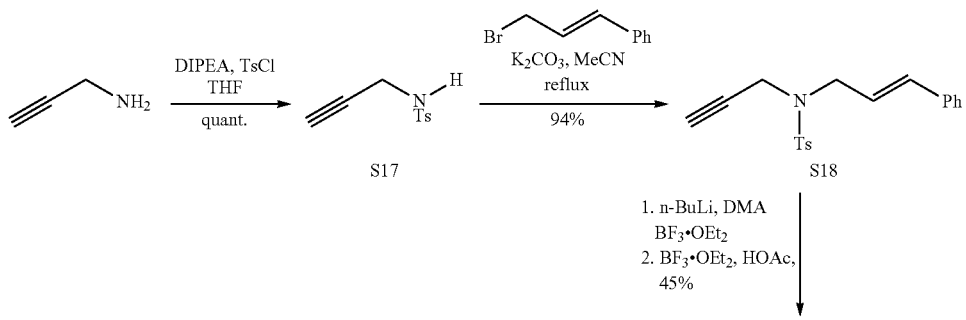

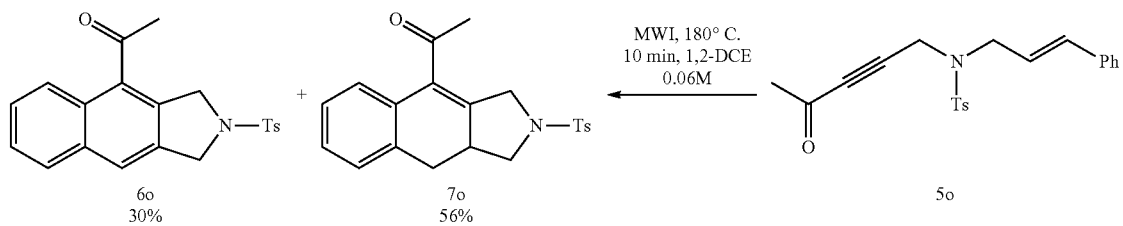

Literature Preparation. The preparation of 4-methyl-N-(prop-2-yn-1-yl)benzenesulfonamide (S17) followed the procedure reported by Gilbertson et al., *J. Org. Chem.* 2007, 72, 799.

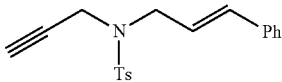 [SMILES: C#CCN(C/C=C/c1ccccc1)S(=O)(=O)c1ccc(C)cc1]

N-Cinnamyl-4-methyl-N-(prop-2-yn-1-yl)benzene-sulfonamide (S18). (Sylvester, et al. *J. Am. Chem. Soc.* 2009, 131, 8772) To a flame-dried two-neck 100 mL round-bottomed flask equipped with an argon inlet adapter, a septum, and a stir bar was added alkyne S17 (1.30 g, 6.22 mmol) and anhydrous potassium carbonate (3.44 g, 24.9 mmol). The flask was flushed with argon, and then MeCN (65 mL) was added with stirring. Cinnamyl bromide (1.84 mL, 12.4 mmol) was added dropwise, turning the reaction yellow. The reaction was heated at reflux for 18 h, and then cooled to rt. The MeCN was then removed by concentration under reduced pressure. The residue was taken up in sat'd aq sodium bicarbonate and extracted with Et$_2$O (3×). The combined organic layers were washed with brine, dried over magnesium sulfate, gravity filtered, and concentrated under reduced pressure. The crude product was purified by silica gel column chromatography (50 g silica cartridge, 0-20% ethyl acetate/hexanes) to yield the enyne S18 as a light yellow solid (1.90 g, 94%), previously characterized (Gibson, et al. *Chem. Eur. J.* 2007, 13, 709).

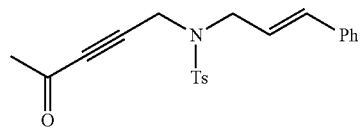 [SMILES: CC(=O)C#CCN(C/C=C/c1ccccc1)S(=O)(=O)c1ccc(C)cc1]

N-Cinnamyl-4-methyl-N-(prop-2-yn-1-yl)benzene-sulfonamide (5o). Follows general procedure A: enyne S18 (1.25 g, 3.84 mmol), THF (10 mL), n-butyllithium (2.2 mL of a 1.6 M solution in hexanes, 2.55 mmol), N,N-dimethylacetamide (0.27 mL, 2.96 mmol), THF (10 mL), boron trifluoride diethyl etherate (0.46 mL, 3.69 mmol), and acetic acid (0.21 mL, 3.69 mmol). The reaction turned purple and then golden after the addition of n-butyllithium, and orange after the addition of acetic acid. The reaction was complete after 3 h. The crude product was purified by silica gel column chromatography (100 g silica cartridge, 0-30% ethyl acetate/hexanes) to yield the product 5o as a white solid (0.485 g, 45% yield).

Data for 5o (LSK-3-017)

$^1$H NMR (400 MHz, CDCl$_3$) 7.78 (d, J=7.9 Hz, 2H), 7.38-7.28 (m, 7H), 6.57 (d, J=15.8 Hz, 1H), 6.09 (dt, J=6.9, 15.8 Hz, 1H), 4.28 (s, 2H), 4.00 (d, J=6.9 Hz, 2H), 2.44 (s, 3H), 2.11 (s, 3H) ppm $^{13}$C NMR (100 MHz, CDCl$_3$) 183.3, 144.1, 135.9, 135.6, 135.4, 129.8 (2C), 128.7 (2C), 128.3, 127.8 (2C), 126.6 (2C), 122.5, 84.8, 84.3, 49.3, 36.1, 32.4, 21.6 ppm IR (thin film) 3060, 3028, 2921, 2859, 2255, 2209, 1679, 1597, 1494, 1349, 1222, 1162, 755, 736 cm$^{-1}$ LRMS (TOF MS ES+) m/z (%): 367 (7), 366 (20), 365 (31), 364 (100), 352 (12), 198 (15), 195 (63), 155 (25)

HRMS (TOF MS ES+) [M+H]$^+$ calcd for C$_{21}$H$_{22}$NO$_3$S, 368.1276, found: 368.1309

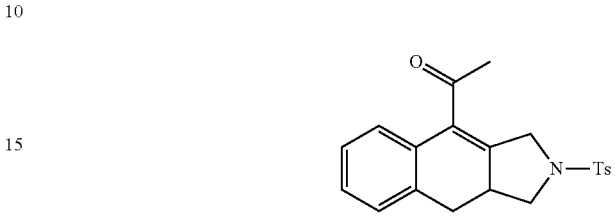

1-(2-Tosyl-2,3-dihydro-1H-benzo[f]isoindol-4-yl)ethanone (6o) and 1-(2-Tosyl-2,3,9,9a-tetrahydro-1H-benzo[f]isoindol-4-yl)ethanone (7o). To a 2-5 mL microwave irradiation vial equipped with a stir bar was added enyne 5o (0.051 g, 0.14 mmol) in DCE (2.3 mL). The reaction was irradiated with stirring at 180° C. for 10 min to yield the products 6o and 7o (0.044 g, 86%). Based on $^1$H NMR analysis the ratio of 6o to 7o was 1:1.8. Naphthalene 6o was not separable from dihydronaphthalene 7o by column chromatography, but enough of each product was separated by HPLC (15% ethyl acetate/hexanes) for characterization.

Data for 6o (LSK-3-022-001, 30% yield by $^1$H NMR)

$^1$H NMR (400 MHz, CDCl$_3$) 7.86-7.80 (m, 4H), 7.71 (s, 1H), 7.55-7.48 (m, 2H), 7.33 (d, J=8.2 Hz, 2H), 4.74 (s, 2H), 4.71 (s, 2H), 2.67 (s, 3H), 2.40 (s, 3H) ppm $^{13}$C NMR (100 MHz, CDCl$_3$) 203.9, 144.0, 134.8, 133.6, 133.4, 133.1, 132.9, 129.9 (2C), 128.9, 128.6, 127.8 (2C), 127.2, 126.5, 124.6, 123.7, 52.8, 52.8, 32.0, 21.5 ppm IR (thin film) 3060, 2949, 2919, 2851, 1680, 1625, 1593, 1491, 1346, 1160, 1094, 816, 767 cm$^{-1}$ LRMS (TOF MS ES+) m/z (%): 366 (33), 196 (8), 197 (100)

HRMS (TOF MS ES+) [M+H]$^+$ calcd for C$_{21}$H$_{20}$NO$_3$S, 366.1164, found: 366.1147

Data for 7o (LSK-3-022-002, 56% yield by $^1$H NMR)

$^1$H NMR (400 MHz, CDCl$_3$) 7.76 (d, J=8.0 Hz, 2H), 7.35 (d, J=8.0 Hz, 2H), 7.24-7.17 (m, 3H), 7.10 (d, J=6.9 Hz, 1H), 4.54 (dd, J=1.7, 17.9 Hz, 1H), 3.96 (t, J=8.9 Hz, 1H), 3.91 (dd, J=2.5, 17.9 Hz, 1H), 2.97 (m, 1H), 2.87 (t, J=9.6 Hz, 1H), 2.83 (dd, J=6.2, 14.8 Hz, 1H), 2.52 (t, J=14.8 Hz, 1H), 2.44 (s, 3H), 2.34 (s, 3H) ppm $^{13}$C NMR (100 MHz, CDCl$_3$) 200.8, 147.9, 143.9, 134.5, 132.9, 132.0 (2C), 129.9 (2C), 128.1, 127.9, 127.8 (2C), 127.1, 125.6, 52.9, 51.7, 40.1, 32.3, 30.0, 21.6 ppm IR (thin film) 3056, 2945, 2916, 2851, 1680, 1593, 1499, 1344, 1160, 1094, 817, 751 cm$^{-1}$ LRMS (TOF MS ES+) m/z (%): 368 (100), 197 (92), 194 (8), 185 (12), 184 (8)

HRMS (TOF MS ES+) [M+H]$^+$ calcd for C$_{21}$H$_{22}$NO$_3$S, 368.1320; found, 368.1349

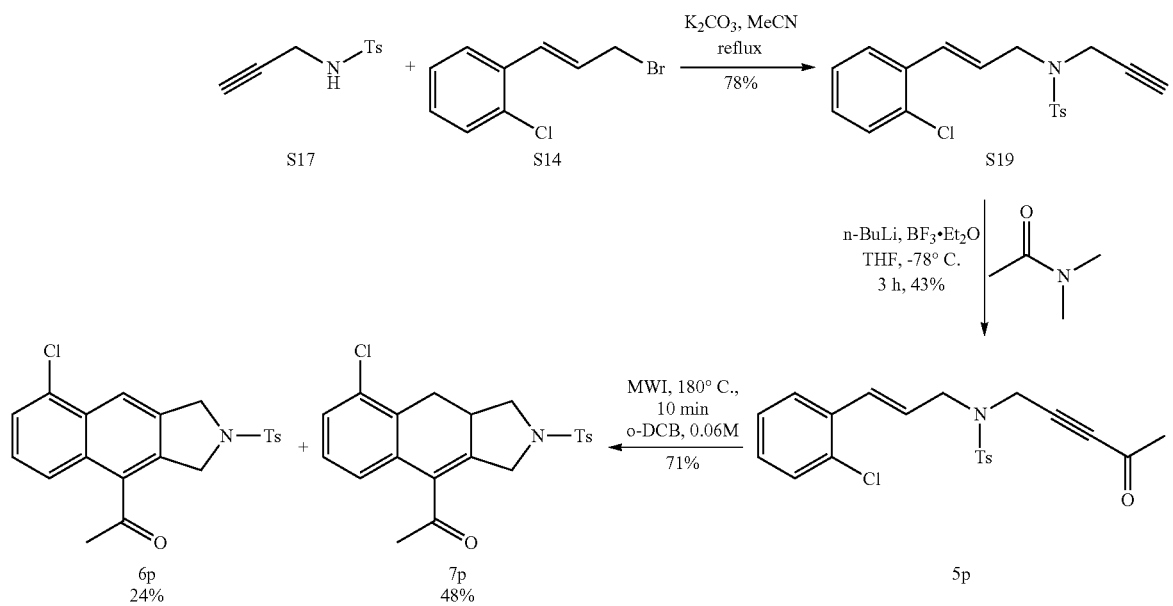

N-(3-(2-Chlorophenyl)allyl)-4-methyl-N-(prop-2-yn-1-yl)benzene sulfonamide (S19). To an oven-dried, 100 mL three-necked round-bottomed flask equipped with a stir bar, two septa and a nitrogen inlet adaptor was added 4-methyl-N-(prop-2-yn-1-yl)benzenesulfonamide (S17) (1.0 g, 4.8 mmol) and potassium carbonate (2.69 g, 19.2 mmol). The flask was evacuated and refilled with nitrogen three times, then MeCN (60 mL) was added. (E)-1-(3-Bromoprop-1-en-1-yl)-2-chlorobenzene (S14) (1.66 g, 7.2 mmol) was added dropwise via syringe, turning the solution dark yellow. The mixture was heated at reflux and stirred overnight. The consumption of the starting material was monitored by TLC (AcOEt/n-hexane 1:9). The solvent was removed in vacuo, and the reaction residue was taken up in sat'd NaHCO$_3$ solution (70 mL) and extracted with ether (3×50 mL). The combined organic layers were washed with brine (70 mL), dried over Na$_2$SO$_4$, gravity filtered, and concentrated under reduced pressure. The reaction residue was purified by silica gel flash chromatography, eluting with AcOEt/n-hexane 1:9, to provide 1.35 g of the title compound as a light yellow solid in a 78% yield.

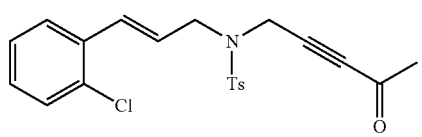 [SMILES: CC(=O)C#CCN(C/C=C/c1ccccc1Cl)S(=O)(=O)c1ccc(C)cc1]

N-(3-(2-Chlorophenyl)allyl)-4-methyl-N-(4-oxopent-2-yn-1-yl)benzene sulfonamide (5p). An oven-dried, 100 mL three-necked round-bottomed flask under a nitrogen atmosphere was charged with compound S19 (1.0 g, 2.8 mmol) and THF (40 mL). The solution was cooled to −78° C. in a dry ice/acetone bath for 15 min, then n-BuLi (1.74 mL of a 1.6 M n-hexane solution, 2.8 mmol) was added via syringe. The mixture was stirred at −78° C. for 1 h, then N,N-dimethylacetamide (0.19 mL, 2.1 mmol) and BF$_3$.Et$_2$O (0.26 mL, 2.1 mmol) were added. The solution was stirred at −78° C. for an additional 3 h. The consumption of the starting material was monitored by TLC (AcOEt/n-hexane 3:7). The reaction was quenched by adding sat'd aq ammonium chloride solution (50 mL). The layers were separated and the aqueous phase was extracted with ether (3×30 mL). The combined organic layers were dried over Na$_2$SO$_4$, gravity filtered, and concentrated under reduced pressure. The reaction residue was purified by silica gel flash chromatography, eluting with AcOEt/n-hexane 2:8, to provide 0.48 g of the title compound as a light yellow solid in a 43% yield.

$^1$H NMR (400 MHz, CDCl$_3$) 7.76 (d, J=8.2 Hz, 2H), 7.53-7.40 (m, 1H), 7.35-7.31 (m, 3H), 7.28-7.10 (m, 2H), 6.96 (d, J=15.7 Hz, 1H), 6.07 (dt, J=15.7, 6.8 Hz, 1H), 4.28 (s, 2H), 4.02 (d, J=6.7 Hz, 2H), 2.43 (s, 3H), 2.11 (s, 3H) ppm $^{13}$C NMR (100 MHz, CDCl$_3$) 183.2, 144.3, 135.5, 134.2, 133.2, 131.6, 129.9 (2C), 129.8, 129.4, 127.9 (2C), 127.2, 127.1, 125.6, 84.9, 84.2, 49.5, 36.4, 32.5, 21.6 ppm IR (thin film) 2920, 2209, 1679, 1351, 1162 cm$^{-1}$ HRMS (TOF MS ES+) [M+H]$^+$ calcd for C$_{21}$H$_{21}$NO$_3$SCl: 402.0931; found, 402.0951

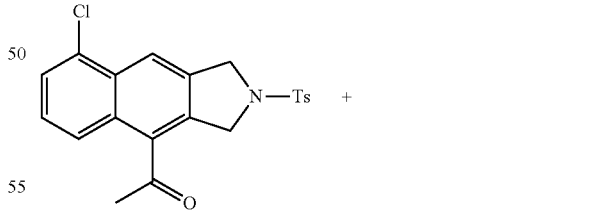

1-(8-Chloro-2-tosyl-2,3-dihydro-1H-benzo[f]isoindol-4-yl)ethanone (6p) and 1-(8-chloro-2-tosyl-2,3,9,9a-tetrahydro-1H-benzo[f]isoindol-4-yl)ethanone (7p). A microwave irradiation vial (2-5 mL) was equipped with a sir bar (1 cm) and was charged with compound 5p (0.07 g, 0.17 mmol) and 1,2-dichlorobenzene (3 mL). The reaction was irradiated with stirring at 180° C. for 10 min, turning brown in color. The reaction was directly added to a silica gel column, which was eluted with n-hexane to separate the 1,2-dichlorobenzene, and then AcOEt/n-hexane 2:8 to collect the pure products. The title compounds 6p and 7p were isolated as a 1:2 mixture of inseparable products in a 71% yield (0.048 g).

Data for 6p, 7p (EB-067)

$^1$H NMR (400 MHz, CDCl$_3$) 8.18 (s, 1H minor) 7.80-7.71 (m, 3H major and 3H minor), 7.59 (d, J=7.4 Hz, 1H minor), 7.47-7.23 (m, 3H major and 2H minor), 7.16 (t, J=7.8 Hz, 1H major), 7.00 (d, J=7.6 Hz, 1H major), 4.77 (s, 2H minor), 4.70 (s, 2H minor), 4.55 (d, J=18.0 Hz, 1H major), 4.10 (m, 1H major), 3.99 (t, J=8.1 Hz, 1H major), 3.90 (d, J=18.0 Hz, 1H major), 3.38 (dd, J=15.4, 6.1 Hz, 1H major), 3.04-2.79 (m, 2H major), 2.65 (s, 3H minor), 2.43 (s, 3H major), 2.39 (s, 3H minor), 2.31 (s, 3H major) ppm $^{13}$C NMR (100 MHz, CDCl$_3$) 203.6 (minor), 200.3 (major), 148.6 (major), 144.2 (minor), 144.1 (major), 136.4 (minor), 134.2 (minor), 134.0 (major), 133.6 (1C major and 1C minor), 133.1 (major), 132.9 (1C minor and 1C major), 132.7 (major), 132.5 (minor), 130.9 (minor), 130.2 (minor), 130.1 (2C minor), 130.0 (2C major), 129.1 (2C major), 127.9 (major), 127.8 (2C minor), 127.8 (major), 127.0 (minor), 126.9 (minor), 124.2 (major), 123.8 (minor), 120.2 (minor), 53.1 (minor), 52.8 (minor), 51.7 (major), 39.6 (major), 32.1 (minor), 30.1 (major), 28.6 (major), 21.7 (minor), 21.6 (major), 14.3 (major).

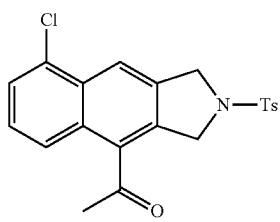 [SMILES: CC(=O)c1c2c(cc3c(Cl)cccc13)CN(S(=O)(=O)c1ccc(C)cc1)C2]

1-(8-Chloro-2-tosyl-2,3-dihydro-1H-benzo[f]isoindol-4-yl)ethanone (6p). A microwave irradiation vial (10-20 mL) was equipped with a sir bar and was charged with compound 5p (0.3 g, 0.75 mmol) and 1,2-dichlorobenzene (12.4 mL). The reaction was irradiated with stirring at 180° C. for 3 h, turning black in color. The solution was directly added to a silica gel column, which was eluted with n-hexane to separate the 1,2-dichlorobenzene, and then AcOEt/n-hexane 2:8 to collect the pure product. The title compound was isolated as a brown solid in a 31% yield (0.093 g).

$^1$H NMR (400 MHz, CDCl$_3$) 8.13 (s, 1H), 7.78 (d, J=8.2 Hz, 2H), 7.70 (d, J=8.5 Hz, 1H), 7.56 (d, J=7.3 Hz, 1H), 7.39 (t, J=8.0 Hz, 1H), 7.32 (d, J=8.0 Hz, 2H), 4.73 (s, 2H), 4.69 (s, 2H), 2.63 (s, 3H), 2.38 (s, 3H).

$^{13}$C NMR (100 MHz, CDCl$_3$) 203.6, 144.2, 136.3, 134.1, 133.5, 133.1, 132.6, 130.9, 130.2, 130.0 (2C), 127.8 (2C), 127.0, 126.9, 123.8, 120.2, 53.1, 52.8, 32.1, 21.6.

IR (thin film) 2921, 1691, 1346, 1160 cm$^{-1}$

HRMS (TOF MS ES+) [M–H]$^+$ calcd for C$_{21}$H$_{17}$NO$_3$SCl: 398.0618; found, 398.0609

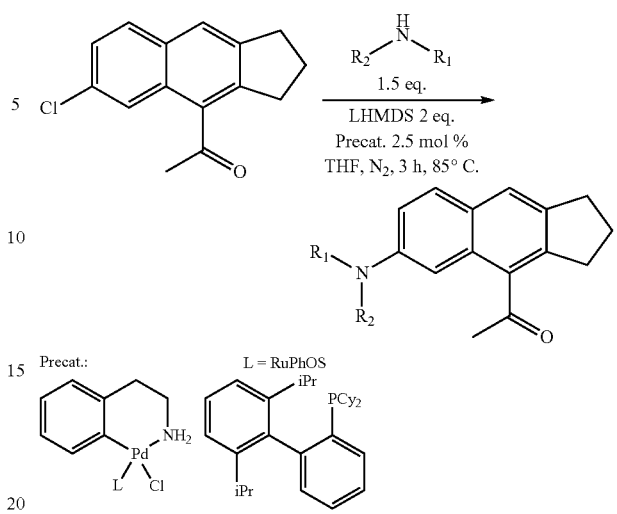

General Procedure for the Buchwald-Hartwig Couplings

An oven-dried sealed tube (0.5-2 mL) was equipped with a sir bar and charged with the precatalyst (0.004 mmol). The tube was closed with a septum, then evacuated and refilled with nitrogen three times through a needle. LHMDS (1M solution in THF, 0.32 mmol) and compound LSK-3-97 (0.16 mmol) in dry THF (0.3 mL) were added. Finally the amine (0.24 mmol) in dry THF (0.3 mL) was added at room temperature. The resulting solution was heated at 85° C. in an oil bath and stirred for 3 hours. The consumption of the starting material was monitored by TLC. At the end of the reaction, the mixture was cooled to room temperature, diluted with saturated aqueous ammonium chloride solution (10 mL), and then extracted with AcOEt (3×12 mL). The combined organic layers were dried over Na$_2$SO$_4$, gravity filtered and concentrated in vacuo. The crude product was finally purified by flash chromatography over silica gel.

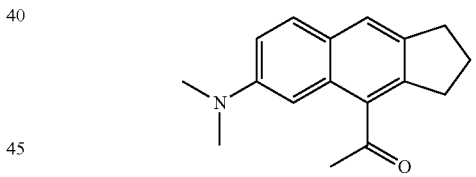

1-(6-(Dimethylamino)-2,3-dihydro-1H-cyclopenta[b]naphthalen-4-yl)ethanone (8). An oven-dried sealed tube (0.5-2 mL) was equipped with a stir bar and charged with the precatalyst (0.003 g, 0.004 mmol). The tube was closed with a septum, then evacuated and refilled with nitrogen three times through a needle. LHMDS (0.3 mL of a 1.0 M solution in THF, 0.32 mmol) and compound 6b (0.038 g, 0.16 mmol) in THF (0.3 mL) were added via syringe. Finally, dimethylamine (0.3 mL of a 2.0 M solution in THF, 0.24 mmol) in THF (0.3 mL) was added at rt via syringe. The resulting solution was heated at 85° C. in an oil bath and stirred for 3 h. The consumption of the starting material was monitored by TLC. Once the reaction was complete, the mixture was cooled rt, diluted with sat'd aq ammonium chloride solution (10 mL), and then extracted with AcOEt (3×12 mL). The combined organic layers were dried over Na$_2$SO$_4$, gravity filtered, and concentrated in vacuo. The crude product was purified by flash chromatography (n-hexane/AcOEt 9.25:0.7) and the pure product was isolated as a yellow solid (70% yield).

$^1$H NMR (400 MHz, CDCl$_3$) 7.64 (d, J=9.0 Hz, 1H), 7.56 (s, 1H), 7.11 (dd, J=9.1, 2.5 Hz, 1H), 6.87 (d, J=2.5 Hz, 1H), 3.16-2.87 (m, 10H), 2.65 (s, 3H), 2.12 (p, J=7.3 Hz, 2H) ppm $^{13}$C NMR (100 MHz, CDCl$_3$) 207.0, 148.8, 140.5, 138.9, 133.0, 130.1, 128.9, 126.6, 124.1, 115.8, 103.5, 40.9 (2C), 32.5, 32.2, 32.0, 26.2 ppm IR (thin film) 2952, 2917, 2849, 2359, 2339, 1685, 1620, 1510, 1344 cm$^{-1}$ HRMS (TOF MS ES+) [M] calcd for C$_{17}$H$_{20}$NO: 254.1545; found, 254.1536

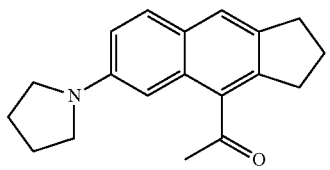 [SMILES: CC(=O)c1c2c(cc3ccc(N4CCCC4)cc13)CCC2]

Synthesis of 1-(6-(pyrrolidin-1-yl)-2,3-dihydro-1H-cyclopenta[b]naphthalen-4-yl)ethanone EB-013

Substrate EB-013 was synthesized following the general procedure for the Buchwald-Hartwig couplings: precatalyst (0.003 g, 0.004 mmol), LHMDS (0.3 mL of a 1M solution in THF, 0.32 mmol), LSK-3-97 (0.038 g, 0.16 mmol), pyrrolidine (0.017 g, 0.02 mL, 0.24 mmol) dry THF (0.3 mL). The title compound was isolated (n-hexane/AcOEt 9:1, 59% yield) as a yellow solid.

$^1$H NMR (400 MHz, CDCl$_3$) δ 7.62 (d, J=9.0 Hz, 1H), 7.54 (s, 1H), 6.94 (dd, J=8.9, 2.6 Hz, 1H), 6.69 (s, 1H), 3.48-3.20 (m, 4H), 2.99 (q, J=6.8 Hz, 4H), 2.65 (s, 3H), 2.24-1.87 (m, 6H) ppm $^{13}$C NMR (100 MHz, CDCl$_3$) δ 207.1, 146.1, 140.6, 138.0, 132.6, 130.4, 129.1, 126.1, 124.1, 115.1, 101.9, 47.9, 32.5, 32.2, 31.9, 29.8, 26.2, 25.6 (2CH$_2$) ppm IR (thin film) 2957, 2919, 2841, 1680, 1618, 1509, 1353 cm$^{-1}$ HRMS TOF MS ES+: C$_{19}$H$_{22}$NO Calculated: 280.1701; Found: 280.1713

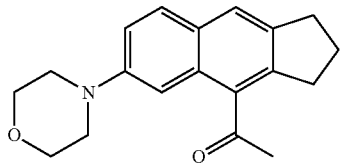 [SMILES: CC(=O)c1c2c(cc3ccc(N4CCOCC4)cc13)CCC2]

Synthesis of 1-(6-morpholino-2,3-dihydro-1H-cyclopenta[b]naphthalen-4-yl)ethanone (EB-014)

Substrate EB-014 was synthesized following the general procedure for the Buchwald-Hartwig couplings: precatalyst (0.003 g, 0.004 mmol), LHMDS (0.3 mL of a 1M solution in THF, 0.32 mmol), LSK-3-97 (0.038 g, 0.16 mmol), morpholine (0.021 g, 0.02 mL, 0.24 mmol) dry THF (0.3 mL). The title compound was isolated (n-hexane/AcOEt 8:2, 58% yield) as a yellow solid.

$^1$H NMR (400 MHz, CDCl$_3$) δ 7.67 (d, J=9.0 Hz, 1H), 7.60 (s, 1H), 7.22-7.14 (m, 1H), 7.10 (s, 1H), 3.90 (t, J=4.7 Hz, 4H), 3.36-3.13 (m, 4H), 3.02 (td, J=8.7, 8.0, 5.9 Hz, 4H), 2.64 (s, 3H), 2.14 (p, J=7.3 Hz, 2H) ppm $^{13}$C NMR (100 MHz, CDCl$_3$) δ 206.7, 146.1, 140.7, 138.0, 133.6, 129.6, 129.0, 128.4, 124.2, 118.2, 107.2, 67.0 (2CH$_2$), 49.8, 32.5, 32.3, 32.2, 26.3 (2CH$_2$) ppm IR (thin film) 2956, 2919, 2850, 1689, 1618, 1227, 1121 cm$^{-1}$ HRMS TOF MS ES+: C$_{19}$H$_{22}$NO$_2$ Calculated: 296.1651; Found: 296.1636

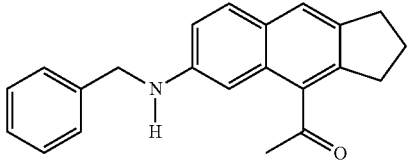 [SMILES: CC(=O)c1c2c(cc3ccc(NCc4ccccc4)cc13)CCC2]

Synthesis of 1-(6-(benzylamino)-2,3-dihydro-1H-cyclopenta[b]naphthalen-4-yl)ethanone (EB-016)

Substrate EB-016 was synthesized following the general procedure for the Buchwald-Hartwig couplings: precatalyst (0.003 g, 0.004 mmol), LHMDS (0.3 mL of a 1M solution in THF, 0.32 mmol), LSK-3-97 (0.038 g, 0.16 mmol), phenylmethanamine (0.026 g, 0.026 mL, 0.24 mmol) dry THF (0.3 mL). The title compound was isolated (n-hexane/AcOEt 8.5:1.5, 89% yield) as a yellow oil.

$^1$H NMR (400 MHz, CDCl$_3$) δ 7.67-7.46 (m, 2H), 7.45-7.31 (m, 4H), 7.31-7.16 (m, 1H), 6.87 (dd, J=8.8, 2.4 Hz, 1H), 6.75 (d, J=2.3 Hz, 1H), 4.40 (s, 3H), 2.98 (t, J=7.3 Hz, 4H), 2.47 (s, 3H), 2.11 (p, J=7.3 Hz, 2H) ppm $^{13}$C NMR (100 MHz, CDCl$_3$) δ 206.9, 145.8, 140.6, 139.1, 139.0, 132.9, 130.2, 129.2, 128.8 (2CH), 127.7 (2CH), 127.4, 127.3, 124.3, 117.1, 102.4, 48.4, 32.4, 32.2, 31.9, 26.2 ppm IR (thin film) 3408, 3027, 2951, 2841, 1684, 1626, 1522, 1256 cm$^{-1}$ HRMS TOF MS ES+: C$_{22}$H$_{22}$NO Calculated: 316.1701; Found: 316.1690

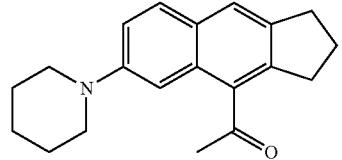 [SMILES: CC(=O)c1c2c(cc3ccc(N4CCCCC4)cc13)CCC2]

Synthesis of 1-(6-(piperidin-1-yl)-2,3-dihydro-1H-cyclopenta[b]naphthalen-4-yl)ethanone (EB-019)

Substrate EB-019 was synthesized following the general procedure for the Buchwald-Hartwig couplings: precatalyst (0.003 g, 0.004 mmol), LHMDS (0.3 mL of a 1M solution in THF, 0.32 mmol), LSK-3-97 (0.038 g, 0.16 mmol), piperidine (0.02 g, 0.024 mL, 0.24 mmol) dry THF (0.3 mL). The title compound was isolated (n-hexane/AcOEt 9:1, 45% yield) as a yellow oil.

$^1$H NMR (400 MHz, CDCl$_3$) δ 7.64 (d, J=9.0 Hz, 1H), 7.57 (s, 1H), 7.32-7.17 (m, 1H), 7.08 (s, 1H), 3.32-3.11 (m, 4H), 3.01 (td, J=7.2, 3.1 Hz, 4H), 2.64 (s, 3H), 2.13 (p, J=7.3 Hz, 2H), 1.87-1.67 (m, 4H), 1.69-1.51 (m, 2H) ppm $^{13}$C NMR (100 MHz, CDCl$_3$) δ 206.9, 150.6, 140.3, 140.1, 133.5, 129.8, 128.7, 128.0, 124.0, 119.5, 107.4, 51.0 (2CH$_2$), 32.4, 32.3, 32.2, 26.3, 26.0 (2CH$_2$), 24.4 ppm IR (thin film) 2932, 2851, 2803, 1690, 1613, 1503, 1234 cm$^{-1}$ HRMS TOF MS ES+: C$_{20}$H$_{24}$NO Calculated: 294.1858; Found: 294.1871

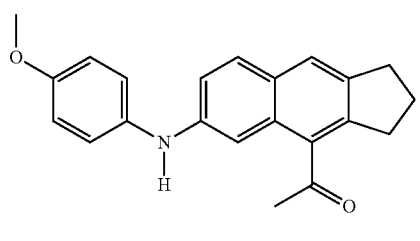 [SMILES: COc1ccc(Nc2ccc3cc4c(c(C(C)=O)c3c2)CCC4)cc1]

Synthesis of 1-(6-((4-methoxyphenyl)amino)-2,3-dihydro-1H-cyclopenta[b]naphthalen-4-yl)ethanone (EB-020)

Substrate EB-020 was synthesized following the general procedure for the Buchwald-Hartwig couplings: precatalyst (0.003 g, 0.004 mmol), LHMDS (0.3 mL of a 1M solution in THF, 0.32 mmol), LSK-3-97 (0.038 g, 0.16 mmol), 4-methoxyaniline (0.029 g, 0.24 mmol), dry THF (0.6 mL). The title compound was isolated (n-hexane/AcOEt 8:2, 71% yield) as a brown solid.

$^1$H NMR (400 MHz, CDCl$_3$) δ 7.69-7.52 (m, 2H), 7.18 (s, 1H), 7.15-7.03 (m, 3H), 6.88 (d, J=8.8 Hz, 2H), 5.75 (s, 1H), 3.81 (s, 3H), 3.01 (dd, J=9.6, 4.9 Hz, 4H), 2.58 (s, 3H), 2.12 (p, J=7.3 Hz, 2H) ppm $^{13}$C NMR (100 MHz, CDCl$_3$) δ 206.5, 155.6, 143.1, 140.9, 139.9, 135.5, 133.0, 130.0, 129.3, 128.3, 124.36 (2CH), 122.3, 118.0, 114.8 (2CH), 106.5, 55.7, 32.5, 32.3, 32.1, 26.2 ppm IR (thin film) 3369, 2953, 2836, 1683, 1624, 1508, 1241 cm$^{-1}$ HRMS TOF MS ES+: C$_{22}$H$_{22}$NO$_2$ Calculated: 332.1651; Found: 332.1648

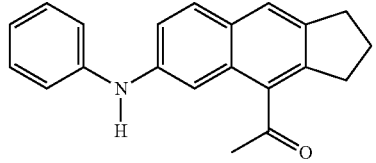 [SMILES: CC(=O)c1c2c(cc3ccc(Nc4ccccc4)cc13)CCC2]

Synthesis of 1-(6-(phenylamino)-2,3-dihydro-1H-cyclopenta[b]naphthalen-4-yl)ethanone (EB-030)

Substrate EB-030 was synthesized following the general procedure for the Buchwald-Hartwig couplings: precatalyst (0.02 g, 0.003 mmol), LHMDS (0.22 mL of a 1M solution in THF, 0.22 mmol), LSK-3-97 (0.027 g, 0.11 mmol), aniline (0.015 g, 0.015 mL, 0.16 mmol) dry THF (0.3 mL). The title compound was isolated (n-hexane/AcOEt 8:2, 78% yield) as a yellow solid.

$^1$H NMR (400 MHz, CDCl$_3$) δ 7.68 (d, J=8.8 Hz, 1H), 7.62 (s, 1H), 7.36 (s, 1H), 7.33-7.19 (m, 3H), 7.12 (d, J=7.7 Hz, 2H), 6.96 (t, J=7.3 Hz, 1H), 5.89 (s, 1H), 3.03 (t, J=7.1 Hz, 4H), 2.61 (s, 3H), 2.14 (p, J=7.3 Hz, 2H) ppm $^{13}$C NMR (100 MHz, CDCl$_3$) δ 206.3, 142.9, 141.2, 140.9, 140.7, 133.3, 129.8, 129.5 (2CH), 129.3, 128.9, 124.3, 121.50, 119.3, 118.1 (2CH), 109.3, 32.5, 32.3, 32.2, 26.2 ppm IR (thin film) 3361, 2953, 1680, 1624, 1596, 1497, 1397 cm$^{-1}$ HRMS TOF MS ES+: C$_{21}$H$_{19}$NO Calculated: 301.1467; Found: 301.1468

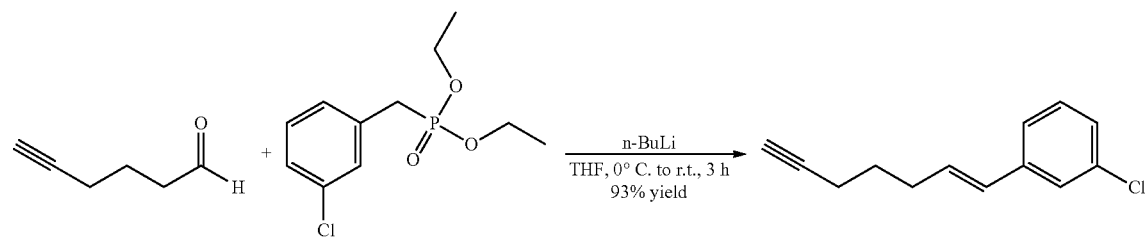

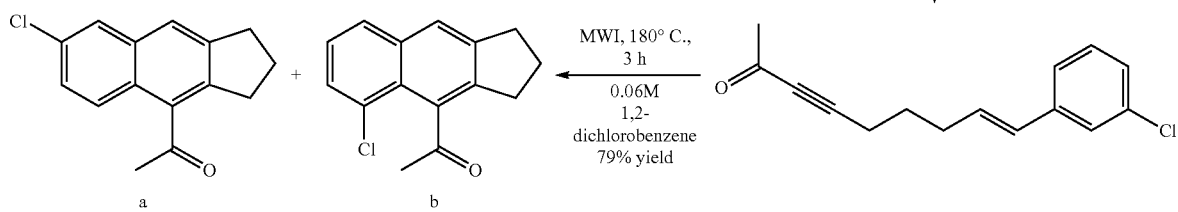

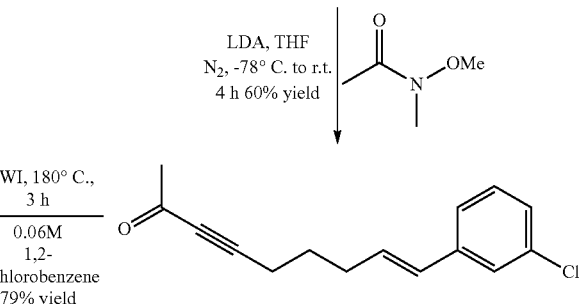

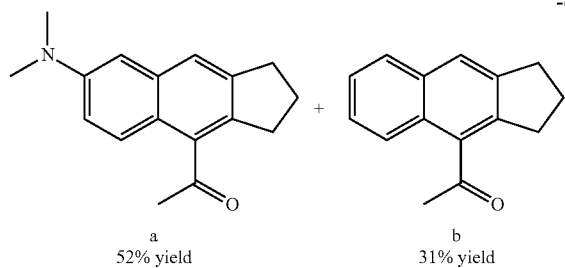

a
52% yield b
31% yield

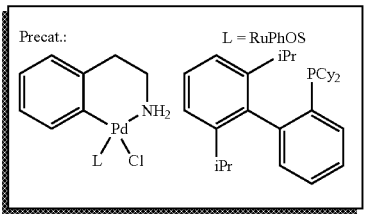

Literature Preparation. 5-Hexynal was prepared from 5-hexyn-1-ol through an oxidation reaction with PCC, which was reported by Kobayashi et al. *Chem. Asian J.* 2007, 2, 135-144. Diethyl 3-chlorobenzylphosphonate was prepared from 1-(bromomethyl)-3-chlorobenzene and triethyl phosphite via the procedure reported by Luscombe et al. *Macromolecules* 2011, 44, 512-520.

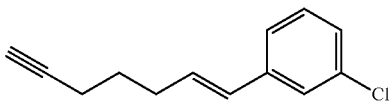

Synthesis of 1-chloro-3-(hept-1-en-6-yn-1-yl)benzene (EB-024)

An oven-dried 250 mL three-necked round-bottomed flask under a nitrogen atmosphere was charged with 3-chlorobenzylphosphonate (4.74 g, 18 mmol) and dry THF (60 mL). The solution was cooled to 0° C. in an ice bath for 15 min, then n-BuLi (12 mL of a 1.6 M n-hexane solution, 19 mmol) was added dropwise over 10 min, via syringe. The mixture was stirred at 0° C. for 30 min, then 5-hexynal (1.0 g, 10 mmol) in dry THF (40 mL) was added. The solution was warmed to room temperature and was stirred for 3 h. The consumption of the starting material was monitored by TLC (AcOEt/n-hexane 1:9). The reaction was quenched by adding saturated aqueous ammonium chloride solution (70 mL). The layers were separated and the aqueous phase was extracted with ether (3×50 mL). The combined organic layers were washed with brine (2×50 mL), dried over $Na_2SO_4$, gravity filtered and concentrated under reduced pressure. The reaction residue was purified by silica gel flash chromatography, eluting with AcOEt/n-hexane 0.5:9.5, to provide 1.9 g of the title compound as a colorless oil in a 93% yield.

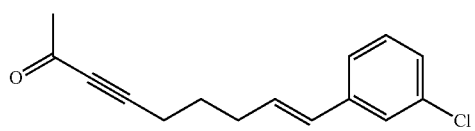 [SMILES: CC(=O)C#CCCC/C=C/c1cccc(Cl)c1]

Synthesis of 9-(3-chlorophenyl)non-8-en-3-yn-2-one (EB-026)

An oven-dried 100 mL three-necked round-bottomed flask under a nitrogen atmosphere was charged with compound EB-024 (0.7 g, 3.4 mmol) and dry THF (40 mL). The solution was cooled to −78° C. in a dry ice/acetone bath for 15 min, then LDA (2 mL of a 2 M heptane/THF/ethylbenzene solution, 4.0 mmol) was added via syringe. The mixture was stirred at −78° C. for 1 h, then N-methoxy-N-methylacetamide (0.39 g, 0.4 mL, 3.7 mmol) was added. The solution was warmed to room temperature and was stirred for 4 h. The consumption of the starting material was monitored by TLC (AcOEt/n-hexane 2:8). The reaction was quenched by adding saturated aqueous ammonium chloride solution (70 mL). The layers were separated and the aqueous phase was extracted with ether (3×50 mL). The combined organic layers were dried over $Na_2SO_4$, gravity filtered and concentrated under reduced pressure. The reaction residue was purified by silica gel flash chromatography, eluting with AcOEt/n-hexane 1.5:8.5, to provide 0.52 g of the title compound as a colorless oil in a 60% yield.

$^1$H NMR (400 MHz, $CDCl_3$) δ 7.33 (s, 1H), 7.19 (td, J=7.6, 7.2, 2.2 Hz, 3H), 6.37 (d, J=15.8 Hz, 1H), 6.31-6.04 (m, 1H), 2.42 (t, J=7.1 Hz, 2H), 2.34 (d, J=8.9 Hz, 5H), 1.76 (p, J=7.2 Hz, 2H) ppm $^{13}$C NMR (100 MHz, $CDCl_3$) δ 184.9, 139.4, 134.6, 130.7, 130.0, 129.9, 127.2, 126.0, 124.4, 93.4, 81.9, 32.9, 32.0, 27.3, 18.5 ppm IR (thin film) 2934, 2210, 1674, 1229, 964 $cm^{-1}$ HRMS TOF MS ES+: $C_{15}H_{16}ClO$ Calculated: 247.0890; Found: 247.0886

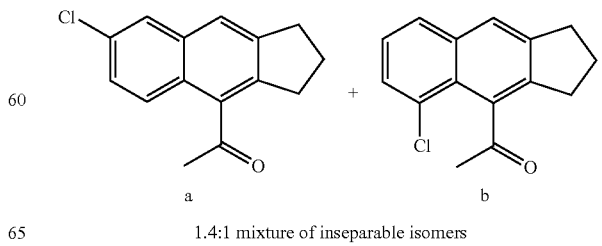

a     b 1.4:1 mixture of inseparable isomers

Synthesis of 1-(5-chloro-2,3-dihydro-1H-cyclopenta[b]naphthalen-4-yl)ethanone (EB-028-A) and 1-(7-chloro-2,3-dihydro-1H-cyclopenta[b]naphthalen-4-yl)ethanone (EB-028-B)

A microwave irradiation vial was equipped with a sir bar and was charged with compound EB-026 (0.2 g, 0.81 mmol) and 1,2-dichlorobenzene (13.5 mL). The reaction was irradiated with stirring at 180° C. for 3 h, turning gold in color. The solution was directly charged into a silica gel column, which was eluted with n-hexane separate the 1,2-dichlorobenzene and then AcOEt/n-hexane 1:9 to collect the pure products. The title compounds were isolated as a 1.4:1 mixture of unseparable isomers in a 79% yield.

$^1$H NMR (400 MHz, CDCl$_3$) δ 7.73-7.58 (m, 2H major isomer and 2H minor isomer), 7.53 (s, 1H major isomer), 7.44 (d, J=7.4 Hz, 1H minor isomer), 7.35-7.21 (m, 1H major isomer and 1H minor isomer), 3.02-2.97 (m, 4H major isomer and 4H minor isomer), 2.60 (s, 3H, minor isomer), 2.59 (s, 3H, major isomer), 2.14-2.06 (m, 2H major isomer and 2H minor isomer) ppm $^{13}$C NMR (100 MHz, CDCl$_3$) δ 206.7 (minor isomer), 205.5 (major isomer), 144.6 (major isomer), 144.0 (major isomer), 141.3 (minor isomer), 140.3 (major isomer), 135.1 (major isomer), 134.7 (minor isomer), 134.6 (1C major isomer and 1C minor isomer), 133.9 (major isomer), 131.2 (major isomer), 129.4 (minor isomer), 127.7 (minor isomer), 127.5 (major isomer), 126.7 (major isomer), 126.7 (minor isomer), 126.3 (minor isomer), 126.0 (major isomer), 125.4 (minor isomer), 124.0 (minor isomer), 123.4 (major isomer), 33.7 (minor isomer), 32.4 (minor isomer), 32.4 (major isomer), 32.2 (major isomer), 32.1 (major isomer), 31.6 (minor isomer), 26.1 (major isomer), 25.8 (minor isomer) ppm IR (thin film) 2949, 1969, 1598, 1418, 1142 cm$^{-1}$ HRMS TOF MS ES+: C$_{15}$H$_{14}$ClO Calculated: 245.0733; Found: 245.0728

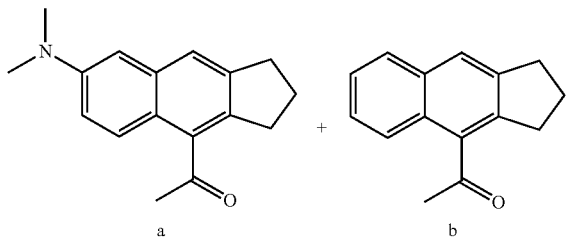

a     b

Synthesis of 1-(7-(dimethylamino)-2,3-dihydro-1H-cyclopenta[b]naphthalen-4-yl)ethanone (EB-041-A) and 1-(2,3-dihydro-1H-cyclopenta[b]naphthalen-4-yl)ethanone (EB-041-B)

Substrates EB-041-A and EB-041-B were synthesized from EB-028-A and EB-028-B respectively, following the general procedure for the Buchwald-Hartwig couplings. Compound EB-041-A was isolated (n-hexane/AcOEt 9.5:0.5, 52% yield) as a yellow oil. Compound EB-041-B was isolated as colorless oil in a 39% yield and was previously characterized (2.21a/LSK-3-046).

$^1$H NMR (400 MHz, CDCl$_3$) δ 7.68 (d, J=9.3 Hz, 1H), 7.54 (s, 1H), 7.11 (dd, J=9.3, 2.5 Hz, 1H), 6.88 (d, J=2.1 Hz, 1H), 3.03 (s, 6H), 3.02-2.95 (m, 4H), 2.63 (s, 3H), 2.12 (p, J=7.3 Hz, 2H).

$^{13}$C NMR (100 MHz, CDCl$_3$) δ 206.6, 148.3, 143.5, 136.0, 134.9, 134.5, 125.3, 122.9, 121.7, 116.4, 106.9, 40.9 (2CH$_3$), 32.6, 32.3, 32.1, 26.3.

IR (thin film) 2949, 2842, 2799, 1687, 1624, 1612, 1509, 1356, 1208, 1143 cm$^{-1}$ HRMS TOF MS ES+: C$_{17}$H$_{19}$NO Calculated: 253.1467; Found: 253.1471

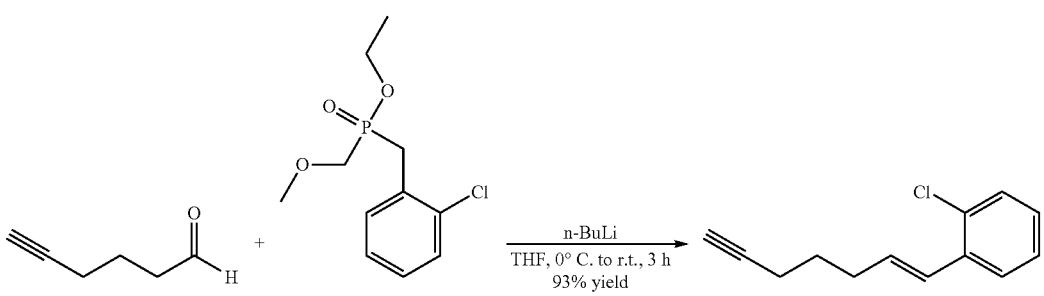

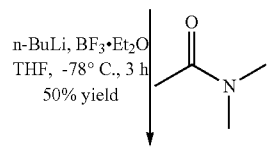

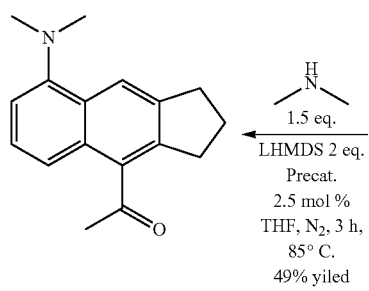 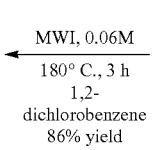

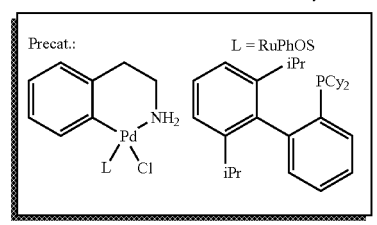

Literature Preparation. 5-Hexynal was prepared from 5-hexyn-1-ol through an oxidation reaction with PCC, which was reported by Kobayashi.[1] Diethyl 2-chlorobenzylphosphonate was prepared from 1-(bromomethyl)-2-chlorobenzene and triethyl phosphite via the procedure reported by Luscombe.

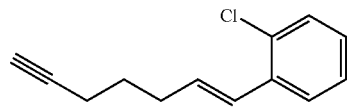

Synthesis of 1-chloro-2-(hept-1-en-6-yn-1-yl)benzene (EB-035)

An oven-dried 250 mL three-necked round-bottomed flask under a nitrogen atmosphere was charged with 3-chlorobenzylphosphonate (3.9 g, 15 mmol) and dry THF (60 mL). The solution was cooled to 0° C. in an ice bath for 15 min, then n-BuLi (12 mL of a 1.6 M n-hexane solution, 19 mmol) was added dropwise over 10 min, via syringe. The mixture was stirred at 0° C. for 30 min, then 5-hexynal (1.0 g, 10 mmol) in dry THF (40 mL) was added. The solution was warmed to room temperature and was stirred for 3 h. The consumption of the starting material was monitored by TLC (AcOEt/n-hexane 0.5:9.5). The reaction was quenched by adding saturated aqueous ammonium chloride solution (70 mL). The layers were separated and the aqueous phase was extracted with ether (3×50 mL). The combined organic layers were washed with brine (2×50 mL), dried over $Na_2SO_4$, gravity filtered and concentrated under reduced pressure. The reaction residue was purified by silica gel flash chromatography, eluting with AcOEt/n-hexane 0.5:9.5, to provide 1.11 g of the title compound as a colorless oil in 54% yield.

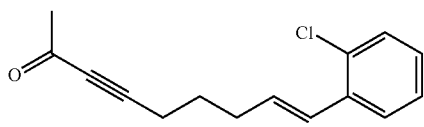 [SMILES: CC(=O)C#CCCC/C=C/c1ccccc1Cl]

Synthesis of 9-(2-chlorophenyl)non-8-en-3-yn-2-one (EB-037)

An oven-dried 100 mL three-necked round-bottomed flask under a nitrogen atmosphere was charged with compound EB-035 (1.11 g, 5.4 mmol) and dry THF (25 mL). The solution was cooled to −78° C. in a dry ice/acetone bath for 15 min, then n-BuLi (3.37 mL of a 1.6 M n-hexane solution, 5.4 mmol) was added via syringe. The mixture was stirred at −78° C. for 40 min, then N,N-dimethylacetamide (0.52 g, 0.55 mL, 5.9 mmol) and $BF_3.Et_2O$ (0.84 g, 0.74 mL, 5.9 mmol) were added. The solution was stirred at −78° C. for an additional 3 h. The consumption of the starting material was monitored by TLC (AcOEt/n-hexane 0.2:9.8). The reaction was quenched by adding saturated aqueous ammonium chloride solution (35 mL). The layers were separated and the aqueous phase was extracted with ether (3×30 mL). The combined organic layers were dried over $Na_2SO_4$, gravity filtered and concentrated under reduced pressure. The reaction residue was purified by silica gel flash chromatography, eluting with AcOEt/n-hexane 0.2:9.8 to 1:9, to provide 0.67 g of the title compound as a yellow oil in a 50% yield.

$^1$H NMR (400 MHz, CDCl$_3$) δ 7.49 (d, J=7.6 Hz, 1H), 7.33 (d, J=7.8 Hz, 1H), 7.24-7.10 (m, 2H), 6.80 (d, J=15.7 Hz, 1H), 6.16 (dt, J=15.7, 7.0 Hz, 1H), 2.43 (t, J=7.1 Hz, 2H), 2.37 (t, J=7.1 Hz, 2H), 2.33 (s, 3H), 1.79 (p, J=7.1 Hz, 2H) ppm $^{13}$C NMR (100 MHz, CDCl$_3$) δ 184.9, 135.6, 132.7, 132.0, 129.7, 128.3, 127.6, 126.9, 126.8, 93.5, 81.9, 32.9, 32.2, 27.2, 18.5 ppm IR (thin film) 3061, 2933, 2862, 2210, 1647, 1437, 1230 cm$^{-1}$ HRMS TOF MS ES+: $C_{15}H_{16}ClO$ Calculated: 247.0890; Found: 247.0874

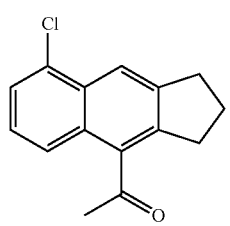 [SMILES: CC(=O)c1c2c(cc3c(Cl)cccc13)CCC2]

Synthesis of 1-(8-chloro-2,3-dihydro-1H-cyclopenta[b]naphthalen-4-yl)ethanone (EB-038)

A microwave irradiation vial (10-20 mL) was equipped with a sir bar (1.5 cm) and was charged with compound EB-037 (0.2 g, 0.81 mmol) and 1,2-dichlorobenzene (13.5 mL). The reaction was irradiated with stirring at 180° C. for 3 h, turning gold in color. The solution was directly charged into a silica gel column, which was eluted with n-hexane to separate the 1,2-dichlorobenzene and then AcOEt/n-hexane 1:9 to collect the pure product. The title compound was isolated as a yellow solid in a 86% yield (0.17 g).

$^1$H NMR (400 MHz, CDCl$_3$) δ 8.19 (s, 1H), 7.68 (d, J=8.5 Hz, 1H), 7.53 (d, J=7.3 Hz, 1H), 7.34 (t, J=8.0 Hz, 1H), 3.12 (t, J=7.3 Hz, 2H), 3.05 (t, J=7.3 Hz, 2H), 2.64 (s, 3H), 2.19 (p, J=7.3 Hz, 2H) ppm THF, 0.32 mmol), EB-038 (0.04 g, 0.16 mmol), dimethylamine (0.12 mL of a 2M solution in THF, 0.24 mmol) dry THF (0.3 mL). The title compound was isolated (n-hexane/AcOEt 9.5:0.5, 49% yield) as a yellow oil.

$^1$H NMR (400 MHz, CDCl$_3$) δ 8.16 (s, 1H), 7.43 (d, J=8.4 Hz, 1H), 7.35 (t, J=7.9 Hz, 1H), 7.06 (d, J=7.3 Hz, 1H), 3.09 (t, J=7.3 Hz, 2H), 3.03 (t, J=7.3 Hz, 2H), 2.87 (s, 6H), 2.64 (s, 3H), 2.16 (p, J=7.3 Hz, 2H) ppm $^{13}$C NMR (100 MHz, CDCl$_3$) δ 206.9, 151.1, 142.7, 139.3, 135.4, 129.8, 128.6, 125.9, 120.3, 119.5, 114.0, 45.5 (2CH$_3$), 32.8, 32.4, 32.0, 26.2 ppm IR (thin film) 2940, 2828, 2783, 1695, 1577, 1454, 1192 cm$^{-1}$ HRMS TOF MS ES+: C$_{17}$H$_{20}$NO Calculated: 254.1545; Found: 254.1543

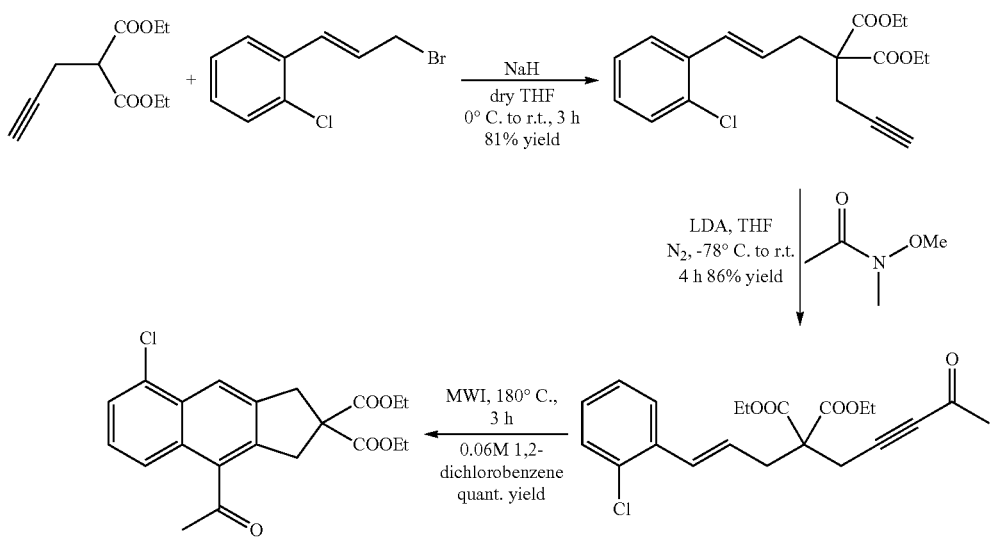

$^{13}$C NMR (100 MHz, CDCl$_3$) δ 206.0, 144.9, 140.5, 135.2, 132.2, 130.4, 129.7, 125.9, 125.8, 123.6, 120.6, 32.8, 32.3, 32.1, 26.2 ppm IR (thin film) 2952, 1690, 1410, 1350, 1187 cm$^{-1}$ HRMS TOF MS ES+: C$_{15}$H$_{14}$ClO Calculated: 245.0733; Found: 245.0719

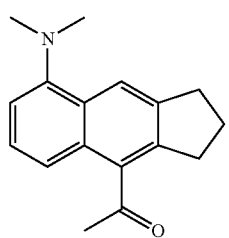 [SMILES: CC(=O)c1c2c(cc3c(N(C)C)cccc13)CCC2]

Synthesis of 1-(8-(dimethylamino)-2,3-dihydro-1H-cyclopenta[b]naphthalen-4-yl)ethanone (EB-039)

Substrate EB-039 was synthesized following the general procedure for the Buchwald-Hartwig couplings: precatalyst (0.003 g, 0.04 mmol), LHMDS (0.32 mL of a 1M solution in Literature Preparation. Diethyl 2-(prop-2-yn-1-yl)malonate was prepared from triethyl methanetricarboxylate through a procedure, which was previously reported by Brummond et al. *J. Am. Chem. Soc.* 2002, 124, 15186. (E)-1-(3-bromoprop-1-en-1-yl)-2-chlorobenzene was prepared starting from 2-chlorobenzaldehyde via the procedure reported by Fering a et al. *Adv. Synth. Catal.* 2004, 346, 413.

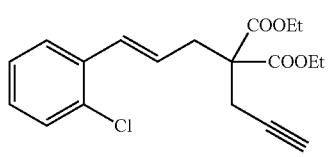 [SMILES: C#CCC(C/C=C/c1ccccc1Cl)(C(=O)OCC)C(=O)OCC]

Synthesis of diethyl 2-(3-(2-chlorophenyl)allyl)-2-(prop-2-yn-1-yl)malonate (EB-075)

An oven-dried, 100 mL three-necked round-bottomed flask under a nitrogen atmosphere was charged with compound diethyl 2-(prop-2-yn-1-yl)malonate (1.8 g, 9.1 mmol) (E)-1-(3-bromoprop-1-en-1-yl)-2-chlorobenzene (2.1 g, 11.0 mmol) and dry THF (60 mL). The solution was cooled to 0° C. in an ice bath for 15 min, then NaH (60% in mineral oil, 0.43 g 11.0 mmol) was added in one portion. The solution was stirred at 0° C. for 2 h. The consumption of the starting material was monitored by TLC (AcOEt/n-hexane 0.5:9.5). The reaction was then quenched by adding saturated aqueous ammonium chloride solution (70 mL). The layers were separated and the aqueous phase was extracted with AcOEt (3×50 mL). The combined organic layers were dried over Na$_2$SO$_4$, gravity filtered and concentrated under reduced pressure. The reaction residue was purified by silica gel flash chromatography, eluting with AcOEt/n-hexane 0.5:9.5, to provide 2.55 g of the title compound as a yellow oil in a 81% yield.

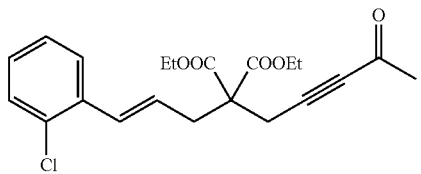 [SMILES: CCOC(=O)C(CC#CC(C)=O)(C/C=C/c1ccccc1Cl)C(=O)OCC]

Synthesis of diethyl 2-(3-(2-chlorophenyl)allyl)-2-(4-oxopent-2-yn-1-yl)malonate (EB-079)

An oven-dried 100 mL three-necked round-bottomed flask under a nitrogen atmosphere was charged with compound EB-075 (0.5 g, 1.4 mmol) and dry THF (20 mL). The solution was cooled to −78° C. in a dry ice/acetone bath for 15 min, then LDA (0.7 mL of a 2 M heptane/THF/ethylbenzene solution, 1.4 mmol) was added via syringe. The mixture was stirred at −78° C. for 1 h, then N-methoxy-N-methylacetamide (0.16 g, 0.16 mL, 1.54 mmol) was added. The solution was warmed to room temperature and was stirred for 4 h. The consumption of the starting material was monitored by TLC (AcOEt/n-hexane 1:9). The reaction was quenched by adding saturated aqueous ammonium chloride solution (40 mL). The layers were separated and the aqueous phase was extracted with ether (3×30 mL). The combined organic layers were dried over Na$_2$SO$_4$, gravity filtered and concentrated under reduced pressure. The reaction residue was purified by silica gel flash chromatography, eluting with AcOEt/n-hexane 2:8, to provide 0.47 g of the title compound as a colorless oil in a 86% yield.

$^1$H NMR (400 MHz, CDCl$_3$) δ 7.53 (d, J=7.2 Hz, 1H), 7.39 (t, J=7.7 Hz, 1H), 7.36-7.14 (m, 2H), 6.98 (d, J=15.6 Hz, 1H), 6.11 (dt, J=15.6, 7.6 Hz, 1H), 4.33 (q, J=7.1 Hz, 4H), 3.11 (s, 2H), 3.07 (d, J=7.6 Hz, 2H), 2.40 (s, 3H), 1.36 (t, J=7.1 Hz, 6H) ppm $^{13}$C NMR (100 MHz, CDCl$_3$) δ 183.9, 169.2 (2C), 134.9, 132.7, 131.3, 129.6, 128.7, 126.9, 126.9, 125.9, 87.7, 83.6, 62.1 (2CH$_2$), 56.8, 36.3, 32.9, 23.4, 14.1 (2CH$_3$) ppm IR (thin film) 2982, 2936, 2213, 1734, 1679, 1203 cm$^{-1}$ HRMS TOF MS ES+: C$_{21}$H$_{24}$O$_5$Cl Calculated: 391.1312; Found: 391.1299

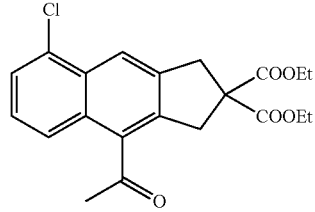 [SMILES: CCOC(=O)C1(C(=O)OCC)Cc2cc3c(Cl)cccc3c(C(C)=O)c2C1]

Synthesis of diethyl 4-acetyl-8-chloro-1H-cyclopenta[b]naphthalene-2,2(3H)-dicarboxylate (EB-081)

A microwave irradiation vial (10-20 mL) was equipped with a sir bar (1.5 cm) and was charged with compound EB-079 (0.3 g, 0.77 mmol) and 1,2-dichlorobenzene (12.8 mL). The reaction was irradiated with stirring at 180° C. for 30 min, turning gold in color. The solution was directly charged into a silica gel column, which was eluted with n-hexane to separate the 1,2-dichlorobenzene and then AcOEt/n-hexane 2:8 to collect the pure product. The title compound was isolated as a yellow oil in a quantitative yield (0.298 g). Small traces of contaminants were observed.

$^1$H NMR (400 MHz, CDCl$_3$) δ 8.17 (s, 1H), 7.67 (d, J=8.5 Hz, 1H), 7.53 (d, J=7.4 Hz, 1H), 7.35 (t, J=8.0 Hz, 1H), 4.27-4.17 (m, 4H), 3.76 (s, 2H), 3.68 (s, 2H), 2.66 (s, 3H), 1.38-1.13 (m, 6H).

$^{13}$C NMR (100 MHz, CDCl$_3$) δ 205.0, 170.9 (2C), 140.5, 136.7, 135.4, 132.3, 130.7, 130.0, 126.3, 126.3, 123.7, 121.0, 62.1 (2CH$_2$), 60.9, 40.1, 39.4, 32.3, 14.1 (2CH$_3$).

IR (thin film) 2981, 2935, 1731, 1697, 1253, 1185 cm$^{-1}$

HRMS TOF MS ES+: C$_{21}$H$_{22}$O$_5$Cl Calculated: 389.1156; Found: 389.1166

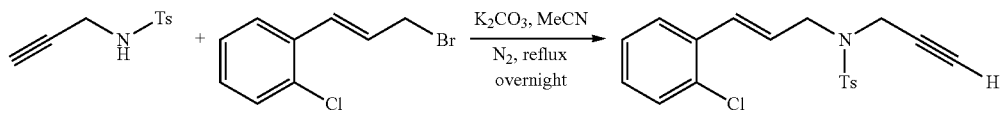

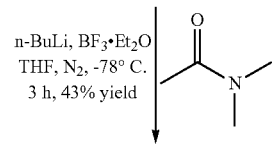

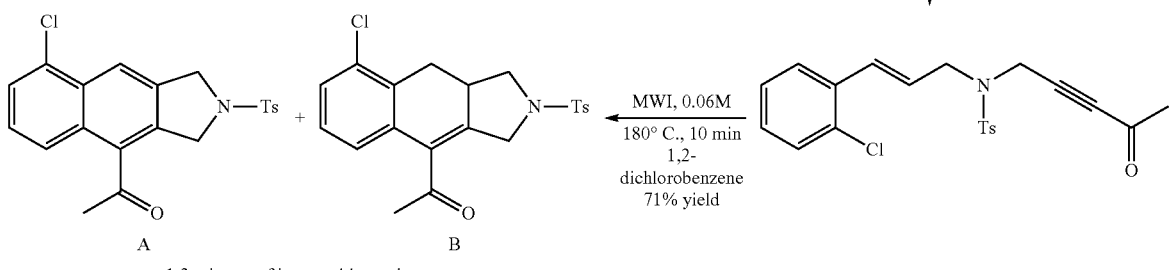

1:2 mixture of inseparable products

Literature Preparation. 4-Methyl-N-(prop-2-yn-1-yl)benzenesulfonamide was prepared from prop-2-yn-1-amine and 4-methylbenzene-1-sulfonyl chloride through a substitution reaction, which was reported by Gilbertson et al. *J. Org. Chem.* 2007, 72, 799. (E)-1-(3-bromoprop-1-en-1-yl)-2-chlorobenzene was prepared starting from 2-chlorobenzaldehyde via the procedure reported by Feringa.

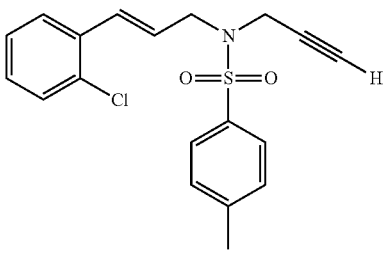 [SMILES: C#CCN(C/C=C/c1ccccc1Cl)S(=O)(=O)c1ccc(C)cc1]

Synthesis of N-(3-(2-chlorophenyl)allyl)-4-methyl-N-(prop-2-yn-1-yl)benzenesulfonamide (EB-047)

To an oven-dried, 100 mL, three-necked round-bottomed flask equipped with a stir bar, two septa and a nitrogen gas inlet adaptor, was added 4-methyl-N-(prop-2-yn-1-yl)benzenesulfonamide (1.0 g, 4.8 mmol) and $K_2CO_3$ (2.69 g, 19.2 mmol). The flask was evaporated and refilled with nitrogen three times, then MeCN (60 mL) was added. (E)-1-(3-bromoprop-1-en-1-yl)-2-chlorobenzene (1.66 g, 7.2 mmol) was added dropwise via syringe, turning the solution dark yellow. The mixture was heated at reflux and stirred overnight. The consumption of the starting material was monitored by TLC (AcOEt/n-hexane 1:9). At the end of the reaction the solvent was removed in vacuo. The reaction residue was taken up in saturated $NaHCO_3$ solution (70 mL) and extracted with ether (3×50 mL). The combined organic layers were washed with brine (70 mL), dried over $Na_2SO_4$, gravity filtered and concentrated under reduced pressure. The reaction residue was purified by silica gel flash chromatography, eluting with AcOEt/n-hexane 1:9, to provide 1.35 g of the title compound as a light yellow solid in a 78% yield.

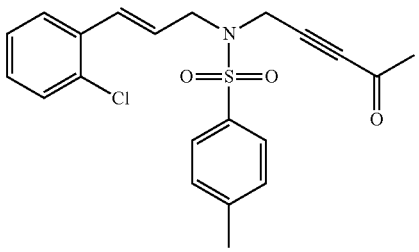 [SMILES: CC(=O)C#CCN(C/C=C/c1ccccc1Cl)S(=O)(=O)c1ccc(C)cc1]

Synthesis of N-(3-(2-chlorophenyl)allyl)-4-methyl-N-(4-oxopent-2-yn-1-yl)benzenesulfonamide (EB-050)

An oven-dried, 100 mL, three-necked round-bottomed flask under a nitrogen atmosphere was charged with compound EB-047 (1.0 g, 2.8 mmol) and dry THF (40 mL). The solution was cooled to −78° C. in a dry ice/acetone bath for 15 min, then n-BuLi (1.74 mL of a 1.6 M n-hexane solution, 2.8 mmol) was added via syringe. The mixture was stirred at −78° C. for 1 h, then N,N-dimethylacetamide (0.18 g, 0.19 mL, 2.1 mmol) and $BF_3.Et_2O$ (0.29 g, 0.26 mL, 2.1 mmol) were added. The solution was stirred at −78° C. for an additional 3 h. The consumption of the starting material was monitored by TLC (AcOEt/n-hexane 3:7). The reaction was quenched by adding saturated aqueous ammonium chloride solution (50 mL). The layers were separated and the aqueous phase was extracted with ether (3×30 mL). The combined organic layers were dried over $Na_2SO_4$, gravity filtered and concentrated under reduced pressure. The reaction residue was purified by silica gel flash chromatography, eluting with AcOEt/n-hexane 2:8, to provide 0.48 g of the title compound as a light yellow solid in a 43% yield.

$^1$H NMR (400 MHz, $CDCl_3$) δ 7.76 (d, J=8.2 Hz, 2H), 7.53-7.40 (m, 1H), 7.35-7.31 (m, 3H), 7.28-7.10 (m, 2H), 6.96 (d, J=15.7 Hz, 1H), 6.07 (dt, J=15.7, 6.8 Hz, 1H), 4.28 (s, 2H), 4.02 (d, J=6.7 Hz, 2H), 2.43 (s, 3H), 2.11 (s, 3H) ppm $^{13}$C NMR (100 MHz, $CDCl_3$) δ 183.2, 144.3, 135.5, 134.2, 133.2, 131.6, 129.9 (2CH), 129.8, 129.4, 127.9 (2CH), 127.2, 127.1, 125.6, 84.9, 84.2, 49.5, 36.4, 32.5, 21.6 ppm IR (thin film) 2920, 2209, 1679, 1351, 1162 cm$^{-1}$ HRMS TOF MS ES+: $C_{21}H_{21}NO_3SCl$ Calculated: 402.0931; Found: 402.0951

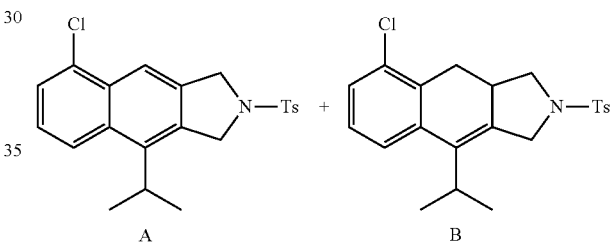

1:2 mixture of inseparable products

Synthesis of 1-(8-chloro-2-tosyl-2,3-dihydro-1H-benzo[f]isoindol-4-yl)ethanone (EB-067-A) and 1-(8-chloro-2-tosyl-2,3,9,9a-tetrahydro-1H-benzo[f]isoindol-4-yl)ethanone (EB-067-B)

A microwave irradiation vial (2-5 mL) was equipped with a sir bar (1 cm) and was charged with compound EB-050 (0.07 g, 0.17 mmol) and 1,2-dichlorobenzene (3 mL). The reaction was irradiated with stirring at 180° C. for 10 min, turning brown in color. The solution was directly charged into a silica gel column, which was eluted with n-hexane to separate the 1,2-dichlorobenzene and then AcOEt/n-hexane 2:8 to collect the pure products. The title compounds EB-067-A: EB-067-B were isolated as a 1:2 mixture of inseparable products in a 71% yield (0.048 g).

Data for EB-067-A and EB-067-B:

$^1$H NMR (400 MHz, $CDCl_3$) δ 8.18 (s, 1H minor) 7.80-7.71 (m, 3H major and 3H minor), 7.59 (d, J=7.4 Hz, 1H minor), 7.47-7.23 (m, 3H major and 2H minor), 7.16 (t, J=7.8 Hz, 1H major), 7.00 (d, J=7.6 Hz, 1H major), 4.77 (s, 2H minor), 4.70 (s, 2H minor), 4.55 (d, J=18.0 Hz, 1H major), 4.10 (m, 1H major), 3.99 (t, J=8.1 Hz, 1H major), 3.90 (d, J=18.0 Hz, 1H major), 3.38 (dd, J=15.4, 6.1 Hz, 1H major), 3.04-2.79 (m, 2H major), 2.65 (s, 3H minor), 2.43 (s, 3H major), 2.39 (s, 3H minor), 2.31 (s, 3H major) ppm $^{13}$C NMR (100 MHz, CDCl$_3$) δ 203.6 (minor), 200.3 (major), 148.6 (major), 144.2 (minor), 144.1 (major), 136.4 (minor), 134.2 (minor), 134.0 (major), 133.6 (1C major and 1C minor), 133.1 (minor), 132.9 (1C minor and 1C major), 132.7 (major), 132.5 (minor), 130.9 (minor), 130.2 (minor), 130.1 (2CH minor), 130.0 (2CH major), 129.1 (2CH major), 127.9 (major), 127.8 (2CH minor), 127.8 (major), 127.0 (minor), 126.9 (minor), 124.2 (major), 123.8 (minor), 120.2 (minor), 53.1 (minor), 52.8 (minor), 51.7 (major), 39.6 (major), 32.1 (minor), 30.1 (major), 28.6 (major), 21.7 (minor), 21.6 (major), 14.3 (major).

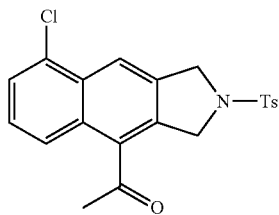 [SMILES: CC(=O)c1c2c(cc3c(Cl)cccc13)CN(S(=O)(=O)c1ccc(C)cc1)C2]

Synthesis of 1-(8-chloro-2-tosyl-2,3-dihydro-1H-benzo[f]isoindol-4-yl)ethanone (EB-051)

A microwave irradiation vial (10-20 mL) was equipped with a sir bar and was charged with compound EB-050 (0.3 g, 0.75 mmol) and 1,2-dichlorobenzene (12.4 mL). The reaction was irradiated with stirring at 180° C. for 3 h, turning black in color. The solution was directly charged into a silica gel column, which was eluted with n-hexane to separate the 1,2-dichlorobenzene and then AcOEt/n-hexane 2:8 to collect the pure product. The title compound was isolated as a brown solid in a 31% yield (0.093 g).

$^1$H NMR (400 MHz, CDCl$_3$) δ 8.13 (s, 1H), 7.78 (d, J=8.2 Hz, 2H), 7.70 (d, J=8.5 Hz, 1H), 7.56 (d, J=7.3 Hz, 1H), 7.39 (t, J=8.0 Hz, 1H), 7.32 (d, J=8.0 Hz, 2H), 4.73 (s, 2H), 4.69 (s, 2H), 2.63 (s, 3H), 2.38 (s, 3H).

$^{13}$C NMR (100 MHz, CDCl$_3$) δ 203.6, 144.2, 136.3, 134.1, 133.5, 133.1, 132.6, 130.9, 130.2, 130.0 (2CH), 127.8 (2CH), 127.0, 126.9, 123.8, 120.2, 53.1, 52.8, 32.1, 21.6.

IR (thin film) 2921, 1691, 1346, 1160 cm$^{-1}$

HRMS TOF MS ES+: C$_{21}$H$_{17}$NO$_3$SCl Calculated: 398.0618; Found: 398.0609

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the specifications and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

All numerical ranges stated herein include all sub-ranges subsumed therein. For example, a range of "1 to 10" is intended to include all sub-ranges between and including the recited minimum value of 1 and the recited maximum value of 10. Any maximum numerical limitation recited herein is intended to include all lower numerical limitations. Any minimum numerical limitation recited herein is intended to include all higher numerical limitations.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, for any reference made to patents and printed publications throughout this specification, each of the cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A functionalized naphthalene having a structure

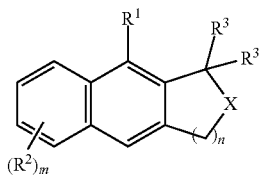

where $R^1$ is a substituent selected from the group consisting of H, $C_1$-$C_{20}$ alkyl, $C_1$-$C_{20}$ alkoxy, phenyl, aryl, heteroaryl, —S(O)$R^4$, —S(O)$_2$$R^4$, P(O)(O$R^4$)$_2$, and —C(Y)$R^4$ where Y is O, N$R^5$, or S; each $R^2$ is a halogen or —N($R^6$)$_2$; each $R^3$ is H, $C_1$-$C_{20}$ alkyl, or combined as =O; each $R^4$, $R^5$ and $R^6$ is independently selected from H, $C_1$-$C_{20}$ alkyl, $C_1$-$C_{20}$ alkoxy, substituted or unsubstituted phenyl, aryl, heteroaryl, benzyl, or two $R^6$ groups on an $R^2$ group may come together to form a cyclic structure; X is CH$_2$, C($R^6$)$_2$, C(CO$_2$Alkyl)$_2$, O, NTs, NH, NCO$R^5$ or N$R^5$; n is an integer from 0 to 2; m is an integer from 1 to 4, provided that either $R^1$ is one of —S(O)$R^4$, —S(O)$_2$$R^4$, P(O)(O$R^4$)$_2$, and —C(Y)$R^4$ or the $R^3$ groups are combined as =O.

2. The naphthalene of claim 1, wherein $R^1$ is —S(O)$R^4$, —S(O)$_2$$R^4$, P(O)(O$R^4$)$_2$, or —C(Y)$R^4$, Y is O or N$R^5$ and $R^4$ and $R^5$ are independently H, $C_1$-$C_{20}$ alkyl, $C_1$-$C_{20}$ alkoxy, phenyl, or aryl, and each $R^2$ is Cl or —N($R^6$)$_2$, where each $R^6$ is H, $C_1$-$C_{20}$ alkyl, substituted or unsubstituted phenyl, or benzyl, or two $R^6$ groups on an $R^2$ group come together to form a cyclyl or heterocyclyl structure having 4-5 carbon atoms.

3. The naphthalene of claim 2, wherein $R^1$ is —C(Y)$R^4$, Y is O, and $R^4$ is H, $C_1$-$C_{20}$ alkyl, $C_1$-$C_{20}$ alkoxy, phenyl, or aryl.

4. The naphthalene of claim 2, wherein $R^2$ is Cl.

5. The naphthalene of claim 2, wherein $R^2$ is —N($R^6$)$_2$, where each $R^6$ is H, $C_1$-$C_{20}$ alkyl, substituted or unsubstituted phenyl, or benzyl, or two $R^6$ groups on an $R^2$ group come together to form a cyclyl or heterocyclyl structure having 4-5 carbon atoms.

6. The naphthalene of claim 1, wherein the $R^3$ groups are combined as =O, X is CH$_2$, C($R^6$)$_2$, O, NTs, NH, NCO$R^5$ or N$R^5$, $R^1$ is H, $C_1$-$C_{20}$ alkyl, $C_1$-$C_{20}$ alkoxy, phenyl, aryl, or heteroaryl, and each $R^2$ is Cl or —N($R^6$)$_2$, where each $R^6$ is H, $C_1$-$C_{20}$ alkyl, substituted or unsubstituted phenyl, or benzyl, or two $R^6$ groups on an $R^2$ group come together to form a cyclyl or heterocyclyl structure having 4-5 carbon atoms.

7. The naphthalene of claim 1, wherein the naphthalene has a structure:

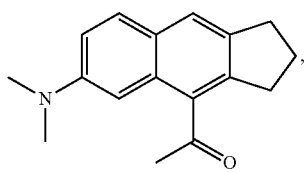

-continued

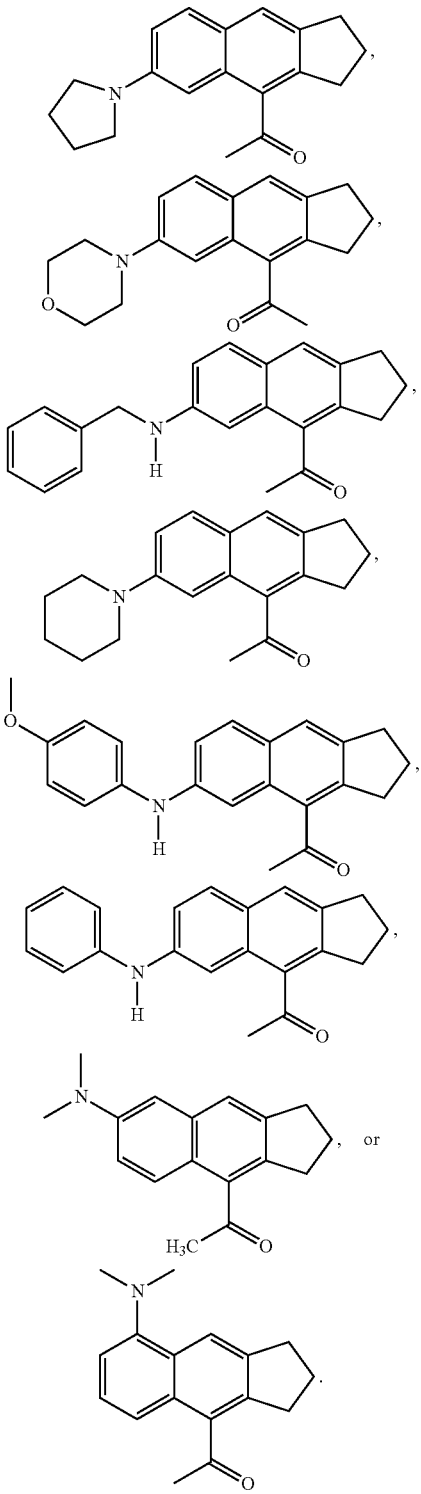

8. The naphthalene of claim 1, wherein the naphthalene is a fluorophore.

9. The naphthalene of claim 8, where the naphthalene has a fluorescent emission maximum at a wavelength of from 450 nm to 650 nm.

10. The naphthalene of claim 1, wherein the naphthalene is a solvatochromic fluorophore.

11. The naphthalene of claim 10, wherein the naphthalene displays a fluorescent emission maximum at a wavelength at least 50 nm longer than the fluorescent emission maximum of Prodan in the same solvent.

12. The naphthalene of claim 1, wherein the naphthalene is a liquid crystal.

13. A fluorescent sensor comprising:

a functionalized, substituted naphthalene having a structure:

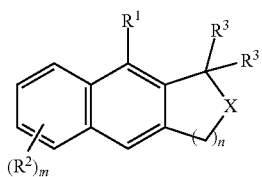

where $R^1$ is a substituent selected from the group consisting of H, $C_1$-$C_{20}$ alkyl, $C_1$-$C_{20}$ alkoxy, phenyl, aryl, heteroaryl, —S(O)$R^4$, —S(O)$_2R^4$, P(O)(O$R^4$)$_2$, and —C(Y)$R^4$ where Y is O, N$R^5$, or S; each $R^2$ is a halogen or —N($R^6$)$_2$; each $R^3$ is H, $C_1$-$C_{20}$ alkyl, or combined as =O; each $R^4$, $R^5$ and $R^6$ is independently selected from H, $C_1$-$C_{20}$ alkyl, $C_1$-$C_{20}$ alkoxy, substituted or unsubstituted phenyl, aryl, heteroaryl, benzyl, or two $R^6$ groups on an $R^2$ group may come together to form a cyclic structure; X is CH$_2$, C($R^6$)$_2$, C(CO$_2$Alkyl)$_2$, O, NTs, NH, NCOR$^5$ or N$R^5$; n is an integer from 0 to 2; m is an integer from 1 to 4, provided that either $R^1$ is one of —S(O)$R^4$, —S(O)$_2R^4$, P(O)(O$R^4$)$_2$, and —C(Y)$R^4$ or the $R^3$ groups are combined as =O.

14. A solvatochromic fluorophore comprising:

a functionalized, substituted naphthalene having a structure:

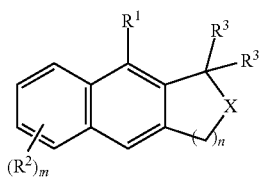

where $R^1$ is a substituent selected from the group consisting of H, $C_1$-$C_{20}$ alkyl, $C_1$-$C_{20}$ alkoxy, phenyl, aryl, heteroaryl, —S(O)$R^4$, —S(O)$_2R^4$, P(O)(O$R^4$)$_2$, and —C(Y)$R^4$ where Y is O, N$R^5$, or S; each $R^2$ is a halogen or —N($R^6$)$_2$; each $R^3$ is H, $C_1$-$C_{20}$ alkyl, or combined as =O; each $R^4$, $R^5$ and $R^6$ is independently selected from H, $C_1$-$C_{20}$ alkyl, $C_1$-$C_{20}$ alkoxy, substituted or unsubstituted phenyl, aryl, heteroaryl, benzyl, or two $R^6$ groups on an $R^2$ group may come together to form a cyclic structure; X is CH$_2$, C($R^6$)$_2$, C(CO$_2$Alkyl)$_2$, O, NTs, NH, NCOR$^5$ or N$R^5$; n is an integer from 0 to 2; m is an integer from 1 to 4, provided that either $R^1$ is one of —S(O)$R^4$, —S(O)$_2R^4$, P(O)(O$R^4$)$_2$, and —C(Y)$R^4$ or the $R^3$ groups are combined as =O.

15. The solvatochromic fluorophore of claim 14, wherein the functionalized, substituted naphthalene has a structure:

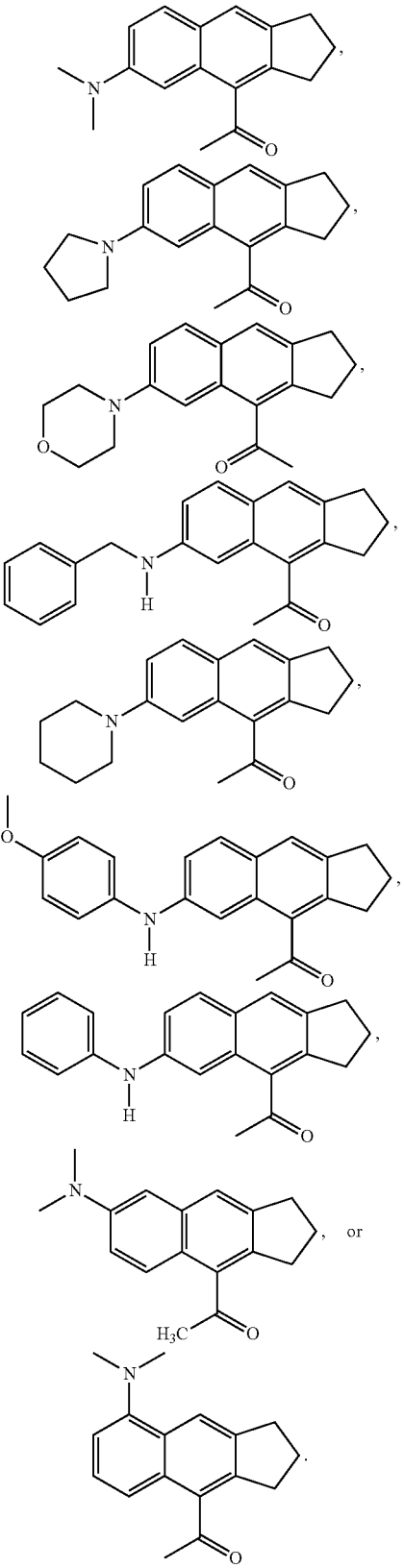

* * * * *